US011168345B2

(12) United States Patent
Mikkelsen et al.

(10) Patent No.: US 11,168,345 B2
(45) Date of Patent: Nov. 9, 2021

(54) METHODS OF IDENTIFYING A POLYPEPTIDE TARGET FOR DEGRADATION BY A MODULATOR OF CRBN

(71) Applicants: Tarjei Mikkelsen, Cambridge, MA (US); Benjamin Levine Ebert, Boston, MA (US); Quinlan Sievers, Boston, MA (US); THE BROAD INSTITUTE, INC., Cambridge, MA (US); PRESIDENT AND FELLOWS OF HARVARD COLLEGE, Cambridge, MA (US); THE BRIGHAM AND WOMEN'S HOSPITAL, INC., Boston, MA (US)

(72) Inventors: Tarjei Mikkelsen, Cambridge, MA (US); Benjamin Levine Ebert, Boston, MA (US); Quinlan Sievers, Boston, MA (US)

(73) Assignees: THE BROAD INSTITUTE, INC., Cambridge, MA (US); PRESIDENT AND FELLOWS OF HARVARD COLLEGE, Cambridge, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 156 days.

(21) Appl. No.: 15/759,168

(22) PCT Filed: Sep. 9, 2016

(86) PCT No.: PCT/US2016/051035
§ 371 (c)(1),
(2) Date: Mar. 9, 2018

(87) PCT Pub. No.: WO2017/044801
PCT Pub. Date: Mar. 16, 2017

(65) Prior Publication Data
US 2019/0071731 A1    Mar. 7, 2019

Related U.S. Application Data

(60) Provisional application No. 62/217,476, filed on Sep. 11, 2015, provisional application No. 62/258,929, filed on Nov. 23, 2015.

(51) Int. Cl.
| | | |
|---|---|---|
| *C12Q 1/02* | (2006.01) | |
| *C12Q 1/68* | (2018.01) | |
| *G01N 33/68* | (2006.01) | |
| *C07K 14/47* | (2006.01) | |
| *C12N 5/00* | (2006.01) | |
| *C12Q 1/6883* | (2018.01) | |
| *C07K 19/00* | (2006.01) | |
| *C12N 15/62* | (2006.01) | |
| *C12N 5/0781* | (2010.01) | |
| *C12N 5/09* | (2010.01) | |
| *C12N 5/07* | (2010.01) | |
| *C12Q 1/6886* | (2018.01) | |
| *A61P 35/00* | (2006.01) | |
| *A61K 31/4035* | (2006.01) | |
| *A61K 31/454* | (2006.01) | |

(52) U.S. Cl.
CPC .............. *C12Q 1/025* (2013.01); *C12Q 1/68* (2013.01); *G01N 33/68* (2013.01); *A61K 31/4035* (2013.01); *A61K 31/454* (2013.01); *A61P 35/00* (2018.01); *C07K 14/47* (2013.01); *C07K 19/00* (2013.01); *C07K 2319/95* (2013.01); *C12N 5/06* (2013.01); *C12N 5/0635* (2013.01); *C12N 5/0694* (2013.01); *C12N 15/62* (2013.01); *C12Q 1/6883* (2013.01); *C12Q 1/6886* (2013.01); *C12Q 2600/106* (2013.01); *C12Q 2600/136* (2013.01); *C12Q 2600/156* (2013.01)

(58) Field of Classification Search
CPC . C12Q 1/025; C12Q 1/02; C12Q 1/68; G01N 33/68
See application file for complete search history.

(56) References Cited

U.S. PATENT DOCUMENTS

2014/0162282 A1    6/2014  Schafer et al.

FOREIGN PATENT DOCUMENTS

| WO | 2015077058 A2 | 5/2015 | |
|---|---|---|---|
| WO | WO 2015/077058 | * | 5/2015 |

OTHER PUBLICATIONS

Office Action dated Nov. 29, 2019, received in corresponding European Patent Application No. 16845155.7, (4 pages).
Kronke et al., "Lenalidomide Causes Selective Degradation of IKZF1 and IKZF3 in Multiple Myeloma Cells", Science, vol. 343, No. 6168, Jan. 16, 2014, pp. 301-305.
Schafer et al., "The CUL4 (CRBN) E3 Ubiquitin Ligase Modulator CC-220 Induces Degradation of the Transcription Factors Ikaros and Aiolos: Immunumodulation in Healthy Volunteers and Relevance to Systemic Lupus Erythematosus", Arthritis & Rheumatology, vol. 66, No. Suppl. 10, Oct. 1, 2014, pp. S1176-S1177.
Extended European Search Report received in corresponding European Patent Application No. 16845155.7, dated Feb. 26, 2019 (6 pages).
Chamberlain, PP et al., "Structure of the Human Cereblon-DDB1-lenalidomide Complex Reveals Basis for Responsiveness to Thalidomide Analogs," Nature Structural and Molecular Biology, Sep. 2014, vol. 21, No. 9, pp. 803-810.

(Continued)

*Primary Examiner* — Zachary C Howard
(74) *Attorney, Agent, or Firm* — Melissa Hunter-Ensor; Leslie Serunian; Greenberg Traurig, LLP

(57) ABSTRACT

In one aspect, the invention features a method for identifying a drug-modulated polypeptide substrate of cereblon (CRBN). In another aspect, the invention features a method of identifying a polypeptide target of a modulator of CRBN. In yet another aspect, the invention provides methods of monitoring or characterizing the sensitivity of a subject to a modulator of CRBN.

9 Claims, 15 Drawing Sheets

Specification includes a Sequence Listing.

(56) References Cited

OTHER PUBLICATIONS

Lu, G. et al., "The Myeloma Drug Lenalidomide Promotes the Cereblon-Dependent Destruction of Ikaros Proteins," Science, Nov. 28, 2013, vol. 343, pp. 305-308.
International Search Report and Written Opinion for corresponding PCT Patent Application No. PCT/US16/51035, dated Mar. 17, 2017 (11 pages).
Office Action issued in corresponding European Patent Application No. 16845155.7, dated Jun. 8, 2020 (4 pages).
Office Action dated Nov. 16, 2020 as received in corresponding European Patent Application No. 16845155.7 (5 pages).

* cited by examiner

Aiolos Protein

… (1)

SEQUENCE LISTING

<160> NUMBER OF SEQ ID NOS: 22

<210> SEQ ID NO 1
<211> LENGTH: 23
<212> TYPE: PRT
<213> ORGANISM: Homo sapiens

<400> SEQUENCE: 1

Phe Gln Cys Asn Gln Cys Gly Ala Ser Phe Thr Gln Lys Gly Asn Leu
1               5                   10                  15

Leu Arg His Ile Lys Leu His
            20

<210> SEQ ID NO 2
<211> LENGTH: 24

<212> TYPE: PRT
<213> ORGANISM: Homo sapiens

<400> SEQUENCE: 2

Phe Ala Cys Pro Tyr Cys Gly Ala Arg Asn Leu Asp Gln Gln Glu Leu
1               5                   10                  15

Val Lys His Cys Val Glu Ser His
            20

<210> SEQ ID NO 3
<211> LENGTH: 23
<212> TYPE: PRT
<213> ORGANISM: Homo sapiens

<400> SEQUENCE: 3

Leu Gln Cys Glu Ile Cys Gly Phe Thr Cys Arg Gln Lys Ala Ser Leu
1               5                   10                  15

Asn Trp His Gln Arg Lys His
            20

<210> SEQ ID NO 4
<211> LENGTH: 23
<212> TYPE: PRT
<213> ORGANISM: Homo sapiens

<400> SEQUENCE: 4

Leu Gln Cys Glu Ile Cys Gly Phe Thr Cys Arg Gln Lys Ala Ser Leu
1               5                   10                  15

Asn Trp His Met Lys Lys His
            20

<210> SEQ ID NO 5
<211> LENGTH: 337
<212> TYPE: PRT
<213> ORGANISM: Homo sapiens

<400> SEQUENCE: 5

Met Ala Ser Ser Gly Ser Lys Ala Glu Phe Ile Val Gly Gly Lys
1               5                   10                  15

Tyr Lys Leu Val Arg Lys Ile Gly Ser Gly Ser Phe Gly Asp Ile Tyr
                20                  25                  30

Leu Ala Ile Asn Ile Thr Asn Gly Glu Glu Val Ala Val Lys Leu Glu
            35                  40                  45

Ser Gln Lys Ala Arg His Pro Gln Leu Leu Tyr Glu Ser Lys Leu Tyr
        50                  55                  60

Lys Ile Leu Gln Gly Gly Val Gly Ile Pro His Ile Arg Trp Tyr Gly
65                  70                  75                  80

Gln Glu Lys Asp Tyr Asn Val Leu Val Met Asp Leu Leu Gly Pro Ser
                85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
        115                 120                 125

Thr Lys Asn Phe Ile His Arg Asp Ile Lys Pro Asp Asn Phe Leu Met
    130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                165                 170                 175

```
Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
            195                 200                 205

Tyr Val Leu Met Tyr Phe Asn Arg Thr Ser Leu Pro Trp Gln Gly Leu
        210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
                245                 250                 255

Ala Met Tyr Leu Asn Tyr Cys Arg Gly Leu Arg Phe Glu Glu Ala Pro
            260                 265                 270

Asp Tyr Met Tyr Leu Arg Gln Leu Phe Arg Ile Leu Phe Arg Thr Leu
        275                 280                 285

Asn His Gln Tyr Asp Tyr Thr Phe Asp Trp Thr Met Leu Lys Gln Lys
    290                 295                 300

Ala Ala Gln Gln Ala Ala Ser Ser Ser Gly Gln Gly Gln Gln Ala Gln
305                 310                 315                 320

Thr Pro Thr Gly Lys Gln Thr Asp Lys Thr Lys Ser Asn Met Lys Gly
                325                 330                 335

Phe

<210> SEQ ID NO 6
<211> LENGTH: 2661
<212> TYPE: DNA
<213> ORGANISM: Homo sapiens

<400> SEQUENCE: 6
atgcgcagct gggcggtgac agggtgacgc tcggagcgtg ggccgcgact ctcacggatc      60
cggttccgcc ctctcgctgc cgatccttcg gagcgagcgc ccgagatccc tttcccagag     120
tgctctcgcg cgtgaagaag cggctcccgg ggactggggg cattttgtgt tggctggagc     180
tggagtaaca gatggcgtc gtccgcggag tgacaggggt ccctctgggc cggagccggc      240
ggcagtggtg gcagcggtat cgccgcccta gctcaccgcg cccctttttcc agcccgcgac    300 gtcgccgcgc aagcgaggca gcggcggccg ccgagaaaca gtggcccag cctggtaacc     360 gccgagaagc ccttcacaaa ctgcggcctg caaaaagaa acctgactga gcggcggtga     420
tcaggttccc ctctgctgat tctgggcccc gaaccccggt aaaggcctcc gtgttccgtt     480
tcctgccgcc ctcctccgta gccttgccta gtgtaggagc cccgaggcct ccgtcctctt     540
cccagaggtg tcggggcttg gccccagcct ccatcttcgt ctctcaggat ggcgagtagc     600
agcggctcca aggctgaatt cattgtcgga gggaaatata actggtacg gaagatcggg     660 tctggctcct tcggggacat ctatttggcg atcaacatca ccaacggcga ggaagtggca     720
gtgaagctag aatctcagaa ggccaggcat ccccagttgc tgtacgagag caagctctat     780
aagattcttc aaggtggggt tggcatcccc cacatacggt ggtatggtca ggaaaaagac     840
tacaatgtac tagtcatgga tcttctggga cctagcctcg aagacctctt caatttctgt     900
tcaagaaggt tcacaatgaa aactgtactt atgttagctg accagatgat cagtagaatt     960
gaatatgtgc atacaaagaa ttttatacac agagacatta accagataa cttcctaatg    1020 ggtattgggc gtcactgtaa taagtgttta aatctccag tggggaagag gaaaagaagc    1080
atgactgtta gtacttctca ggacccatct ttctcaggat taaaccagtt attccttatt    1140
```

```
gattttggtt tggccaaaaa gtacagagac aacaggacaa ggcaacacat accatacaga    1200
gaagataaaa acctcactgg cactgcccga tatgctagca tcaatgcaca tcttggtatt    1260
gagcagagtc gccgagatga catggaatca ttaggatatg ttttgatgta ttttaataga    1320
accagcctgc catggcaagg gctaaaggct gcaacaaaga aacaaaaata tgaaaagatt    1380
agtgaaaaga agatgtccac gcctgttgaa gttttatgta aggggttttcc tgcagaattt    1440 gcgatgtact taaactattg tcgtgggcta cgctttgagg aagccccaga ttacatgtat    1500
ctgaggcagc tattccgcat tcttttcagg accctgaacc atcaatatga ctacacattt    1560
gattggacaa tgttaaagca gaaagcagca cagcaggcag cctcttccag tgggcagggt    1620
cagcaggccc aaaccccccac aggcaagcaa actgacaaaa ccaagagtaa catgaaaggt    1680
ttctaagcat gaattgagga acagaagaag cagagcagat gatcggagca gcatttgttt    1740
ctccccaaat ctagaaattt tagttcatat gtacactagc cagtggttgt ggacaaccat    1800
ttacttggtg taaagaactt aatttcagta taaactgact ctgggcagca ttggtgatgc    1860
tgtatcctga gttgtagcct ctgtaattgt gaatattaac tgagatagtg aaacatggtg    1920
tccggttttc tattgcattt tttcaagtgg aaaagttaac taaatggttg acacacaaaa    1980
attggtggag aaattgtgca tatgccaatt ttttgttaaa accttttgtt ttgaactata    2040
ctgctttgag atctcatttc agaagaacgg catgaacagt cttcagccac agttgtgatg    2100
gttgttaaat gctcacaatt gtgcattctt agggttttc catccctggg gtttgcaagt    2160
tgttcactta aacattctt aaaatggttg gcttcttgtc tgcaagccag ctgatatggt    2220
agcaaccaaa gattccagtg tttgagcata tgaaagactc tgcctgctta attgtgctag    2280
aaataacagc atctaaagtg aagacttaag aaaaacttag tgactactag attatcctta    2340
ggactctgca ttaactctat aatgttcttg gtattaaaaa aaaagcatat ttgtcacaga    2400
aatttagtta acatcttaca actgaacatg tatgtatgtt gcttagataa atgtaatcac    2460
tgtaaacatc tatatgatct gggattttgt ttttatttg aaatgggagc ttttttgttt    2520
acaagttcat taaaaactaa aaactgtttc tgtaaggaaa tgagattttt tttaaacaac    2580
aaaaaatgcc ttgctgactc actattaaat aaaaatctcc ccaattttttt gatagactac    2640 ttcaaaaaaa aaaaaaaaa a                                                2661
```

<210> SEQ ID NO 7
<211> LENGTH: 441
<212> TYPE: PRT
<213> ORGANISM: Homo sapiens

<400> SEQUENCE: 7

```
Met Ala Gly Glu Gly Asp Gln Gln Asp Ala Ala His Asn Met Gly Asn
1               5                   10                  15

His Leu Pro Leu Leu Pro Glu Ser Glu Glu Glu Asp Glu Met Glu Val
                20                  25                  30

Glu Asp Gln Asp Ser Lys Glu Ala Lys Lys Pro Asn Ile Ile Asn Phe
            35                  40                  45

Asp Thr Ser Leu Pro Thr Ser His Thr Tyr Leu Gly Ala Asp Met Glu
        50                  55                  60

Glu Phe His Gly Arg Thr Leu His Asp Asp Ser Cys Gln Val Ile
65                  70                  75                  80

Pro Val Leu Pro Gln Val Met Met Ile Leu Ile Pro Gly Gln Thr Leu
                85                  90                  95

Pro Leu Gln Leu Phe His Pro Gln Glu Val Ser Met Val Arg Asn Leu
```

```
            100                 105                 110
Ile Gln Lys Asp Arg Thr Phe Ala Val Leu Ala Tyr Ser Asn Val Gln
            115                 120                 125

Glu Arg Glu Ala Gln Phe Gly Thr Thr Ala Glu Ile Tyr Ala Tyr Arg
            130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
            180                 185                 190

Met Ser Ala Val Gln Leu Glu Ser Leu Asn Lys Cys Gln Ile Phe Pro
            195                 200                 205

Ser Lys Pro Val Ser Arg Glu Asp Gln Cys Ser Tyr Lys Trp Trp Gln
            210                 215                 220

Lys Tyr Gln Arg Arg Lys Phe His Cys Ala Asn Leu Thr Ser Trp Pro
225                 230                 235                 240

Arg Trp Leu Tyr Ser Leu Tyr Asp Ala Glu Thr Leu Met Asp Arg Ile
                245                 250                 255

Lys Lys Gln Leu Arg Glu Trp Asp Glu Asn Leu Lys Asp Asp Ser Leu
            260                 265                 270

Pro Ser Asn Pro Ile Asp Phe Ser Tyr Arg Val Ala Ala Cys Leu Pro
            275                 280                 285

Ile Asp Asp Val Leu Arg Ile Gln Leu Leu Lys Ile Gly Ser Ala Ile
290                 295                 300

Gln Arg Leu Arg Cys Glu Leu Asp Ile Met Asn Lys Cys Thr Ser Leu
305                 310                 315                 320

Cys Cys Lys Gln Cys Gln Glu Thr Glu Ile Thr Thr Lys Asn Glu Ile
                325                 330                 335

Phe Ser Leu Ser Leu Cys Gly Pro Met Ala Ala Tyr Val Asn Pro His
            340                 345                 350

Gly Tyr Val His Glu Thr Leu Thr Val Tyr Lys Ala Cys Asn Leu Asn
            355                 360                 365

Leu Ile Gly Arg Pro Ser Thr Glu His Ser Trp Phe Pro Gly Tyr Ala
370                 375                 380

Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
                405                 410                 415

Thr Arg Ser Ala Leu Leu Pro Thr Ile Pro Asp Thr Glu Asp Glu Ile
            420                 425                 430

Ser Pro Asp Lys Val Ile Leu Cys Leu
            435                 440

<210> SEQ ID NO 8
<211> LENGTH: 441
<212> TYPE: PRT
<213> ORGANISM: Homo sapiens

<400> SEQUENCE: 8

Met Ala Gly Glu Gly Asp Gln Gln Asp Ala Ala His Asn Met Gly Asn
1               5                   10                  15

His Leu Pro Leu Leu Pro Glu Ser Glu Glu Glu Asp Glu Met Glu Val
            20                  25                  30
```

```
Glu Asp Gln Asp Ser Lys Glu Ala Lys Lys Pro Asn Ile Ile Asn Phe
             35                  40                  45

Asp Thr Ser Leu Pro Thr Ser His Thr Tyr Leu Gly Ala Asp Met Glu
 50                  55                  60

Glu Phe His Gly Arg Thr Leu His Asp Asp Ser Cys Gln Val Ile
 65                  70                  75                  80

Pro Val Leu Pro Gln Val Met Met Ile Leu Ile Pro Gly Gln Thr Leu
                 85                  90                  95

Pro Leu Gln Leu Phe His Pro Gln Glu Val Ser Met Val Arg Asn Leu
                100                 105                 110

Ile Gln Lys Asp Arg Thr Phe Ala Val Leu Ala Tyr Ser Asn Val Gln
                115                 120                 125

Glu Arg Glu Ala Gln Phe Gly Thr Thr Ala Glu Ile Tyr Ala Tyr Arg
130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
                180                 185                 190

Met Ser Ala Val Gln Leu Glu Ser Leu Asn Lys Cys Gln Ile Phe Pro
                195                 200                 205

Ser Lys Pro Val Ser Arg Glu Asp Gln Cys Ser Tyr Lys Trp Trp Gln
                210                 215                 220

Lys Tyr Gln Lys Arg Lys Phe His Cys Ala Asn Leu Thr Ser Trp Pro
225                 230                 235                 240

Arg Trp Leu Tyr Ser Leu Tyr Asp Ala Glu Thr Leu Met Asp Arg Ile
                245                 250                 255

Lys Lys Gln Leu Arg Glu Trp Asp Glu Asn Leu Lys Asp Asp Ser Leu
                260                 265                 270

Pro Ser Asn Pro Ile Asp Phe Ser Tyr Arg Val Ala Ala Cys Leu Pro
                275                 280                 285

Ile Asp Asp Val Leu Arg Ile Gln Leu Leu Lys Ile Gly Ser Ala Ile
                290                 295                 300

Gln Arg Leu Arg Cys Glu Leu Asp Ile Met Asn Lys Cys Thr Ser Leu
305                 310                 315                 320

Cys Cys Lys Gln Cys Gln Glu Thr Glu Ile Thr Thr Lys Asn Glu Ile
                325                 330                 335

Phe Ser Leu Ser Leu Cys Gly Pro Met Ala Ala Tyr Val Asn Pro His
                340                 345                 350

Gly Tyr Val His Glu Thr Leu Thr Val Tyr Lys Ala Cys Asn Leu Asn
                355                 360                 365

Leu Ile Gly Arg Pro Ser Thr Glu His Ser Trp Phe Pro Gly Tyr Ala
                370                 375                 380

Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
                405                 410                 415

Thr Arg Ser Ala Leu Leu Pro Thr Ile Pro Asp Thr Glu Asp Glu Ile
                420                 425                 430

Ser Pro Asp Lys Val Ile Leu Cys Leu
                435                 440
```

<210> SEQ ID NO 9
<211> LENGTH: 2213
<212> TYPE: DNA
<213> ORGANISM: Homo sapiens

<400> SEQUENCE: 9

```
gcgtgtaaac agacatggcc ggcgaaggag atcagcagga cgctgcgcac aacatgggca    60
accacctgcc gctcctgcct gagagtgagg aagaagatga aatggaagtt gaagaccagg   120
atagtaaaga agccaaaaaa ccaaacatca taaattttga caccagtctg ccgacatcac   180
atacatacct aggtgctgat atggaagaat tcatggcag  actttgcac gatgacgaca   240 gctgtcaggt gattccagtt cttccacaag tgatgatgat cctgattccc ggacagacat   300
tacctcttca gcttttttcac cctcaagaag tcagtatggt gcggaattta attcagaaag   360 atagaaccett tgctgttctt gcatacagca atgtacagga aagggaagca cagtttggaa   420
caacagcaga gatatatgcc tatcgagaag aacaggattt tggaattgag atagtgaaag   480
tgaaagcaat tggaagacaa aggttcaaag tccttgagct aagaacacag tcagatggaa   540
tccagcaagc taaagtgcaa attcttcccg aatgtgtgtt gccttcaacc atgtctgcag   600
ttcaattaga atccctcaat aagtgccaga tatttccttc aaaacctgtc tcaagagaag   660
accaatgttc atataaatgg tggcagaaat accagaggag aaagtttcat tgtgcaaatc   720
taacttcatg gcctcgctgg ctgtattcct tatatgatgc tgagacctta atggacagaa   780
tcaagaaaca gctacgtgaa tgggatgaaa atctaaaaga tgattctctt ccttcaaatc   840
caatagattt ttcttacaga gtagctgctt gtcttcctat tgatgatgta ttgagaattc   900
agctccttaa aattggcagt gctatccagc gacttcgctg tgaattagac attatgaata   960
aatgtacttc cctttgctgt aaacaatgtc aagaaacaga ataacaacc aaaaatgaaa    1020 tattcagttt atccttatgt gggccgatgg cagcttatgt gaatcctcat ggatatgtgc   1080
atgagacact tactgtgtat aaggcttgca acttgaatct gataggccgg ccttctacag   1140
aacacagctg gtttcctggg tatgcctgga ctgttgccca gtgtaagatc tgtgcaagcc   1200
atattggatg gaagtttacg gccaccaaaa aagacatgtc acctcaaaaa ttttggggct   1260
taacgcgatc tgctctgttg cccacgatcc cagacactga agatgaaata agtccagaca   1320
aagtaatact tgcttgtaa acagatgtga tagagataaa gttagttatc taacaaattg   1380
gttatattct aagatctgct ttggaaatta ttgcctctga tacataccta agtaaacata   1440
acattaatac ctaagtaaac ataacattac ttggagggtt gcagtttcta agtgaaactg   1500
tatttgaaac ttttaagtat actttaggaa acaagcatga acggcagtct agaataccag   1560
aaacatctac ttgggtagct tggtgccatt atcctgtgga atctgatatg tctggtagcg   1620
tgtcattgat gggacatgaa gacatctttg gaaatgatga gattatttcc tgtgttaaaa   1680
aaaaaaaaaa aatcttaaat tcctacaatg tgaaactgaa actaataatt tgatcctgat   1740
gtatgggaca gcgtatctgt accagtgctc taaataacaa agctagggt gacaagtaca   1800 tgttcctttt ggaaagaagc aaggcaatgt atattaatta ttctaaaagg ctttgttcc   1860 tttccatttt ctttaacttc tctgagatac tgatttgtaa attttgaaaa ttagttaaaa   1920
tatgcagttt tttgagccca cgaatagttg tcatttcctt tatgtgcctg ttagtaaaaa   1980
gtagtattgt gtatttgctc agtatctgaa ctataagccc atttatactg ttccatacaa   2040
aagctatttt tcaaaaatta atttgaacca aaactactac tatagggaaa agatgccaaa   2100
acatgtcccc tcacccaggc taaacttgat actgtattat tttgttcaat gtaaattgaa   2160
```
gaaaatctgt aagtaagtaa accttaagtg tgaaactaaa aaaaaaaaaa aaa         2213

<210> SEQ ID NO 10
<211> LENGTH: 477
<212> TYPE: PRT
<213> ORGANISM: Homo sapiens

<400> SEQUENCE: 10

Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Ile Lys Glu Glu Thr Asn His Ser Glu Met Ala
        195                 200                 205

Glu Asp Leu Cys Lys Ile Gly Ser Glu Arg Ser Leu Val Leu Asp Arg
    210                 215                 220

Leu Ala Ser Asn Val Ala Lys Arg Lys Ser Ser Met Pro Gln Lys Phe
225                 230                 235                 240

Leu Gly Asp Lys Gly Leu Ser Asp Thr Pro Tyr Asp Ser Ser Ala Ser
                245                 250                 255

Tyr Glu Lys Glu Asn Glu Met Met Lys Ser His Val Met Asp Gln Ala
            260                 265                 270

Ile Asn Asn Ala Ile Asn Tyr Leu Gly Ala Glu Ser Leu Arg Pro Leu
        275                 280                 285

Val Gln Thr Pro Pro Gly Gly Ser Glu Val Val Pro Val Ile Ser Pro
    290                 295                 300

Met Tyr Gln Leu His Lys Pro Leu Ala Glu Gly Thr Pro Arg Ser Asn
305                 310                 315                 320

His Ser Ala Gln Asp Ser Ala Val Glu Asn Leu Leu Leu Leu Ser Lys
                325                 330                 335

Ala Lys Leu Val Pro Ser Glu Arg Glu Ala Ser Pro Ser Asn Ser Cys
            340                 345                 350

Gln Asp Ser Thr Asp Thr Glu Ser Asn Asn Glu Glu Gln Arg Ser Gly
        355                 360                 365

-continued

```
Leu Ile Tyr Leu Thr Asn His Ile Ala Pro His Ala Arg Asn Gly Leu
370                 375                 380

Ser Leu Lys Glu Glu His Arg Ala Tyr Asp Leu Leu Arg Ala Ala Ser
385                 390                 395                 400

Glu Asn Ser Gln Asp Ala Leu Arg Val Val Ser Thr Ser Gly Glu Gln
                405                 410                 415

Met Lys Val Tyr Lys Cys Glu His Cys Arg Val Leu Phe Leu Asp His
            420                 425                 430

Val Met Tyr Thr Ile His Met Gly Cys His Gly Phe Arg Asp Pro Phe
        435                 440                 445

Glu Cys Asn Met Cys Gly Tyr His Ser Gln Asp Arg Tyr Glu Phe Ser
450                 455                 460

Ser His Ile Thr Arg Gly Glu His Arg Phe His Met Ser
465                 470                 475

<210> SEQ ID NO 11
<211> LENGTH: 519
<212> TYPE: PRT
<213> ORGANISM: Homo sapiens

<400> SEQUENCE: 11

Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
            85                  90                  95

Arg Asp Gln Gly Ser Ser Ala Leu Ser Gly Val Gly Gly Ile Arg Leu
        100                 105                 110

Pro Asn Gly Lys Leu Lys Cys Asp Ile Cys Gly Ile Ile Cys Ile Gly
    115                 120                 125

Pro Asn Val Leu Met Val His Lys Arg Ser His Thr Gly Glu Arg Pro
130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
            165                 170                 175

Leu Cys Asn Tyr Ala Cys Arg Arg Arg Asp Ala Leu Thr Gly His Leu
        180                 185                 190

Arg Thr His Ser Val Gly Lys Pro His Lys Cys Gly Tyr Cys Gly Arg
    195                 200                 205

Ser Tyr Lys Gln Arg Ser Ser Leu Glu Glu His Lys Glu Arg Cys His
210                 215                 220

Asn Tyr Leu Glu Ser Met Gly Leu Pro Gly Thr Leu Tyr Pro Val Ile
225                 230                 235                 240

Lys Glu Glu Thr Asn His Ser Glu Met Ala Glu Asp Leu Cys Lys Ile
            245                 250                 255

Gly Ser Glu Arg Ser Leu Val Leu Asp Arg Leu Ala Ser Asn Val Ala
        260                 265                 270
```

```
Lys Arg Lys Ser Ser Met Pro Gln Lys Phe Leu Gly Asp Lys Gly Leu
            275                 280                 285

Ser Asp Thr Pro Tyr Asp Ser Ser Ala Ser Tyr Glu Lys Glu Asn Glu
    290                 295                 300

Met Met Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Gly
                325                 330                 335

Gly Ser Glu Val Val Pro Val Ile Ser Pro Met Tyr Gln Leu His Lys
                340                 345                 350

Pro Leu Ala Glu Gly Thr Pro Arg Ser Asn His Ser Ala Gln Asp Ser
            355                 360                 365

Ala Val Glu Asn Leu Leu Leu Leu Ser Lys Ala Lys Leu Val Pro Ser
    370                 375                 380

Glu Arg Glu Ala Ser Pro Ser Asn Ser Cys Gln Asp Ser Thr Asp Thr
385                 390                 395                 400

Glu Ser Asn Asn Glu Glu Gln Arg Ser Gly Leu Ile Tyr Leu Thr Asn
                405                 410                 415

His Ile Ala Pro His Ala Arg Asn Gly Leu Ser Leu Lys Glu Glu His
            420                 425                 430

Arg Ala Tyr Asp Leu Leu Arg Ala Ala Ser Glu Asn Ser Gln Asp Ala
            435                 440                 445

Leu Arg Val Val Ser Thr Ser Gly Glu Gln Met Lys Val Tyr Lys Cys
    450                 455                 460

Glu His Cys Arg Val Leu Phe Leu Asp His Val Met Tyr Thr Ile His
465                 470                 475                 480

Met Gly Cys His Gly Phe Arg Asp Pro Phe Glu Cys Asn Met Cys Gly
                485                 490                 495

Tyr His Ser Gln Asp Arg Tyr Glu Phe Ser Ser His Ile Thr Arg Gly
                500                 505                 510

Glu His Arg Phe His Met Ser
            515

<210> SEQ ID NO 12
<211> LENGTH: 3572
<212> TYPE: DNA
<213> ORGANISM: Homo sapiens

<400> SEQUENCE: 12
ggcagcagag gaacctttg gaggaggaag aggacacaga ggccctgtag ccaggcacca      60
agatccctcc caggtggctg ggtctgaggg gaactccgag cagccctagg tcctcaaagt    120
ctggatttgt gtggaaaagg cagctctcac ttggccttgg cgaggcctcg gttggttgat    180
aacctgagga ccatggatgc tgatgagggt caagacatgt cccaagtttc agggaaggaa    240 agccccctg taagcgatac tccagatgag ggcgatgagc ccatgccgat ccccgaggac    300
ctctccacca cctcgggagg acagcaaagc tccaagagtg acagagtcgt ggccagtaat    360
gttaaagtag agactcagag tgatgaagag aatgggcgtg cctgtgaaat gaatggggaa    420
gaatgtgcgg aggatttacg aatgcttgat gcctcgggag agaaaatgaa tggctcccac    480
agggaccaag gcagctcggc tttgtcggga gttggaggca ttcgacttcc taacggaaaa    540
ctaaagtgtg atatctgtgg gatcatttgc atcgggccca atgtgctcat ggttcacaaa    600
agaagccaca ctggagaacg gccttccag tgcaatcagt gcggggcctc attcacccag    660
```

```
aagggcaacc tgctccggca catcaagctg cattccgggg agaagccctt caaatgccac    720
ctctgcaact acgcctgccg ccggagggac gccctcactg gccacctgag gacgcactcc    780
gtcattaaag aagaaactaa tcacagtgaa atggcagaag acctgtgcaa gataggatca    840
gagagatctc tcgtgctgga cagactagca agtaacgtcg ccaaacgtaa gagctctatg    900
cctcagaaat ttcttgggga caagggcctg tccgacacgc cctacgacag cagcgccagc    960
tacgagaagg agaacgaaat gatgaagtcc cacgtgatgg accaagccat caacaacgcc   1020
atcaactacc tgggggccga gtccctgcgc ccgctggtgc agacgccccc gggcggttcc   1080
gaggtggtcc cggtcatcag cccgatgtac cagctgcaca agccgctcgc ggagggcacc   1140
ccgcgctcca accactcggc ccaggacagc gccgtggaga acctgctgct gctctccaag   1200
gccaagttgg tgccctcgga gcgcgaggcg tccccgagca cagctgccga agactccacg   1260
gacaccgaga gcaacaacga ggagcagcgc agcggtctca tctacctgac caaccacatc   1320
gccccgcacg cgcgcaacgg gctgtcgctc aaggaggagc accgcgccta cgacctgctg   1380
cgcgccgcct ccgagaactc gcaggacgcg ctccgcgtgg tcagcaccag cggggagcag   1440
atgaaggtgt acaagtgcga acactgccgg gtgctcttcc tggatcacgt catgtacacc   1500
atccacatgg gctgccacgg cttccgtgat ccttttgagt gcaacatgtg cggctaccac   1560
agccaggacc ggtacgagtt ctcgtcgcac ataacgcgag gggagcaccg cttccacatg   1620
agctaaagcc ctcccgcgcc cccaccccag accccgagcc accccaggaa aagcacaagg   1680
actgccgcct tctcgctccc gccagcagca tagactggac tggaccagac aatgttgtgt   1740
ttggatttgt aactgttttt tgttttttgt ttgagttggt tgattggggt ttgatttgct   1800
tttgaaaaga ttttattttt tagaggcagg gctgcattgg gagcatccag aactgctacc   1860
ttcctagatg tttccccaga ccgctggctg agattccctc acctgtcgct tcctagaatc   1920
cccttctcca aacgattagt ctaaattttc agagagaaat agataaaaca cgccacagcc   1980
tgggaaggag cgtgctctac cctgtgctaa gcacggggtt cgcgcaccag gtgtcttttt   2040
ccagtcccca gaagcagaga gcacagcccc tgctgtgtgg gtctgcaggt gagcagacag   2100
gacaggtgtg ccgccaccca agtgccaaga cacagcaggg ccaacaacct gtgcccaggc   2160
cagcttcgag ctacatgcat ctagggcgga gaggctgcac ttgtgagaga aaatactatt   2220
tcaagtcata ttctgcgtag gaaaatgaat tggttgggga aagtcgtgtc tgtcagactg   2280
ccctgggtgg agggagacgc cgggctagag cctttgggat cgtcctggat tcactggctt   2340
tgcggaggct gctcagatgg cctgagcctc ccgaggcttg ctgccccgta ggaggagact   2400
gtcttcccgt gggcatatct ggggagccct gttccccgct ttttcactcc catacccttta  2460 atggccccca aaatctgtca ctacaattta acaccagtc ccgaaatttg gatcttcttt    2520 cttttttgaat ctctcaaacg gcaacattcc tcagaaacca aagctttatt tcaaatctct   2580
tccttccctg gctggttcca tctagtacca gaggcctctt ttcctgaaga aatccaatcc   2640
tagccctcat tttaattatg tacatctgtt tgtagccaca agcctgaatt tctcagtgtt   2700
ggtaagtttc tttacctacc ctcactatat attattctcg ttttaaaacc cataaaggag   2760
tgatttagaa cagtcattaa ttttcaactc aatgaaatat gtgaagccca gcatctctgt   2820
tgctaacaca cagagctcac ctgtttgaaa ccaagctttc aaacatgttg aagctcttta   2880
ctgtaaaggc aagccagcat gtgtgtccac acatacatag gatggctggc tctgcacctg   2940
taggatattg gaatgcacag ggcaattgag ggactgagcc agaccttcgg agagtaatgc   3000
caccagatcc cctaggaaag aggaggcaaa tggcactgca ggtgagaacc ccgcccatcc   3060
```

-continued

```
gtgctatgac atggaggcac tgaagcccga ggaaggtgtg tggagattct aatcccaaca    3120
agcaagggtc tccttcaaga ttaatgctat caatcattaa ggtcattact ctcaaccacc    3180
taggcaatga agaatatacc atttcaaata tttacagtac ttgtcttcac caacactgtc    3240
ccaaggtgaa atgaagcaac agagaggaaa ttgtacataa gtacctcagc atttaatcca    3300
aacaggggtt cttagtctca gcactatgac attttgggct gactacttat ttgttaggca    3360
ggagctctcc tgtgcattgt aggataatta gcagtatccc tggtggctac ccaatagacg    3420
ccagtagcac cccgaattga acccaaac tctccagaca tcaccaactg tccctgcga     3480 ggagaaatca ctcctggggg agaaccactg acccaaatga attctaaacc aatcaaatgt    3540
ctgggaagcc ctccaagaaa aaaaaaaaaa aa                                  3572
```

<210> SEQ ID NO 13
<211> LENGTH: 509
<212> TYPE: PRT
<213> ORGANISM: Homo sapiens

<400> SEQUENCE: 13

```
Met Glu Asp Ile Gln Thr Asn Ala Glu Leu Lys Ser Thr Gln Glu Gln
1               5                   10                  15

Ser Val Pro Ala Glu Ser Ala Ala Val Leu Asn Asp Tyr Ser Leu Thr
            20                  25                  30

Lys Ser His Glu Met Glu Asn Val Asp Ser Gly Gly Pro Ala Asn
        35                  40                  45

Glu Asp Glu Asp Ile Gly Asp Asp Ser Met Lys Val Lys Asp Glu Tyr
    50                  55                  60

Ser Glu Arg Asp Glu Asn Val Leu Lys Ser Glu Pro Met Gly Asn Ala
65                  70                  75                  80

Glu Glu Pro Glu Ile Pro Tyr Ser Tyr Ser Arg Glu Tyr Asn Glu Tyr
                85                  90                  95

Glu Asn Ile Lys Leu Glu Arg His Val Val Ser Phe Asp Ser Ser Arg
            100                 105                 110

Pro Thr Ser Gly Lys Met Asn Cys Asp Val Cys Gly Leu Ser Cys Ile
        115                 120                 125

Ser Phe Asn Val Leu Met Val His Lys Arg Ser His Thr Gly Glu Arg
    130                 135                 140

Pro Phe Gln Cys Asn Gln Cys Gly Ala Ser Phe Thr Gln Lys Gly Asn
145                 150                 155                 160

Leu Leu Arg His Ile Lys Leu His Thr Gly Glu Lys Pro Phe Lys Cys
                165                 170                 175

His Leu Cys Asn Tyr Ala Cys Gln Arg Arg Asp Ala Leu Thr Gly His
            180                 185                 190

Leu Arg Thr His Ser Val Glu Lys Pro Tyr Lys Cys Glu Phe Cys Gly
        195                 200                 205

Arg Ser Tyr Lys Gln Arg Ser Ser Leu Glu Glu His Lys Glu Arg Cys
    210                 215                 220

Arg Thr Phe Leu Gln Ser Thr Asp Pro Gly Asp Thr Ala Ser Ala Glu
225                 230                 235                 240

Ala Arg His Ile Lys Ala Glu Met Gly Ser Glu Arg Ala Leu Val Leu
                245                 250                 255

Asp Arg Leu Ala Ser Asn Val Ala Lys Arg Lys Ser Ser Met Pro Gln
            260                 265                 270

Lys Phe Ile Gly Glu Lys Arg His Cys Phe Asp Val Asn Tyr Asn Ser
```

```
            275                 280                 285
Ser Tyr Met Tyr Glu Lys Glu Ser Glu Leu Ile Gln Thr Arg Met Met
    290                 295                 300

Asp Gln Ala Ile Asn Asn Ala Ile Ser Tyr Leu Gly Ala Glu Ala Leu
305                 310                 315                 320

Arg Pro Leu Val Gln Thr Pro Pro Ala Pro Thr Ser Glu Met Val Pro
                325                 330                 335

Val Ile Ser Ser Met Tyr Pro Ile Ala Leu Thr Arg Ala Glu Met Ser
            340                 345                 350

Asn Gly Ala Pro Gln Glu Leu Glu Lys Lys Ser Ile His Leu Pro Glu
        355                 360                 365

Lys Ser Val Pro Ser Glu Arg Gly Leu Ser Pro Asn Asn Ser Gly His
    370                 375                 380

Asp Ser Thr Asp Thr Asp Ser Asn His Glu Glu Arg Gln Asn His Ile
385                 390                 395                 400

Tyr Gln Gln Asn His Met Val Leu Ser Arg Ala Arg Asn Gly Met Pro
                405                 410                 415

Leu Leu Lys Glu Val Pro Arg Ser Tyr Glu Leu Leu Lys Pro Pro Pro
            420                 425                 430

Ile Cys Pro Arg Asp Ser Val Lys Val Ile Asn Lys Glu Gly Glu Val
        435                 440                 445

Met Asp Val Tyr Arg Cys Asp His Cys Arg Val Leu Phe Leu Asp Tyr
    450                 455                 460

Val Met Phe Thr Ile His Met Gly Cys His Gly Phe Arg Asp Pro Phe
465                 470                 475                 480

Glu Cys Asn Met Cys Gly Tyr Arg Ser His Asp Arg Tyr Glu Phe Ser
                485                 490                 495

Ser His Ile Ala Arg Gly Glu His Arg Ala Leu Leu Lys
            500                 505

<210> SEQ ID NO 14
<211> LENGTH: 9686
<212> TYPE: DNA
<213> ORGANISM: Homo sapiens

<400> SEQUENCE: 14
gcaggagcac gtggagaggc cgagtagcca cagcggcagc tccagcccgg cccggcagcg      60
acatggaaga tatacaaaca aatgcggaac tgaaaagcac tcaggagcag tctgtgcccg     120
cagaaagtgc agcggttttg aatgactaca gtttaaccaa atctcatgaa atggaaaatg     180
tggacagtgg agaaggccca gccaatgaag atgaagacat aggagatgat tcaatgaaag     240
tgaaagatga atacagtgaa agagatgaga atgttttaaa gtcagaaccc atgggaaatg     300
cagaagagcc tgaaatccct tacagctatt caagagaata taatgaatat gaaaacatta     360
agttggagag acatgttgtc tcattcgata gtagcaggcc aaccagtgga agatgaact      420 gcgatgtgtg tggattatcc tgcatcagct tcaatgtctt aatggttcat aagcgaagcc     480
atactggtga acgcccattc agtgtaatca gtgtggggc atcttttact cagaaaggta     540
acctcctccg ccacattaaa ctgcacacag gggaaaaacc ttttaagtgt cacctctgca     600
actatgcatg ccaaagaaga gatgcgctca cggggcatct taggacacat tctgtggaga     660
aaccctacaa atgtgagttt tgtggaagga gttacaagca gaagaagttcc cttgaggagc     720 acaaggagcg ctgccgtaca tttcttcaga gcactgaccc aggggacact gcaagtgcgg     780
aggcaagaca catcaaagca gagatgggaa gtgaaagagc tctcgtactg acagattag     840
```

```
caagcaatgt ggcaaaacga aaaagctcaa tgcctcagaa attcattggt gagaagcgcc    900
actgctttga tgtcaactat aattcaagtt acatgtatga aaagagagt gagctcatac    960
agacccgcat gatggaccaa gccatcaata acgccatcag ctatcttggc gccgaagccc   1020
tgcgcccctt ggtccagaca ccgcctgctc ccacctcgga gatggttcca gttatcagca   1080
gcatgtatcc catagccctc acccgggctg agatgtcaaa cggtgcccct caagagctgg   1140
aaaagaaaag catccacctt ccagagaaga gcgtgccttc tgagagaggc ctctctccca   1200
acaatagtgg ccacgactcc acggacactg acagcaacca tgaagaacgc cagaatcaca   1260
tctatcagca aaatcacatg gtcctgtctc gggcccgcaa tgggatgcca cttctgaagg   1320
aggttccccg ctcttacgaa ctcctcaagc cccgcccat ctgcccaaga gactccgtca   1380
aagtgatcaa caaggaaggg gaggtgatgg atgtgtatcg gtgtgaccac tgccgcgtcc   1440
tcttcctgga ctatgtgatg ttcacgattc acatgggctg ccacggcttc cgtgacccett   1500
tcgagtgtaa catgtgtgga tatcgaagcc atgatcggta tgagttctcg tctcacatag   1560
ccagaggaga acacagagcc ctgctgaagt gaatatctgg tctcagggat tgctcctatg   1620
tattcagcat cgtttctaaa aaccaatgac ctcgcctaac agattgctct caaaacatac   1680
tcagttccaa acttcttttc ataccatttt tagctgtgtt cacaggggta gccagggaaa   1740
cactgtcttc cttcagaaat tattcgcagg tctagcatat tattactttt gtgaaacctt   1800
tgttttccca tcagggactt gaattttatg gaatttaaaa gccaaaaagg tatttggtca   1860
ttatcttcta cagcagtgga atgagtggtc ccggagatgt gctatatgaa acattctttc   1920
tgagatatat caaccacacg tggaaaagcc tttcagtcat acatgcaaat ccacaaagag   1980
gaagagctga ccagctgacc ttgctgggaa gcctcaccct tctgcccttc acaggctgaa   2040
gggttaagat ctaatctccc taatctaaat gacagtctaa gagtaagtaa aagaacagcc   2100
ataaaataag tatctgttac gagtaactga agacccatt ctccaagcat cagatccatt   2160
tcctatcaca acattttaa aaaatgtcat ctgatggcac ttctgcttct gtcctttacc   2220
ttcccatctc cagtgaaaag ctgagctgct ttgggctaaa ccagttgtct atagaagaaa   2280
atctatgcca gaagaactca tggttttaaa tatagaccat catcgaaact ccagaaattt   2340
atccactgtg gatgatgaca tcgctttcct ttggtcaagg ttggcagagc aagggtataa   2400
aggggaaat tgtttggcag caccaacaga aacaaacaa acaaaaaaca gctacctaaa    2460
acttcttgaa agagttcatg gagaattggt gatacagacc caaagcaaat ttgccaatga   2520
tattttccac aaaaaaagtc caaaaagtat ggctcagcct ccccctcccc acaggagagg   2580
aattggagat agatggcatg tgtgtttaga tcggagttga gctccggaat ggggtgagga   2640
gggacacctc tattgagagg ttctccttga tcaggcaggc ttcggccctt ttttccccat   2700
ttaaatggaa ctgctgtatt ccatgaaaat tcctgaaagt ctgatcacgg ttctgcagat   2760
gtataagtca tccttgtcac tcataatatg tacatactat caggaggagt gctgttatca   2820
tggtaaaatt agcactggaa taggaggtca caaaatgctg gctaattagc tatgtgactt   2880
tgagaaatcg tttaactttt tttttttttt tttttttgag acaggatctc actctgttgc   2940
ccaggctgga gtgcagtggt gcaatcatgg ctcagtgcag cctcgacctc ccaggctca   3000
ggtgatcctc ccacctcagc ctcttgagta ctgggacaac aagtgcacac caccatgtct   3060
ggctacattt tgttcttttt gtagagatag gggtctcact atgttgccca tgctggtctt   3120
gaactcctgg gctcaagcaa tcagcccgcc tcagcctcct aaagtgctgg gattacaggt   3180
```

-continued

```
gtgagccacc acacccagcc ttatttaact cttaaaactc agtttccggc caggctcggt    3240
ggctcacacc tgtaatccca acactttggg aagccgaggc aggcgcatca tttgaggtca    3300
ggagttcgag accagcctga cccacatggt gaaaccctgt ctctactaaa aatacaaaaa    3360
ttagctgggc agtagtggca catgcctgta atcccagcta ctccggaggc tgaggcagaa    3420
aaatcgctta agcctgggag gttgaggttg cggtgagtgg agatcacact actgcactcc    3480
agtctgggcg acagagtgag accctgtctc aaacaaaaca aaacaaaaac aaacaaacaa    3540
aaacaaaaaa aactcagttt cctcatccat aaaataggaa ttagatttca atgttctctt    3600
aggtcccttc tagctttaat tcatatgtga ttatgcagta accacaaggt atttttaaa    3660
cctcctaatg tatggatatt aagcagaaga gtatttatat gaatacatgt ttcacattcc    3720
tttggtatga aaatggtgtg ttaagttttt ccttttaacca ctgagttgtg aatgtgaaga    3780
aggtggtgga gaggaacaaa aaacagaaag gtattttgat cttgccacaa agcatacaca    3840
caaattggca catgcagctg tttgccaaag ccttcttttt tttttactt tttaagaaat    3900
tatgttaggg aaaataaatt ctgcttccag ggacaacttc atggagccta tttacaaatt    3960
aagagtcagc ttaatttgta acatttctac cagagccaag aatcccaaat tcctggtaga    4020
ttagtgtttt atttctaagg ggcttatgca ttcggctcca actcaactcg tctatgtgct    4080
gccagtaatt aaaatgttcc acctcagact gcacaaatgg cttatccttc tttgtggcat    4140
ggcgtctgtc tcaggaaaaa aggttttatg aaattccatg gcaacagtcc caacatgttt    4200
gagacttcag ctaaaggaat ggatgtattt tggtgtgtag tcttcagtat atcactgtat    4260
ttccgtaata ctagactcca agctatgcca gattgcttat tccctttgtg aaagaggagt    4320
tgctcattac gttcttgaaa tatcgcacat cctgttggtt cttcaaggga caagagaaag    4380
agaatttgga agcagggatt agtagaagag aaaacgaggg aaaggaagcc tttccaccag    4440
attagtgttc aagtctttgc agaggagacc aactttttttt gtttctttt gttttgagac    4500
agtctctcgc tctgttgccc aggctggagt gcagtggcgc gatctcggct cacgcaacc    4560
tccgcctccc gggttcaagc aattctcctg cctcagcctc ccaagtagct gggattacag    4620
gtgctcacca ccaagcccgg ctaattttttg tattttttagt agagacaagg tttcaccatg    4680
ttggccaggc cagtctcaaa ctcctgacct caggtgatct gcccgccttg cctcccaca    4740
gtgctgggat tacaggcatg agctaccgca cccagcctga gaccacctt tgcatctcaa    4800
gattgtgaaa ccaaggccca ttccaccagc ctggggactc ttttttataga tatgatcctc    4860
cttttttcctg tgactaatga atttgctgca tgatttctat tcttctgagg ttagttttct    4920
gagtaaggtg accactcaca aaggcacttt ctttgtggca ttctgagcct agattgggc    4980
ccatcaattc cagaaaaaat ttatgtgtgg aaactctgca tccttaagtc ttgaagttga    5040
accagatatg cagtggttac catcacacag ataaacgctg ccttctgtac ataccccta    5100
tgctgtacta attaacaaac cccttgccag ggctggggag gtgagggtga aggagaatct    5160
tagcagaagg gcagagtcag gacttgcatc tgccactgct gggcactgaa gccctggagc    5220
agcttcagat agtacctgta ctttctcatg cagactccct ctgaacaaga gccttgtagg    5280
ccctctcct tcatttccca ccagcctctt atcaggcggg ctttccacca tacacccagg    5340
aggccacggt ctgaggaaca accaaaccca tgcaaagggc cgggcgcgat agctcacgcc    5400
tgtaatgcca gcactttggg aggctggggc aggcagatca cctgaggttg ggagttcgag    5460
acctgcctga ccaacatgga gaaaccccca tctctactaa aaatacaaaa ttagccgggc    5520
gtgatggcac atgcctgtaa tcccagctac tcaggaggct gaggcaggag aatcgcttga    5580
```

```
acccgggagg cggaggttgc ggtgagccga gatggcacca ctgcactcca gcctcggcaa      5640
caagagcgaa actctgtcta aaacaaaaac aaacaaacaa acaaaaaaac ccaggcaaag      5700
tttccttgca gccaaggtga cagaactggg ctgagggtgg aaaagaaaca gaaccagtgc      5760
tccaggtgtt ttttaatttt ttaatttatt tttattttt tgtatatgt atatatatgt       5820 atgtatattt tagaggacca gggtctcact atgttgccta ggccagactc aaactcctgt      5880
gctcaagcaa tcctgcctca gcctcccaag tagctgggat tacaggcatg cacaaacaat      5940
gcccagctct ccaaatgttt tctgtcacta cctgaagtgt tgcatcggta cttcctacgg      6000
aaagaaaact aaatagaagt gtctctcccg tgagccccca ccactaccac cagaaaaaaa      6060
aaagagagaa aatgaactca tcagtcttta gtttcctcaa gttattctcc caaaagaca      6120 ttcgccttgg cacagataag ccagctaatc ttatgcttta tgacccactg tgagctgttc      6180
ctgacacagc ttctgacttt gtcagtgaca aaatttctca ccttttaaat gcagtgctta      6240
acattttgtt aggcccatac tcaaaatcgg ccagatataa aatgacctca gattttgatc      6300
tcctaggctc aaacaatcct cctacctcag cctcccaagt agctgggact ataggcacac      6360
caccatgcac agctaatttt ttttgtatt ttctgcagag atggcgtttc gccatactgc      6420
ccaggctagt ctcaaaatcc tgggctcaag caatctgccc acctcagcct cccaaagtgc      6480
tggaactaca ggcaagagcc actgcgccca gccacaacct cagatttctt tggcaaacag      6540
aaatgtttaa aaacacaaaa ttttgctcag gtgaaacact gtgttactat caaatctcac      6600
atccacataa agттттттctт ttcggctttg tttcgtgagg aacagacaga acaaagtttt      6660
tccaggtagc atctgtatca ctattattct cctatttcct gtaccacccc cacctcccca      6720
agccctactg aatgtgaggt ttagaatgtt ttaaggaggg tcaggtgcgg tggctcacgc      6780
ctgtaatccc agcactttgg gaggccaagg cgggcggatc acctgagttt gggagttcga      6840
gaccagcctg accaacatgg agaaaccctg tctctactaa aaatacaaaa ttagccaggc      6900
gtggtggcac atgcctgtaa tcccagctac ttaggaggct gaggcaggag aatcgcttga      6960
acccaggagg aggaggttgt ggtgagccga gatcgtgcca ttgcactcca gcctgggtga      7020
cagagtgaga ctccatctcg aaaaaaaaaa tacaaaaatt agctgggtgt ggtggtgcac      7080
acctgtaatc ccagctactc gggaggctga cgcaggagaa ttgcttgaac ctgggaggtg      7140
gaggttgcag tgagccgaga tcgcgccatt gcaatccagc ctggcaacaa gagtgagact      7200
ccatctcaaa aaaaaaaaaa aaagaatgt tttaaggaaa aaaatagtac tgttacatat      7260
aatcccaggt gataagacca caatggaaat gtttaagtcc tcactttaaa gagtacccca      7320
ctgagaagag gtatgttgga ctctagcaga gatttggaaa ctctgggaca ctcaagatgt      7380
gaaagagcct ggctatctga ggactcaaag agtcagcatc gggacttgtg agctcaagaa      7440
gagaaagggg agtggtgaaa ctttgtccta aaagttagca ccaggaacag aagaaaaaaa      7500
cccgatatat agtgatacct catcttttag agaatgggaa gctatttttg tgttcacaca      7560
gaaagtatag ttcaaaaaac ctctatatcc agagttcaga caaggagaat gatttgagat      7620
ataagtgccg atgaaggagg tcaattttga tctgaaacca gcagctggac ctgggccacc      7680
tcaggaaaag gactctgttc tccaaggcag cacgactgaa tggttctgag aataagccag      7740
ggttcaggac tcctgaccct ttaggaccat ggactcagaa gagcctgaag gacaattgtg      7800
ggctttaaac ttctgagagc ttgtaaagta acacaagact gtgcctctcc cttgccccag      7860
ctgtagatag tctttgcccc accattgtta tgaagataca cagggttttg cagtttgaat      7920
```

| | |
|---|---|
| aaattggata caagtttcct cttttttttt ttcttttga gacaaagtct cgctctgttt | 7980 |
| ccccaggctg agtgcagtgg cacaatcaag gcttacttgc cgcctcaacc tcctgggctc | 8040 |
| aagcaacgag ccatcctccc gtcttagcct cccaactagc tgagactaca ggcgtgggtc | 8100 |
| accacaccca gctaattttt gtacttttg tagagacagg gtctcaccat gttgcccagg | 8160 |
| ctggtcctga actcctgggc tcaagtaatc tgcccacctc agcctcccaa agtgttgggg | 8220 |
| ttacaggcgt gaggcaccgc ggctggcctg agtttcttct taatactgta tcacaattgt | 8280 |
| gggctgtctt atgtgttgat atcgattgag ctatttgaaa taggaatgtt aatgggtgta | 8340 |
| ttaaatttt gtaaggatat aacaatatct accttccaag gatgttgtga ggttttccat | 8400 |
| gattttgtat atgagctaat gttacctttg aggggtggtg tgcattatgt tggatgattg | 8460 |
| taaatttca gtggaaaatg taccgtgtcc taaatttaaa gacatgaaaa atatcccaag | 8520 |
| atcatactag atcataatag caattccttt acaaatgaat tatggaggta actgatctct | 8580 |
| aacagtttcc ttcatgttgt tttaatgcac aagggcagag gatctgctga cccttggaac | 8640 |
| cagcgtgagc taaccacgtg ctatagacac ttcatggtgt cgcacccagg gaagtcaaag | 8700 |
| cgctttgctc cctcactgtc tgtgagtcct cagccattag taccccaccc ccgctgctc | 8760 |
| caaaacttga gttatttcaa atgtttctca ctgttcatct ctccactgac cccactccag | 8820 |
| aaagcctgga gagagtccca agatgccacc caccttcccc aatccctcgc cacagatctg | 8880 |
| tgtctatctc acactctgta agtgccgctt tgcttcttcc tctcttgaaa agactgagaa | 8940 |
| cacacattt aacatgttag gaaaatgggg cagcctaaaa aatgactgat cccaccgcca | 9000 |
| gtgactcatg tatactccag gctagcagac aaggcccttt ttggtgggcc tgcttctgtg | 9060 |
| ggttcacaga aaccaaatta ctgtgggttg caaagaatta gcaggtcatt tacaaagcag | 9120 |
| acatcccttc acccagactg tggttttgca tgctcaggtt tcagtctat gagctttggt | 9180 |
| gcaggatcat tttggctact ggaaaaacca tagcttattt taaatttctg gttgccaaag | 9240 |
| ccaccacacg tgtggtctgt ggatgaccat tgtctgcaga atgacgagga aggaacagaa | 9300 |
| tgtggttgg ggctcagggt ggccttccca ctgggaggga aggcgggagg gagcccttgc | 9360 |
| cctgggtttt gacacagcct gtgctcacag cctctcctct catctgcatt tctcagaaat | 9420 |
| gccctccctg cccagtggtg actttccctc gtcactccta tggagttcta cctggagccc | 9480 |
| agccatgtgt ggaactgtga agtttactcc tctgtaaaga tggtttaaag aaagtcagct | 9540 |
| tctgaaatgt aacaatgcta accttgctg gaaccctgta agaaatagcc ctgctgatag | 9600 |
| ttttctaggt ttatcatgtt tgattttac actgaaaaat aaaaaaatcc tggtatgttt | 9660 |
| gaaattaaaa aaaaaaaaaa aaaaaa | 9686 |

<210> SEQ ID NO 15
<211> LENGTH: 237
<212> TYPE: PRT
<213> ORGANISM: Homo sapiens

<400> SEQUENCE: 15

Met Ala Met Phe Arg Ser Leu Val Ala Ser Gln Gln Arg Gln Pro
1               5                   10                  15

Pro Ala Gly Pro Ala Gly Gly Asp Ser Gly Leu Glu Ala Gln Tyr Thr
            20                  25                  30

Cys Pro Ile Cys Leu Glu Val Tyr His Arg Pro Val Ala Ile Gly Ser
        35                  40                  45

Cys Gly His Thr Phe Cys Gly Glu Cys Leu Gln Pro Cys Leu Gln Val
    50                  55                  60

```
Pro Ser Pro Leu Cys Pro Leu Cys Arg Leu Pro Phe Asp Pro Lys Lys
65                  70                  75                  80

Val Asp Lys Ala Thr His Val Glu Lys Gln Leu Ser Ser Tyr Lys Ala
                85                  90                  95

Pro Cys Arg Gly Cys Asn Lys Lys Val Thr Leu Ala Lys Met Arg Val
            100                 105                 110

His Ile Ser Ser Cys Leu Lys Val Gln Glu Gln Met Ala Asn Cys Pro
        115                 120                 125

Lys Phe Val Pro Val Val Pro Thr Ser Gln Pro Ile Pro Ser Asn Ile
    130                 135                 140

Pro Asn Arg Ser Thr Phe Ala Cys Pro Tyr Cys Gly Ala Arg Asn Leu
145                 150                 155                 160

Asp Gln Gln Glu Leu Val Lys His Cys Val Glu Ser His Arg Ser Asp
                165                 170                 175

Pro Asn Arg Val Val Cys Pro Ile Cys Ser Ala Met Pro Trp Gly Asp
            180                 185                 190

Pro Ser Tyr Lys Ser Ala Asn Phe Leu Gln His Leu Leu His Arg His
        195                 200                 205

Lys Phe Ser Tyr Asp Thr Phe Val Asp Tyr Ser Ile Asp Glu Glu Ala
    210                 215                 220

Ala Phe Gln Ala Ala Leu Ala Leu Ser Leu Ser Glu Asn
225                 230                 235

<210> SEQ ID NO 16
<211> LENGTH: 1888
<212> TYPE: DNA
<213> ORGANISM: Homo sapiens

<400> SEQUENCE: 16
ctacgatgac gtcagcgcgg cgcagtagcg gctgtgacta gcgggccggc ccgggccagg      60
acagcgggcg gcgggcggcg cgggcctggc cccgggatgg ctatgttccg cagcctggtg     120
gcctcggctc agcagcggca gccgccggcc gggccggcgg gcggcgacag cggcctggag     180
gcgcagtaca cctgccccat ctgcctggag gtctatcacc ggcccgtggc catcggcagc     240
tgcggccaca cgttctgcgg ggagtgtctc cagccctgcc tgcaggtgcc atccccgctg     300
tgcccactct gccgcctgcc cttcgacccc aagaaggtgg acaaggccac ccacgtggag     360
aagcagctct catcctacaa agcgccctgt cgaggctgca acaaaaaggt gaccctggca     420
aagatgagag tgcacatttc gtcctgcctg aaggtccagg agcagatggc caactgcccc     480
aagttcgtcc ccgtggtgcc cacatcacag cctatcccca gcaacatccc caacaggtcc     540
accttcgcct gccgtactg tggtgcccgc aacctggacc agcaggagct ggtgaagcac     600
tgtgtggaaa gccaccgcag cgaccccaac cgcgtggtgt gccccatctg ctcggcaatg     660
ccctgggggg accccagcta caagagcgcc aacttcctgc agcacctgct tcaccgacac     720
aagttctcct acgacacctt tgtggactac agtattgacg aggaggccgc cttccaggct     780
gctctggccc tgtctctctc tgagaactga agggaagcgc agccaccgc ctgcgtctgg     840 ggtcagggat gtccccgctc ctgtgtcgca cctggcacct gctcgggagc cacctcacc     900 ggactgagct cacaggagga gcctgcaccc gcgcagaagg ggagccgggg ccgagcctcc     960
gggcctgaat acgggccagc cgccgaggcc gccagagcag gccgcctgg tccaccggc    1020 gtcgctgggt tcttcggtgc ttctggccga gcaggcggcc tacttgggca gggctggacg    1080
ctgggacctg gagctgccgc cgtctcttca aagccatgat acccctcgt gggaagaagg    1140
```

```
gaccgacgcg cgagtcgcgc tccgcagtcg agccgggagg aacccaggct gctgccctgc  1200
ccagcccgac cctgccccgg ccccgcttcc accttgcgca tttggtactg gcttttgtga  1260
tacttaggaa ccctggcatc ttttctatat tatccagtgt gataatcttt tcacgtttta  1320
tagagcaaag acagagcagt tactcttcat attgcaatat ctgtgtttga ctaggaataa  1380
tagtattttt atggaacatt tacaaaatta tatttttaa gaaaacaatc aaaacaagca  1440
ttgggggatt gggcaagga tggaaggagc agtgggcag ctgccagagc tcaggcgagc  1500
catggggtct gctgtgggt ctgccctggc cacccactgt gtgtctgggt ccttgaggtt  1560
tgtacgtttc tctttgatga ccaggaagaa atcccagcac cccagccaca ggctgtggct  1620
gctcccagca gaggcgggc cggcagagaa ggggcctcct ccacccagag tcctggcctt  1680
ggcccgctgt caccttcaaa gctgactgtg ccccgctgcg ggaggggacg gcaccccagt  1740
ggtggcagag cttgggggcc tgggcagggg cccgcttggc gggccgggca acacgtcaac  1800
attcttttct gttcttggca ttaattattg ctgtcttttt tttaaaaaaa aaagtttaaa  1860
taaaatgtct cagagcatct ctaaaaaa                                    1888

<210> SEQ ID NO 17
<211> LENGTH: 570
<212> TYPE: PRT
<213> ORGANISM: Homo sapiens

<400> SEQUENCE: 17

Met Pro Gly Glu Thr Glu Glu Pro Arg Pro Glu Gln Gln Asp Gln
1               5                   10                  15

Glu Gly Gly Glu Ala Ala Lys Ala Ala Pro Glu Glu Pro Gln Gln Arg
                20                  25                  30

Pro Pro Glu Ala Val Ala Ala Pro Ala Gly Thr Thr Ser Ser Arg
            35                  40                  45

Val Leu Arg Gly Gly Arg Asp Arg Gly Arg Ala Ala Ala Ala Ala
        50                  55                  60

Ala Ala Ala Val Ser Arg Arg Lys Ala Glu Tyr Pro Arg Arg Arg
65                  70                  75                  80

Arg Ser Ser Pro Ser Ala Arg Pro Pro Asp Val Pro Gly Gln Gln Pro
                85                  90                  95

Gln Ala Ala Lys Ser Pro Ser Pro Val Gln Gly Lys Lys Ser Pro Arg
            100                 105                 110

Leu Leu Cys Ile Glu Lys Val Thr Thr Asp Lys Asp Pro Lys Glu Glu
        115                 120                 125

Lys Glu Glu Glu Asp Asp Ser Ala Leu Pro Gln Glu Val Ser Ile Ala
    130                 135                 140

Ala Ser Arg Pro Ser Arg Gly Trp Arg Ser Arg Thr Ser Val Ser
145                 150                 155                 160

Arg His Arg Asp Thr Glu Asn Thr Arg Ser Ser Arg Ser Lys Thr Gly
                165                 170                 175

Ser Leu Gln Leu Ile Cys Lys Ser Glu Pro Asn Thr Asp Gln Leu Asp
            180                 185                 190

Tyr Asp Val Gly Glu Glu His Gln Ser Pro Gly Gly Ile Ser Ser Glu
        195                 200                 205

Glu Glu Glu Glu Glu Glu Glu Met Leu Ile Ser Glu Glu Glu Ile
    210                 215                 220

Pro Phe Lys Asp Asp Pro Arg Asp Glu Thr Tyr Lys Pro His Leu Glu
225                 230                 235                 240
```

```
Arg Glu Thr Pro Lys Pro Arg Arg Lys Ser Gly Lys Val Lys Glu Glu
                245                 250                 255

Lys Glu Lys Lys Glu Ile Lys Val Glu Val Glu Val Lys Glu
        260                 265                 270

Glu Glu Asn Glu Ile Arg Glu Asp Glu Pro Pro Arg Lys Arg Gly
            275                 280                 285

Arg Arg Arg Lys Asp Asp Lys Ser Pro Arg Leu Pro Lys Arg Arg Lys
        290                 295                 300

Lys Pro Pro Ile Gln Tyr Val Arg Cys Glu Met Glu Gly Cys Gly Thr
305                 310                 315                 320

Val Leu Ala His Pro Arg Tyr Leu Gln His Ile Lys Tyr Gln His
                325                 330                 335

Leu Leu Lys Lys Lys Tyr Val Cys Pro His Pro Ser Cys Gly Arg Leu
                340                 345                 350

Phe Arg Leu Gln Lys Gln Leu Leu Arg His Ala Lys His His Thr Asp
                355                 360                 365

Gln Arg Asp Tyr Ile Cys Glu Tyr Cys Ala Arg Ala Phe Lys Ser Ser
        370                 375                 380

His Asn Leu Ala Val His Arg Met Ile His Thr Gly Glu Lys Pro Leu
385                 390                 395                 400

Gln Cys Glu Ile Cys Gly Phe Thr Cys Arg Gln Lys Ala Ser Leu Asn
                405                 410                 415

Trp His Met Lys Lys His Asp Ala Asp Ser Phe Tyr Gln Phe Ser Cys
                420                 425                 430

Asn Ile Cys Gly Lys Lys Phe Glu Lys Lys Asp Ser Val Val Ala His
                435                 440                 445

Lys Ala Lys Ser His Pro Glu Val Leu Ile Ala Glu Ala Leu Ala Ala
450                 455                 460

Asn Ala Gly Ala Leu Ile Thr Ser Thr Asp Ile Leu Gly Thr Asn Pro
465                 470                 475                 480

Glu Ser Leu Thr Gln Pro Ser Asp Gly Gln Gly Leu Pro Leu Leu Pro
                485                 490                 495

Glu Pro Leu Gly Asn Ser Thr Ser Gly Glu Cys Leu Leu Leu Glu Ala
                500                 505                 510

Glu Gly Met Ser Lys Ser Tyr Cys Ser Gly Thr Glu Arg Val Ser Leu
                515                 520                 525

Met Ala Asp Gly Lys Ile Phe Val Gly Ser Gly Ser Ser Gly Gly Thr
                530                 535                 540

Glu Gly Leu Val Met Asn Ser Asp Ile Leu Gly Ala Thr Thr Glu Val
545                 550                 555                 560

Leu Ile Glu Asp Ser Asp Ser Ala Gly Pro
                565                 570

<210> SEQ ID NO 18
<211> LENGTH: 5735
<212> TYPE: DNA
<213> ORGANISM: Homo sapiens

<400> SEQUENCE: 18
gtgggggggg cgccctcgga gccgggcgga ggggaggggg gaaagaggag cgcagggtga       60
gagtgagccg caggcttcgg gaggcgaggg ggcgggggga gcagcgccga ggccgccgcc      120
tccgcctccg ccgcctagga ctaggggggtg ggggacggac aagccccgat gccggggag      180 acggaagagc cgagacccccc ggagcagcag gaccaggaag ggggagaggc ggccaaggcg      240
```

```
gctccggagg agccccaaca acggcccct  gaggcggtcg cggcggcgcc tgcagggacc    300
actagcagcc gcgtgctgag gggaggtcgg gaccgaggcc gggccgctgc ggccgccgcc    360
gccgcagctg tgtcccgccg gaggaaggcc gagtatcccc gcggcggag  gagcagcccc    420 agcgccaggc ctcccgacgt ccccgggcag cagcccagg  ccgcgaagtc cccgtctcca    480
gttcagggca agaagagtcc gcgactccta tgcatagaaa aagtaacaac tgataaagat    540
cccaaggaag aaaagagga  agaagacgat tctgccctcc ctcaggaagt ttccattgct    600
gcatctagac ctagccgggg ctggcgtagt agtaggacat ctgtttctcg ccatcgtgat    660
acagagaaca cccgaagctc tcggtccaag accggttcat tgcagctcat ttgcaagtca    720
gaaccaaata cagaccaact tgattatgat gttggagaag agcatcagtc tccaggtggc    780
attagtagtg aagaggaaga ggaggaggaa gaagagatgt taatcagtga agaggagata    840
ccattcaaag atgatccaag agatgagacc tacaaacccc acttagaaag ggaaacccca    900
aagccacgga gaaaatcagg gaaggtaaaa gaagagaagg agaagaagga aattaaagtg    960
gaagtagagg tggaggtgaa agaagaggag aatgaaatta gagaggatga ggaacctcca   1020
aggaagagag gaagaagacg aaaagatgac aaaagtccac gtttacccaa aggagaaaa   1080 aagcctccaa tccagtatgt ccgttgtgag atggaaggat gtggaactgt ccttgcccat   1140
cctcgctatt tgcagcacca cattaaatac cagcatttgc tgaagaagaa atatgtatgt   1200
ccccatccct cctgtggacg actcttcagg cttcagaagc aacttctgcg acatgccaaa   1260
catcatacag atcaaaggga ttatatctgt gaatattgtg ctcgggcctt caagagttcc   1320
cacaatctgg cagtgcaccg gatgattcac actggcgaga agccattaca atgtgagatc   1380
tgtggattta cttgtcgaca aaaggcatct cttaattggc acatgaagaa acatgatgca   1440
gactccttct accagttttc ttgcaatatc tgtggcaaaa aatttgagaa gaggacagc   1500 gtagtggcac acaaggcaaa aagccaccct gaggtgctga ttgcagaagc tctggctgcc   1560
aatgcaggcg ccctcatcac cagcacagat atcttgggca ctaacccaga gtccctgacg   1620
cagccttcag atggtcaggg tcttcctctt cttcctgagc ccttgggaaa ctcaacctct   1680
ggagagtgcc tactgttaga agctgaaggg atgtcaaagt catactgcag tgggacggaa   1740
cgggtgagcc tgatggctga tgggaagatc tttgtgggaa gcggcagcag tggaggcact   1800
gaagggctgg ttatgaactc agatatactc ggtgctacca cagaggttct gattgaagat   1860
tcagactctg ccggacctta gtggacagga agacttgggg catgggacag ctcagacttt   1920
gtatttaaaa gttaaaaagg acaaaaaaaa aatctaaagc atttaaaatc tagtgaaata   1980
actgaagggc ctgctctttc cattgtggat cacagcacac acatacatac accctccacc   2040
tccccatccc ctgttctccc tctgttgctc cccttataaa attgatgttg tctttaccag   2100
aaaggtagac aaaaaagaag cagcagcagc tcttaaagtg agggttattc tcatactcgg   2160
ttccagccat cagcagactt cctgctcatc ggcagatccc cctttccaac ctgtaactct   2220
gatgtgctct ggatcagctt ttaactttta atcatatatt actgtcttct aaatcccttc   2280
tcctcctcta ctgctgccct atggttctgg ctcctacccc ctgcggcaca cttatcttca   2340
aataccatag aattctaatc tctggaggct ggcagcttga cttggcactt tagggcccct   2400
tagcagggtg agctgttaaa acagcacaca tctctcatcc cctcttcctt tattccccc    2460 tgggtttcag aaaggaagga tatatgggga ccacctcccc cttctttgat ccagcatct   2520 cagtccccct cccaacccctc catatggctc tcaatggtgc tcacttgctt ggaagcaggc   2580
```

```
tcccaatagg gaggggctg ccctctacag tctctttgac tgtaagacag ggctctgtat    2640
cagtgagacg atgagaaaag tcccaggcta atggcagaaa tttgcactt gaacatgtgt     2700 gttttttgtgt tgtggaacct gagattcctt atttattaac aggaagtctg attttttttt    2760
tttggagtct ttgttgctat attttgtggg gctgggagag agagattaga ttattttgac    2820
atgggatccc ttccataaca ggtactttga aggcaagaca tagggttgaa gaagcacagc    2880
cagcctctga aatcatagct ctccagtggc ttttaaagaa agctggtcct cagcactaac    2940
aaaatcacta caatagccta gtgcttttt ggaagccttt tagggaaga atgttaggtt      3000 catggtaact agtatgctct ttgagatttt tacagtgttg aaacttaaga attttgagag    3060
ggtgaggagg gttgttcaga atctaaatta cagatagatg attgtttctt gtgaatttgt    3120 ttctttttcct ttttttttgt ccctaccatt tccttacatt tcccttgggg cccatctctg    3180
gctccttgct ttttgtttct tgctttgctt tatcagttca ttccagctcc ctgttagtga    3240
aggacactgc tgttagtgaa ggaacaaagt ctatgagtcc taaaatttta agtcaaagaa    3300
aactgctctg tttcccctt agtaacactt ctgaagagga aaaacttcaa tagccaaagt     3360
taataatcct atataataat tgctttggct ttcacctaaa attctgggca tcacaatttc    3420
cttgggatag aggttgtgtt ggggaataga ttgcttattg ctgttcactg gagagaaaag    3480
gtagtgtttt tgtacaaggt cataccgcca gaagccccaa atcctattt ggctcatctt     3540 caggtaaaga gtaattccta tcctgtgtgc ctcagaagct agaatcgaag gcttaccta     3600 ttcattgttt attgtcagaa atgcatgatg gctcttggaa agaatgacgt tttgctggaa    3660 aaaaaaaaa gaacagtttg tgtttcacaa acatggctta tcaattttt caaagaattc      3720 ttttttccca aaagaggag taacaaaatg tcatttctga agaggctta ctttataccaa     3780 actagtgtca gcatttggga tgccagggaa cagagagtga gacacctaca atcaccagtc    3840
tcaaatgcgc tattgtttct tttcagagtg ttgcagattt gccatttctc cataatatgg    3900
ggatagaaaa tggaataaag atagaaggga tgtagaatat gctttcctgc caacatggtt    3960
tggagtcgac tttggtatat tgactagatt tgaaaataca agattgatta gatgaatcta   4020
caaaaaagtt gtcctcctct caggtcccct ttacacttt tgactaacta gcatctatat    4080
tccacactta gcttttttgt cacacttatc ctttgtctcc gtaaatttca tttgcagtgg    4140
ttagtcatca gatatttag ccacctacac aaaagcaaac tgcattttta aaatctttc      4200 tgagatggga gaaatgtat tctcctttcc tataccgctc tcccaacaaa aaaacaacta     4260
gttagttcta ctaattagaa acttgctgta cttttttctt tcttttaggg gtcaaggacc    4320
ctctttatag ctaccatttg cctacaataa attattgcag cagtttgcaa tactaaaata    4380 tttttttatag actttatatt tttccttttg ataaagggat gctgcatagt agagttggtg   4440
taattaaact atctcagccg tttccctgct ttcccttctg ctccatatgc ctcattgtcc    4500
ttccagggag ctctttaat cttaaagttc tacatttcat gctcttagtc aaattctgtt     4560
acctttttaa taactcttcc cactgcatat ttccatcttg aattggtggt tctaaattct    4620
gaaactgtag ttgagataca gctatttaat atttctggga gatgtgcatc cctcttcttt    4680
gtggttgccc aaggttgttt tgcgtaactg agactcctg atatgcttca gagaaattag     4740
gcaaacactg gccatggccg tgggagtact gggagtaaaa taaaaatatc gaggtataga    4800
ctagcatcca catagagcac ttgaacctcc tttgtacctg tttggggaaa agtataatg     4860 agtgtactac caatctaact aagattatta tagtctggtt gtttgaaata ccattttttt    4920
ctccttttgt gtttttccca ctttccaatg tactcaagaa aattgaacaa atgtaatgga    4980
```

```
tcaatttaaa atattttatt tcttaaaagc cttttttgcc tgttgtaatg tgcaggaccc      5040
ttctcctttc atgggagaga caggtagtta cctgaatata ggttgaaaag gttatgtaaa      5100
aagaaattat aataaaaggg atactttgct tttcaaatct ttgttttctc ttattctagg      5160
taaggcatat taaaaataaa tatgtaaaga agaaaaataa aagttgtctt catggaagca      5220
acttgtcttc cttggttgta ctgagttaca gttatcctag gggtgaaaca tgtgatgctg      5280
ctaagcaaac caaatgccct cagaacaggt gttatgtggg gcatactatt gtttgctttt      5340
gttgagaatc aggtggttaa tttttgactg ttcttgattt ctaatgctga aatgacatga      5400
ttctgttatt cagcaaactt ggaaatcttg atgttttgac aactgcctcc taggaaaact      5460
ggccatatgt taattaacct agtagatgga aaattaagga ttatgtgagg ttaattttac      5520
cctgataatg acaaaacctt gatagcattt aatattaata cttcttctca aaattgaatg      5580
tttatatcaa gtactgattt ttattttaaa aagaaaaaa  ctataatcct tctgccttcc      5640
aaaagccatg ctgtgatagc tgcccaggct gctctgttac atctcccatt tattgtttac      5700
ttttataaat ttgcttctaa gatggaaaaa aaaaa                                 5735
```

<210> SEQ ID NO 19
<211> LENGTH: 524
<212> TYPE: PRT
<213> ORGANISM: Homo sapiens

<400> SEQUENCE: 19

```
Met Pro Leu Val His Met Ala Ser Ser Pro Ala Val Asp Val Ser Cys
1               5                   10                  15

Arg Arg Arg Glu Lys Arg Arg Gln Leu Asp Ala Arg Arg Ser Lys Cys
            20                  25                  30

Arg Ile Arg Leu Gly Gly His Met Glu Gln Trp Cys Leu Leu Lys Glu
        35                  40                  45

Arg Leu Gly Phe Ser Leu His Ser Gln Leu Ala Lys Phe Leu Leu Asp
    50                  55                  60

Arg Tyr Thr Ser Ser Gly Cys Val Leu Cys Ala Gly Pro Glu Pro Leu
65                  70                  75                  80

Pro Pro Lys Gly Leu Gln Tyr Leu Val Leu Ser His Ala His Ser
            85                  90                  95

Arg Glu Cys Ser Leu Val Pro Gly Leu Arg Gly Pro Gly Gly Gln Asp
            100                 105                 110

Gly Gly Leu Val Trp Glu Cys Ser Ala Gly His Thr Phe Ser Trp Gly
        115                 120                 125

Pro Ser Leu Ser Pro Thr Pro Ser Glu Ala Pro Lys Pro Ala Ser Leu
    130                 135                 140

Pro His Thr Thr Arg Arg Ser Trp Cys Ser Glu Ala Thr Ser Gly Gln
145                 150                 155                 160

Glu Leu Ala Asp Leu Glu Ser Glu His Asp Glu Arg Thr Gln Glu Ala
                165                 170                 175

Arg Leu Pro Arg Arg Val Gly Pro Pro Glu Thr Phe Pro Pro
            180                 185                 190

Gly Glu Glu Glu Gly Glu Glu Glu Asp Asn Asp Glu Asp Glu Glu
        195                 200                 205

Glu Met Leu Ser Asp Ala Ser Leu Trp Thr Tyr Ser Ser Ser Pro Asp
    210                 215                 220

Asp Ser Glu Pro Asp Ala Pro Arg Leu Leu Pro Ser Pro Val Thr Cys
225                 230                 235                 240
```

```
Thr Pro Lys Glu Gly Glu Thr Pro Ala Pro Ala Ala Leu Ser Ser
            245                 250                 255
Pro Leu Ala Val Pro Ala Leu Ser Ala Ser Ser Leu Ser Ser Arg Ala
        260                 265                 270
Pro Pro Pro Ala Glu Val Arg Val Gln Pro Gln Leu Ser Arg Thr Pro
        275                 280                 285
Gln Ala Ala Gln Gln Thr Glu Ala Leu Ala Ser Thr Gly Ser Gln Ala
        290                 295                 300
Gln Ser Ala Pro Thr Pro Ala Trp Asp Glu Asp Thr Ala Gln Ile Gly
305                 310                 315                 320
Pro Lys Arg Ile Arg Lys Ala Ala Lys Arg Glu Leu Met Pro Cys Asp
                325                 330                 335
Phe Pro Gly Cys Gly Arg Ile Phe Ser Asn Arg Gln Tyr Leu Asn His
            340                 345                 350
His Lys Lys Tyr Gln His Ile His Gln Lys Ser Phe Ser Cys Pro Glu
        355                 360                 365
Pro Ala Cys Gly Lys Ser Phe Asn Phe Lys Lys His Leu Lys Glu His
        370                 375                 380
Met Lys Leu His Ser Asp Thr Arg Asp Tyr Ile Cys Glu Phe Cys Ala
385                 390                 395                 400
Arg Ser Phe Arg Thr Ser Ser Asn Leu Val Ile His Arg Arg Ile His
                405                 410                 415
Thr Gly Glu Lys Pro Leu Gln Cys Glu Ile Cys Gly Phe Thr Cys Arg
            420                 425                 430
Gln Lys Ala Ser Leu Asn Trp His Gln Arg Lys His Ala Glu Thr Val
        435                 440                 445
Ala Ala Leu Arg Phe Pro Cys Glu Phe Cys Gly Lys Arg Phe Glu Lys
        450                 455                 460
Pro Asp Ser Val Ala Ala His Arg Ser Lys Ser His Pro Ala Leu Leu
465                 470                 475                 480
Leu Ala Pro Gln Glu Ser Pro Ser Gly Pro Leu Glu Pro Cys Pro Ser
                485                 490                 495
Ile Ser Ala Pro Gly Pro Leu Gly Ser Ser Glu Gly Ser Arg Pro Ser
            500                 505                 510
Ala Ser Pro Gln Ala Pro Thr Leu Leu Pro Gln Gln
        515                 520
```

<210> SEQ ID NO 20
<211> LENGTH: 2208
<212> TYPE: DNA
<213> ORGANISM: Homo sapiens

<400> SEQUENCE: 20

| | | | | | |
|---|---|---|---|---|---|
| ggcgcacagg | taaggccggg | gtgggggtgg | gtcgcgacgg | gggctctggg | cagcctggga | 60 |
| actgccattg | ggattagtcc | gctccactca | ctgtcagcat | taagtggggg | tgcccaagac | 120 |
| ggggtggatg | gggggcgccc | tccagacctc | tgaccacggc | ctcaccgcca | ctcgacccaa | 180 |
| ctatgaagag | cgcccccagc | tgcacgccag | gacacgacct | ttccttcccc | tagaaaccag | 240 |
| taaaggccgc | tgcccctattc | aagatgaaat | gtgtggaccg | cccccagccc | agttgaaatt | 300 |
| tcccgtgaaa | gtctctcgcc | ccttccccac | agctccactt | cagtggactg | gagggcgcag | 360 |
| gcctttgttc | tgactgcttc | tgtctgcctg | cctcccaccc | gacgacactc | acatgcctct | 420 |
| ggtgcacatg | gcttcctccc | cggcggtgga | cgtgtcctgc | aggcggcggg | agaagcggcg | 480 |

```
gcagctggac gcgcgccgca gcaagtgccg catccgcctg ggcggccaca tggagcagtg    540
gtgcctcctc aaggagcggc tgggcttctc cctgcactcg cagctcgcca agttcctgtt    600
ggaccggtac acttcttcag gctgtgtcct ctgtgcaggt cctgagcctt tgcctccaaa    660
aggtctgcag tatctggtgc tcttgtctca tgcccacagc cgagagtgca gcctggtgcc    720
cgggcttcgg gggcctggcg gccaagatgg ggggcttgtg tgggagtgct cagcaggcca    780
taccttctcc tggggaccct ctttgagccc tacaccttca gaggcaccca agccagcctc    840
ccttccacat actactcgga gaagttggtg ttccgaggcc acgagtgggc aggagcttgc    900
agatttggaa tctgagcatg atgagaggac tcaagaggcc aggttgccca ggagggtggg    960
acccccacca gagaccttcc cacctccagg agaggaagag ggtgaggaag aagaggacaa   1020
tgatgaggat gaagaggaga tgctcagtga tgccagctta tggacctaca gctcctcccc   1080
agatgatagt gagcctgatg cccccagact actgccttcc cctgtcacct gcacacctaa   1140 agaggggag acaccaccag ccctgcagc actctccagt cctcttgctg tgccggcctt    1200
gtcagcatcc tcattgagtt ccagagctcc tccacctgca gaagtcaggg tgcagccaca   1260
gctcagcagg acccctcaag cggcccagca gactgaggcc ctggccagca ctgggagtca   1320
ggcccagtct gctccaaccc cggcctggga tgaggacact gcacaaattg ccccaagag    1380 aattaggaaa gctgccaaaa gagagctgat gccttgtgac ttccctggct gtggaaggat   1440
cttctccaac cggcagtatt tgaatcacca caaaaagtac cagcacatcc accagaagtc   1500
tttctcctgc ccagagccag cctgtgggaa gtctttcaac tttaagaaac acctgaagga   1560
gcacatgaag ctgcacagtg acacccggga ctacatctgt gagttctgcg cccggtcttt   1620
ccgcactagc agcaaccttg tcatccacag acgtatccac actggagaaa aaccccctgca  1680 gtgtgagata tgcgggttta cctgccgcca gaaggcttcc ctgaactggc accagcgcaa   1740
gcatgcagag acggtggctg ccttgcgctt ccctgtgaa ttctgcggca gcgctttga    1800 gaagccagac agtgttgcag cccaccgtag caaaagtcac ccagccctgc ttctagcccc   1860
tcaagagtca cccagtggtc ccctagagcc ctgtcccagc atctctgccc ctgggcctct   1920
gggatccagc gaggggtcca ggccctctgc atccctcag gctccaaccc tgcttcctca   1980
gcaatgagct ctcctccagc tttggctttg ggaagccaga ctccagggac tgaaaaggag   2040
caacaaggag agggtctgct tgagaaatgc cagatgcttg gtccccagga actaaggcga   2100
cagagtgcag ggtggggggca agactgggct gtaggggagc tggactactt tagtcttcct   2160
aaaggacaaa ataaacagta ttttatgcag gcaaaaaaaa aaaaaaaa              2208
```

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Glu Arg Pro Phe Gln Cys Asn Gln Cys Gly Ala Ser Phe Thr Gln
1               5                   10                  15

Lys Gly Asn Leu Leu Arg His Ile Lys Leu
            20                  25

<210> SEQ ID NO 22
<211> LENGTH: 60
<212> TYPE: PRT

```
<213> ORGANISM: Homo sapiens

<400> SEQUENCE: 22

Phe Asn Val Leu Met Val His Lys Arg Ser His Thr Gly Glu Arg Pro
1               5                   10                  15

Phe Gln Cys Asn Gln Cys Gly Ala Ser Phe Thr Gln Lys Gly Asn Leu
                20                  25                  30

Leu Arg His Ile Lys Leu His Thr Gly Glu Lys Pro Phe Lys Cys His
            35                  40                  45

Leu Cys Asn Tyr Ala Cys Gln Arg Arg Asp Ala Leu
50                  55                  60
```

METHODS OF IDENTIFYING A POLYPEPTIDE TARGET FOR DEGRADATION BY A MODULATOR OF CRBN

CROSS-REFERENCE TO RELATED APPLICATIONS

This application is the U.S. national phase application, pursuant to 35 U.S.C. § 371, of PCT international application Ser. No.: PCT/US2016/051035, filed Sep. 9, 2016, designating the United States and published in English, which claims the benefit of the following U.S. Provisional Application No. 62/258,929, filed Nov. 23, 2015 and 62/217,476, filed Sep. 11, 2015, the entire contents of which are incorporated herein by reference.

STATEMENT OF RIGHTS TO INVENTIONS MADE UNDER FEDERALLY SPONSORED RESEARCH

This invention was made with government support under Grant No. P01 CA066996 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy of the Sequence Listing, created on Sep. 29, 2016, is named 167741_011102PCT_SL.txt and is 74,577 bytes in size.

BACKGROUND OF THE INVENTION

The drug thalidomide became infamous in the early 1960s when its use during the first trimester of pregnancy was linked to profound birth defects, most commonly a malformation of the upper limbs known as phocomelia. The discovery of thalidomide's teratogenic property was a major setback for the compound. However, thalidomide was later repurposed and is currently an FDA-approved therapy for a number of disorders, including erythema nodosum leparum, 5q-myelodysplastic syndrome (MDS) and the plasma cell malignancy multiple myeloma. Thalidomide's success as a treatment for these disorders motivated the synthesis of lenalidomide and pomalidomide, more potent derivatives which have largely replaced thalidomide in the treatment of 5q-MDS and multiple myeloma. It is therefore important to identify additional potentially therapeutically relevant targets of thalidomide, lenalidomide, and pomalidomide to improve clinical use of these drugs. Further, it is important to detect resistance to these drugs in patients, particularly at an early stage of a disease, so that alternate forms of therapy can be provided.

SUMMARY OF THE INVENTION

As described below, the present invention features methods of identifying drug-modulated polypeptide targets for cereblon (CRBN)-mediated degradation, particularly lenalidomide- or lenalidomide analog-modulated substrates of CRBN. The present invention also features methods of characterizing and/or monitoring sensitivity of a subject to a modulator of CRBN.

In one aspect, the invention provides a method of identifying a cell resistant to a modulator of CRBN, the method comprising detecting the sequence of a region in a IKZF3 polynucleotide relative to a IKZF3 reference sequence, wherein the region encodes amino acids 146-168 of a IKZF3 polypeptide in the cell, and wherein detection of a mutation in the region indicates the cell is resistant to a modulator of CRBN.

In another aspect, the invention provides a method of characterizing the sensitivity of a subject to a modulator of CRBN, the method comprising detecting the sequence of a region in an IKZF3 polynucleotide in a biological sample obtained from the subject relative to a IKZF3 reference sequence, wherein the region encodes amino acids 146-168 of a IKZF3 polypeptide, and wherein detection of a mutation in the region is indicative of resistance to a modulator of CRBN and failure to detect a mutation is indicative of sensitivity to a modulator of CRBN.

In yet another aspect, the invention provides a method of monitoring sensitivity of a subject to a modulator of CRBN, the method comprising detecting the sequence of a region in an IKZF3 polynucleotide in a biological sample obtained from the subject relative to a IKZF3 reference sequence, wherein the region encodes amino acids 146-168 of a IKZF3 polypeptide, and wherein detection of a mutation in the region is indicative of resistance to a modulator of CRBN and failure to detect a mutation is indicative of sensitivity to a modulator of CRBN.

In still another aspect, the invention provides a method of monitoring sensitivity of a subject to a modulator of CRBN, the method comprising (a) administering to the subject an amount of lenalidomide or lenalidomide analog; and (b) detecting the sequence of a region in an IKZF3 polynucleotide in a biological sample obtained from the subject relative to a IKZF3 reference sequence, wherein the region encodes amino acids 146-168 of a IKZF3 polypeptide, and wherein detection of a mutation in the region is indicative of resistance to a modulator of CRBN and failure to detect a mutation is indicative of sensitivity to a modulator of CRBN.

In another aspect, the invention provides a method of selecting a subject for treatment with an alternative to a modulator of CRBN, the method comprising detecting the sequence of a region in an IKZF3 polynucleotide in a biological sample obtained from the subject relative to a IKZF3 reference sequence, wherein the region encodes amino acids 146-168 of a IKZF3 polypeptide, wherein a subject having a mutation in the region is selected for treatment with an alternative to a modulator of CRBN.

In various embodiments of any of the aspects delineated herein, the mutation is at amino acid position 147, 148, 151, 152, 153, 155, 161, 164, or 168. In various embodiments, the sequence of the region in the IKZF3 polynucleotide is detected by sequencing or probe hybridization.

In various embodiments of any of the aspects delineated herein, the subject has a B cell neoplasia or related condition. In various embodiments, the B cell neoplasia or related condition is a plasma cell malignancy multiple myeloma or a myelodysplastic syndrome. In various embodiments, the biological sample is blood.

In yet another aspect, the invention provides a kit comprising a reagent detecting the sequence of a polynucleotide encoding amino acids 146-168 of an IKZF3 polypeptide. In various embodiments, the reagent is a sequencing primer or hybridization probe.

In still another aspect, the invention provides a method of identifying increased degradation of a polypeptide in a cell when the cell is contacted with a modulator of CRBN, the method comprising detecting in a polypeptide a sequence substantially identical to a IKZF3 zinc finger comprising amino acids 146-168 of IKZF3, wherein presence of the sequence indicates increased degradation of the polypeptide when the cell is contacted with a modulator of CRBN.

In another aspect, the invention provides a method of identifying a drug-modulated polypeptide substrate of CRBN, the method comprising detecting a sequence substantially identical to an IKZF3 zinc finger comprising amino acids 146-168 of IKZF3 in a candidate polypeptide, wherein presence of the sequence indicates the candidate polypeptide is a drug-modulated polypeptide substrate of CRBN.

In yet another aspect, the invention provides a method of identifying a polypeptide target of a modulator of CRBN, the method comprising detecting a sequence substantially identical to an IKZF3 zinc finger comprising amino acids 146-168 of IKZF3 in a candidate polypeptide, wherein presence of the sequence indicates the candidate polypeptide is a polypeptide target of a modulator of CRBN.

In still another aspect, the invention provides a method of depleting a polypeptide in a cell, the method comprising contacting the cell with a modulator of CRBN, wherein the polypeptide is identified as having a sequence substantially identical to an IKZF3 zinc finger comprising amino acids 146-168 of IKZF3 in the polypeptide, thereby depleting the polypeptide in the cell.

In another aspect, the invention provides a method of depleting a polypeptide in a cell, the method comprising (a) fusing to the polypeptide a second polypeptide comprising a sequence substantially identical to a IKZF3 zinc finger comprising amino acids 146-168 of IKZF3; and (b) contacting the cell with a modulator of CRBN, thereby depleting the polypeptide in the cell.

In another aspect, the invention provides a method of identifying a drug-modulated polypeptide substrate of CRBN. The method contains the step of detecting a sequence substantially identical to a sequence of any one or more of the sequences of amino acids 146-168 of IKZF3, amino acids 149-172 of RNF166, amino acids 417-439 of ZNF692, and amino acids 400-422 of ZFP91, where presence of the sequence indicates the candidate polypeptide is a drug-modulated polypeptide substrate of CRBN.

In yet another aspect, the invention provides a method of identifying a drug-modulated polypeptide substrate of CRBN. The method contains the step of detecting a sequence substantially identical to any one or more of the sequences:

```
                              (SEQ ID NO: 1)
FQCNQCGASFTQKGNLLRHIKLH;

(SEQ ID NO: 2)
FACPYCGARNLDQQELVKHCVESH;

(SEQ ID NO: 3)
LQCEICGFTCRQKASLNWHQRKH;
and (SEQ ID NO: 4)
LQCEICGFTCRQKASLNWHMKKH;
``` where presence of the sequence indicates that the candidate polypeptide is a drug-modulated polypeptide substrate of CRBN.

In various embodiments of any of the aspects delineated herein, the sequence comprises a C2H2 zinc finger sequence. In various embodiments, the C2H2 zinc finger sequence corresponding to amino acids 147, 152, and 153 in the IKZF3 zinc finger comprise Gln, Gly, or Ala. In various embodiments of any of the aspects delineated herein, the polypeptide is IKZF3, IKZF1, CSNK1a1, RNF166, ZNF692, or ZFP91. In various embodiments, the increased degradation is mediated by CRBN.

In various embodiments, the drug is lenalidomide, thalidomide, or pomalidomide. In various embodiments, the polypeptide substrate or polypeptide target is degraded by CRBN-mediated degradation in a cell when the cell is contacted with a modulator of CRBN. In various embodiments of any of the aspects delineated herein, the polypeptide is depleted by CRBN-mediated degradation of the polypeptide. In various embodiments of any of the aspects delineated herein, the modulator of CRBN is lenalidomide, thalidomide, or pomalidomide.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression or activity levels, preferably a 25% change, more preferably a 40% change, and most preferably a 50% or greater change in expression or activity levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid. Lenalidomide analogs include, but are not limited to, thalidomide or pomalidomide.

By "biological sample" is meant any liquid, cell, or tissue obtained from a subject.

By "biomarker" or "marker" is meant any protein or polynucleotide having an alteration in expression level or activity that is associated with a disease or disorder.

By "B cell neoplasia" is meant any neoplasia arising from a B-cell progenitor or other cell of B cell lineage. In particular embodiments, a B cell neoplasia arises from a cell type undergoing B cell differentiation. In other embodiments, a B cell neoplasia includes plasma cells.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "CSNK1a1 polypeptide" or "casein kinase 1A1 polypeptide" is meant a polypeptide having at least about 85% or greater identity to Unit Pro Accession No. P48729-1 or P48729-2 (having a phosphor serine at position 156), or a fragment thereof, and having kinase activity. An exemplary CSNK1a1 polypeptide sequence is provided below (SEQ ID NO: 5).

```
            10         20         30         40
    MASSSGSKAE FIVGGKYKLV RKIGSGSFGD IYLAINITNG
            50         60         70         80
    EEVAVKLESQ KARHPQLLYE SKLYKILQGG VGIPHIRWYG
            90        100        110        120
    QEKDYNVLVM DLLGPSLEDL FNFCSRRFTM KTVLMLADQM
           130        140        150        160
    ISRIEYVHTK NFIHRDIKPD NFLMGIGRHC NKLFLIDFGL
           170        180        190        200
    AKKYRDNRTR QHIPYREDKN LTGTARYASI NAHLGIEQSR
           210        220        230        240
    RDDMESLGYV LMYFNRTSLP WQGLKAATKK QKYEKISEKK
           250        260        270        280
    MSTPVEVLCK GFPAEFAMYL NYCRGLRFEE APDYMYLRQL
           290        300        310        320
    FRILFRTLNH QYDYTFDWTM LKQKAAQQAA SSSGQGQQAQ
           330
    TPTGKQTDKT KSNMKGF
```

By "CSNK1a1 polynucleotide" or "casein kinase 1A1 polynucleotide" is meant a polynucleotide encoding a casein kinase 1A1 polypeptide. An exemplary CSNK1a1 polynucleotide sequence is provided at NCBI Accession No. NM_001025105. The sequence is provided below (SEQ ID NO: 6).

```
   1 atgcgcagct gggcggtgac agggtgacgc tcggagcgtg ggccgcgact ctcacggatc
  61 cggttccgcc ctctcgctgc cgatccttcg gagcgagcgc ccgagatccc tttcccagag
 121 tgctctgcgc cgtgaagaag cggctcccgg ggactggggg cattttgtgt tggctggagc
 181 tggagtaaca agatggcgtc gtccgcggag tgacaggggt ccctctgggc cggagccggc
 241 ggcagtggtg gcagcggtat cgccgcccta gctcaccgcg ccccttttcc agcccgcgac
 301 gtcgccgcgc aagcgaggca gcggcggccg ccgagaaaca agtggcccag cctggtaacc
 361 gccgagaagc ccttcacaaa ctgcggcctg caaaaagaa acctgactga gcggcggtga
 421 tcaggttccc ctctgctgat tctgggcccc gaacccggt aaaggcctcc gtgttccgtt
 481 tcctgccgcc ctcctccgta gccttgccta gtgtaggagc cccgaggcct ccgtcctctt
 541 cccagaggtg tcgggcttg gccccagcct ccatcttcgt ctctcaggat ggcgagtagc
 601 agcggctcca aggctgaatt cattgtcgga gggaaatata aactggtacg gaagatcggg
 661 tctggctcct tcggggacat ctatttggcg atcaacatca ccaacggcga ggaagtggca
 721 gtgaagctag aatctcagaa ggccaggcat ccccagttgc tgtacgagag caagctctat
 781 aagattcttc aaggtggggt tggcatcccc cacatacggt ggtatggtca ggaaaaagac
 841 tacaatgtac tagtcatgga tcttctggga cctagcctcg aagacctctt caatttctgt
 901 tcaagaaggt tcacaatgaa aactgtactt atgttagctg accagatgat cagtagaatt
 961 gaatatgtgc atacaaagaa ttttatacac agagacatta aaccagataa cttcctaatg
1021 ggtattgggc gtcactgtaa taagtgttta gaatctccag tggggaagag gaaaagaagc
1081 atgactgtta gtacttctca ggacccatct ttctcaggat taaaccagtt attccttatt
1141 gattttggtt tggccaaaaa gtacagagac aacaggacaa ggcaacacat accatacaga
1201 gaagataaaa acctcactgg cactgcccga tatgctagca tcaatgcaca tcttggtatt
1261 gagcagagtc gccagatgaa catgaatca ttaggatatg ttttgatgta ttttaataga
1321 accagcctgc catggcaagg gctaaaggct gcaacaaaga aacaaaaata tgaaaagatt
```

```
1381 agtgaaaaga agatgtccac gcctgttgaa gttttatgta aggggtttcc tgcagaattt 1441 gcgatgtact taaactattg tcgtgggcta cgctttgagg aagccccaga ttacatgtat 1501 ctgaggcagc tattccgcat tcttttcagg accctgaacc atcaatatga ctacacattt 1561 gattggacaa tgttaaagca gaaagcagca cagcaggcag cctcttccag tgggcagggt 1621 cagcaggccc aaaccccac aggcaagcaa actgacaaaa ccaagagtaa catgaaaggt 1681 ttctaagcat gaattgagga acagaagaag cagagcagat gatcggagca gcatttgttt 1741 ctccccaaat ctagaaattt tagttcatat gtacactagc cagtggttgt ggacaaccat 1801 ttacttggtg taaagaactt aatttcagta taaactgact ctgggcagca ttggtgatgc 1861 tgtatcctga gttgtagcct ctgtaattgt gaatattaac tgagatagtg aaacatggtg 1921 tccggttttc tattgcattt tttcaagtgg aaaagttaac taaatggttg acacacaaaa 1981 attggtggag aaattgtgca tatgccaatt ttttgttaaa accttttgtt ttgaactata 2041 ctgctttgag atctcatttc agaagaacg catgaacagt cttcagccac agttgtgatg 2101 gttgttaaat gctcacaatt gtgcattctt agggttttc catccctggg gtttgcaagt 2161 tgttcactta aaacattctt aaaatggttg gcttcttgtc tgcaagccag ctgatatggt 2221 agcaaccaaa gattccagtg tttgagcata tgaaagactc tgcctgctta attgtgctag 2281 aaataacagc atctaaagtg aagacttaag aaaaacttag tgactactag attatcctta 2341 ggactctgca ttaactctat aatgttcttg gtattaaaaa aaaagcatat ttgtcacaga 2401 aatttagtta acatcttaca actgaacatg tatgtatgtt gcttagataa atgtaatcac 2461 tgtaaacatc tatatgatct gggattttgt ttttattttg aaatgggagc ttttttgttt 2521 acaagttcat taaaaactaa aaactgtttc tgtaaggaaa tgagattttt tttaaacaac 2581 aaaaaatgcc ttgctgactc actattaaat aaaaatctcc ccaattttt gatagactac 2641 ttcaaaaaaa aaaaaaaaa a
```

By "C2H2 zinc finger sequence" or "C2H2 zinc finger motif" is meant a sequence of amino acids which typically includes two conserved cysteines and two conserved histidine residues. The two conserved cysteines and two conserved histidines co-ordinate a zinc ion, although other combinations of cysteine/histidine as the zinc-chelating residues are possible. For example, in IKZF3, the cysteines at positions 148 and 151 and histidines at positions 164 and 168 are indicative of a C2H2 zinc finger motif.

By "CRBN polypeptide" or "Cereblon" is meant a polypeptide or fragment thereof having at least 85% amino acid sequence identity to NCBI Accession No. AAH67811.1 or NP_001166953.1 and having IKZF3 binding activity. Exemplary CRBN polypeptide sequences are provided below:

```
AAH67811.1
                                                         (SEQ ID NO: 7)
  1 magegdqqda ahnmgnhlpl lpeseeedem evedqdskea kkpniinfdt slptshtylg 61 admeefhgrt lhdddscqvi pvlpqvmmil ipgqtlplql fhpqevsmvr nliqkdrtfa 121 vlaysnvqer eaqfgttaei yayreeqdfg ieivkvkaig rqrfkvlelr tqsdgiqqak 181 vqilpecvlp stmsavqles lnkcqifpsk pvsredqcsy kwwqkyqrrk fhcanltswp 241 rwlyslydae tlmdrikkql rewdenlkdd slpsnpidfs yrvaaclpid dvlriqllki 301 gsaiqrlrce ldimnkctsl cckqcqetei ttkneifsls lcgpmaayvn phgyvhetlt 361 vykacnlnli grpstehswf pgyawtvaqc kicashigwk ftatkkdmsp qkfwgltrsa 421 llptipdted eispdkvilc l NP_001166953.1
                                                         (SEQ ID NO: 8)
  1 magegdqqda ahnmgnhlpl lpeseeedem evedqdskea kkpniinfdt slptshtylg 61 admeefhgrt lhdddscqvi pvlpqvmmil ipgqtlplql fhpqevsmvr nliqkdrtfa
```

-continued

```
121 vlaysnvqer eaqfgttaei yayreeqdfg ieivkvkaig rqrfkvlelr tqsdgiqqak 181 vqilpecvlp stmsavqles lnkcqifpsk pvsredqcsy kwwqkyqkrk fhcanltswp 241 rwlyslydae tlmdrikkql rewdenlkdd slpsnpidfs yrvaaclpid dvlriqllki 301 gsaiqrlrce ldimnkctsl cckqcqetei ttkneifsls lcgpmaayvn phgyvhetlt 361 vykacnlnli grpstehswf pgyawtvaqc kicashigwk ftatkkdmsp qkfwgltrsa 421 llptipdted eispdkvilc l
```

By "CRBN polynucleotide" is meant a nucleic acid molecule encoding a CRBN polypeptide. An exemplary CRBN polynucleotide sequence is provided at NCBI Accession No. BC067811, which is reproduced below (SEQ ID NO: 9):

```
   1 gcgtgtaaac agacatggcc ggcgaaggag atcagcagga cgctgcgcac aacatgggca 61 accacctgcc gctcctgcct gagagtgagg aagaagatga aatggaagtt gaagaccagg 121 atagtaaaga agccaaaaaa ccaaacatca taaattttga caccagtctg ccgacatcac 181 atacatacct aggtgctgat atggaagaat ttcatggcag gactttgcac gatgacgaca 241 gctgtcaggt gattccagtt cttccacaag tgatgatgat cctgattccc ggacagacat 301 tacctcttca gcttttttcac cctcaagaag tcagtatggt gcggaattta attcagaaag 361 atagaaccct tgctgttctt gcatacagca atgtacagga aagggaagca cagtttggaa 421 caacagcaga gatatatgcc tatcgagaag aacaggattt tggaattgag atagtgaaag 481 tgaaagcaat tggaagacaa aggttcaaag tccttgagct aagaacacag tcagatggaa 541 tccagcaagc taaagtgcaa attcttcccg aatgtgtgtt gccttcaacc atgtctgcag 601 ttcaattaga atccctcaat aagtgccaga tatttcctcc aaaacctgtc tcaagagaag 661 accaatgttc atataaatgg tggcagaaat accagaggag aaagtttcat tgtgcaaatc 721 taacttcatg gcctcgctgg ctgtattcct tatatgatgc tgagacccta atggacagaa 781 tcaagaaaca gctacgtgaa tgggatgaaa atctaaaaga tgattctctt ccttcaaatc 841 caatagattt ttcttacaga gtagctgctt gtcttcctat tgatgatgta ttgagaattc 901 agctccttaa aattggcagt gctatccagc gacttcgctg tgaattagac attatgaata 961 aatgtacttc cctttgctgt aaacaatgtc aagaaacaga ataacaacc aaaaatgaaa 1021 tattcagttt atccttatgt gggccgatgg cagcttatgt gaatcctcat ggatatgtgc 1081 atgagacact tactgtgtat aaggcttgca acttgaatct gataggccgg ccttctacag 1141 aacacagctg gtttcctggg tatgcctgga ctgttgccca gtgtaagatc tgtgcaagcc 1201 atattggatg gaagtttacg gccaccaaaa agacatgtc acctcaaaaa ttttggggct 1261 taacgcgatc tgctctgttg cccacgatcc cagacactga agatgaaata gtccagaca 1321 aagtaatact ttgcttgtaa acagatgtga tagagataaa gttagttatc taacaaattg 1381 gttatattct aagatctgct ttggaaatta ttgcctctga tacataccta agtaaacata 1441 acattaatac ctaagtaaac ataacattac ttggagggtt gcagtttcta agtgaaactg 1501 tatttgaaac ttttaagtat actttaggaa acaagcatga acggcagtct agaataccag 1561 aaacatctac ttgggtagct tggtgccatt atcctgtgga atctgatatg tctggtagcg 1621 tgtcattgat gggacatgaa gacatctttg gaaatgatga gattatttcc tgtgttaaaa 1681 aaaaaaaaaa aatcttaaat tcctacaatg tgaaactgaa actaataatt tgatcctgat 1741 gtatgggaca gcgtatctgt accagtgctc taaataacaa aagctagggt gacaagtaca
```

```
1801 tgttcctttt ggaaagaagc aaggcaatgt atattaatta ttctaaaagg gctttgttcc 1861 tttccatttt ctttaacttc tctgagatac tgatttgtaa attttgaaaa ttagttaaaa 1921 tatgcagttt tttgagccca cgaatagttg tcatttcctt tatgtgcctg ttagtaaaaa 1981 gtagtattgt gtatttgctc agtatctgaa ctataagccc atttatactg ttccatacaa 2041 aagctatttt tcaaaaatta atttgaacca aaactactac tatagggaaa agatgccaaa 2101 acatgtcccc tcacccaggc taaacttgat actgtattat tttgttcaat gtaaattgaa 2161 gaaaatctgt aagtaagtaa accttaagtg tgaaactaaa aaaaaaaaaa aaa
```

As used herein, a "degron" or "degron sequence" refers to an amino acid sequence in a polypeptide that is both necessary and sufficient for targeting by the polypeptide's cognate ubiquitin ligase. In one embodiment, the degron of the IKZF3 polypeptide is amino acids 146-168 of IKZF3.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases, include B cell neoplasia or other malignancies, for example, plasma cell malignancy, multiple myeloma or a myelodysplastic syndrome, erythema nodosum leparum, 5q-myelodysplastic syndrome.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "IKZF1 polypeptide" or "Ikaros" is meant a polypeptide having at least about 85% amino acid sequence identity to a sequence provided at NCBI Accession No. AAH18349, NP_006051, NP_001207694, or a fragment thereof and having DNA binding or transcriptional regulatory activity.

For IKZF1 Isoform 1, the degron is from 130-270. For IKZF1 Isoform 2, the degron is from amino acid 136-180/236-249. Both isoforms are responsive to lenalidomide. Exemplary amino acid sequences for the two isoforms are provided below:

```
IKZF1 isoform 2 NCBI Reference No. NP_001207694
                                                  (SEQ ID NO: 10)
   1 mdadegqdms qvsgkesppv sdtpdegdep mpipedlstt sggqqssksd rvvasnvkve 61 tqsdeengra cemngeecae dlrmldasge kmngshrdqg ssalsgvggi rlpngklkcd 121 icgiicigpn vlmvhkrsht gerpfqcnqc gasftqkgnl lrhiklhsge kpfkchlcny 181 acrrrdaltg hlrthsvike etnhsemaed lckigsersl vldrlasnva krkssmpqkf 241 lgdkglsdtp ydssasyeke nemmkshvmd qainnainyl gaeslrplvq tppggsevvp 301 vispmyqlhk plaegtprsn hsaqdsaven llllskaklv psereaspsn scqdstdtes 361 nneeqrsgli yltnhiapha rnglslkeeh raydllraas ensqdalrvv stsgeqmkvy 421 kcehcrvlfl dhvmytihmg chgfrdpfec nmcgyhsqdr yefsshitrg ehrfhms IKZF1 isoform 1 NCBI Reference No. NP_006051
                                                  (SEQ ID NO: 11)
   1 mdadegqdms qvsgkesppv sdtpdegdep mpipedlstt sggqqssksd rvvasnvkve 61 tqsdeengra cemngeecae dlrmldasge kmngshrdqg ssalsgvggi rlpngklkcd 121 icgiicigpn vlmvhkrsht gerpfqcnqc gasftqkgnl lrhiklhsge kpfkchlcny 181 acrrrdaltg hlrthsvgkp hkcgycgrsy kqrssleehk erchnylesm glpgtlypvi 241 keetnhsema edlckigser slvldrlasn vakrkssmpq kflgdkglsd tpydssasye
```

```
301 kenemmkshv mdqainnain ylgaeslrpl vqtppggsev vpvispmyql hkplaegtpr 361 snhsaqdsav enllllskak lvpsereasp snscqdstdt esnneeqrsg liyltnhiap 421 harnglslke ehraydllra asensqdalr vvstsgeqmk vykcehcrvl fldhvmytih 481 mgchgfrdpf ecnmcgyhsq dryefsshit rgehrfhms
```

By "IKZF1 polynucleotide" is meant a polynucleotide encoding an IKZF1 polypeptide. An exemplary IKZF1 polynucleotide is provided at NM_006060.4 and reproduced below (SEQ ID NO: 12):

```
   1 ggcagcagag gaacctttg gaggaggaag aggacacaga ggccctgtag ccaggcacca
  61 agatccctcc caggtggctg ggtctgaggg gaactccgag cagccctagg tcctcaaagt
 121 ctggatttgt gtggaaaagg cagctctcac ttggccttgg cgaggcctcg gttggttgat
 181 aacctgagga ccatggatgc tgatgagggt caagacatgt cccaagtttc agggaaggaa
 241 agccccctg taagcgatac tccagatgag ggcgatgagc ccatgccgat ccccgaggac
 301 ctctccacca cctcgggagg acagcaaagc tccaagagtg acagagtcgt ggccagtaat
 361 gttaaagtag agactcagag tgatgaagag aatgggcgtg cctgtgaaat gaatgggaa
 421 gaatgtgcgg aggatttacg aatgcttgat gcctcgggag agaaaatgaa tggctcccac
 481 agggaccaag gcagctcggc tttgtcggga gttggaggca ttcgacttcc taacggaaaa
 541 ctaaagtgtg atatctgtgg gatcatttgc atcgggccca atgtgctcat ggttcacaaa
 601 agaagccaca ctggagaacg gcccttccag tgcaatcagt gcggggcctc attcacccag
 661 aagggcaacc tgctccggca catcaagctg cattccgggg agaagccctt caatgccac
 721 ctctgcaact acgcctgccg ccggagggac gccctcactg ccacctgag gacgcactcc
 781 gtcattaaag aagaaactaa tcacagtgaa atggcagaag acctgtgcaa gataggatca
 841 gagagatctc tcgtgctgga cagactagca agtaacgtcg ccaaacgtaa gagctctatg
 901 cctcagaaat ttcttgggga caagggcctg tccgacacgc cctacgacag cagcgccagc
 961 tacgagaagg agaacgaaat gatgaagtcc cacgtgatgg accaagccat caacaacgcc
1021 atcaactacc tgggggccga gtccctgcgc ccgctggtgc agacgccccc gggcggttcc
1081 gaggtggtcc cggtcatcag cccgatgtac cagctgcaca gccgctcgc ggagggcacc
1141 ccgcgctcca accactcggc ccaggacagc gccgtggaga acctgctgct gctctccaag
1201 gccaagttgg tgccctcgga gcgcgaggcg tccccgagca cagctgcca agactccacg
1261 gacaccgaga gcaacaacga ggagcagcgc agcggtctca tctacctgac caaccacatc
1321 gccccgcacg cgcgcaacgg gctgtcgctc aaggaggagc accgcgccta cgacctgctg
1381 cgcgccgcct ccgagaactc gcaggacgcg ctccgcgtgg tcagcaccag cggggagcag
1441 atgaaggtgt acaagtgcga acactgccgg gtgctcttcc tggatcacgt catgtacacc
1501 atccacatgg gctgccacgg cttccgtgat ccttttgagt gcaacatgtg cggctaccac
1561 agccaggacc ggtacgagtt ctcgtcgcac ataacgcgag gggagcaccg cttccacatg
1621 agctaaagcc ctcccgcgcc cccaccccag accccgagcc accccaggaa aagcacaagg
1681 actgccgcct tctcgctccc gccagcagca tagactggac tggaccagac aatgttgtgt
1741 ttggatttgt aactgttttt tgttttttgt ttgagttggt tgattggggt ttgatttgct
1801 tttgaaaaga tttttatttt tagaggcagg gctgcattgg gagcatccag aactgctacc
1861 ttcctagatg tttccccaga ccgctggctg agattccctc acctgtcgct tcctagaatc
1921 ccccttctcca aacgattagt ctaaattttc agagagaaat agataaaaca cgccacagcc
```

-continued

```
1981 tgggaaggag cgtgctctac cctgtgctaa gcacggggtt cgcgcaccag gtgtctttt
2041 ccagtcccca gaagcagaga gcacagcccc tgctgtgtgg gtctgcaggt gagcagacag
2101 gacaggtgtg ccgccaccca agtgccaaga cacagcaggg ccaacaacct gtgcccaggc
2161 cagcttcgag ctacatgcat ctagggcgga gaggctgcac ttgtgagaga aaatactatt
2221 tcaagtcata ttctgcgtag gaaaatgaat tggttgggga aagtcgtgtc tgtcagactg
2281 ccctgggtgg agggagacgc cgggctagag ccttgggat cgtcctggat tcactggctt
2341 tgcggaggct gctcagatgg cctgagcctc ccgaggcttg ctgccccgta ggaggagact
2401 gtcttcccgt gggcatatct ggggagccct gttccccgct ttttcactcc cataccttta
2461 atggccccca aaatctgtca ctacaattta aacaccagtc ccgaaatttg gatcttcttt
2521 cttttttgaat ctctcaaacg gcaacattcc tcagaaacca aagctttatt tcaaatctct
2581 tccttccctg gctggttcca tctagtacca gaggcctctt ttcctgaaga aatccaatcc
2641 tagccctcat tttaattatg tacatctgtt tgtagccaca agcctgaatt tctcagtgtt
2701 ggtaagtttc tttacctacc ctcactatat attattctcg ttttaaaacc cataaaggag
2761 tgatttagaa cagtcattaa ttttcaactc aatgaaatat gtgaagccca gcatctctgt
2821 tgctaacaca cagagctcac ctgtttgaaa ccaagctttc aaacatgttg aagctcttta
2881 ctgtaaaggc aagccagcat gtgtgtccac acatacatag gatggctggc tctgcacctg
2941 taggatattg gaatgcacag gcaattgag ggactgagcc agaccttcgg agagtaatgc
3001 caccagatcc cctaggaaag aggaggcaaa tggcactgca ggtgagaacc ccgcccatcc
3061 gtgctatgac atggaggcac tgaagcccga ggaaggtgtg tggagattct aatcccaaca
3121 agcaagggtc tccttcaaga ttaatgctat caatcattaa ggtcattact ctcaaccacc
3181 taggcaatga agaatatacc atttcaaata tttacagtac ttgtcttcac caacactgtc
3241 ccaaggtgaa atgaagcaac agagaggaaa ttgtacataa gtacctcagc atttaatcca
3301 aacagggggtt cttagtctca gcactatgac attttgggct gactacttat ttgttaggca
3361 ggagctctcc tgtgcattgt aggataatta gcagtatccc tggtggctac ccaatagacg
3421 ccagtagcac cccgaattga caacccaaac tctccagaca tcaccaactg tcccctgcga
3481 ggagaaatca ctcctggggg agaaccactg acccaaatga attctaaacc aatcaaatgt
3541 ctgggaagcc ctccaagaaa aaaaaaaaa aa
```

By "IKZF3 polypeptide" or "Aiolos" is meant a polypeptide having at least about 85% amino acid sequence identity to NCBI Accession No. NP_036613.2 (UnitPro Identifier No. Q9UKT9-1) or a fragment thereof and having DNA binding or transcriptional regulatory activity. An exemplary amino acid sequence of IKZF3 is provided below (SEQ ID NO: 13).

```
          10         20         30         40
  MEDIQTNAEL KSTQEQSVPA ESAAVLNDYS LTKSHEMENV 50         60         70         80
  DSGEGPANED EDIGDDSMKV KDEYSERDEN VLKSEPMGNA 90        100        110        120
  EEPEIPYSYS REYNEYENIK LERHVVSFDS SRPTSGKMNC 130        140        150        160
  DVCGLSCISF NVLMVHKRSH TGERPFQCNQ CGASFTQKGN 170        180        190        200
  LLRHIKLHTG EKPFKCHLCN YACQRRDALT GHLRTHSVEK 210        220        230        240
  PYKCEFCGRS YKQRSSLEEH KERCRTFLQS TDPGDTASAE 250        260        270        280
  ARHIKAEMGS ERALVLDRLA SNVAKRKSSM PQKFIGEKRH 290        300        310        320
  CFDVNYNSSY MYEKESELIQ TRMMDQAINN AISYLGAEAL 330        340        350        360
  RPLVQTPPAP TSEMVPVISS MYPIALTRAE MSNGAPQELE 370        380        390        400
  KKSIHLPEKS VPSERGLSPN NSGHDSTDTD SNHEERQNHI 410        420        430        440
  YQQNHMVLSR ARNGMPLLKE VPRSYELLKP PPICPRDSVK 450        460        470        480
  VINKEGEVMD VYRCDHCRVL FLDYVMFTIH MGCHGFRDPF 490        500
  ECNMCGYRSH DRYEFSSHIA RGEHRALLK
```

By "IKZF3 polynucleotide" or "Aiolos polynucleotide" is meant a nucleic acid sequence encoding an IKZF3 polypeptide. An exemplary polynucleotide sequence is provided at NCBI Accession No. NM_012481, which is reproduced below (SEQ ID NO: 14):

```
   1 gcaggagcac gtggagaggc cgagtagcca cagcggcagc tccagcccgg cccggcagcg
  61 acatggaaga tatacaaaca aatgcggaac tgaaaagcac tcaggagcag tctgtgcccg
 121 cagaaagtgc agcggttttg aatgactaca gtttaaccaa atctcatgaa atggaaaatg
 181 tggacagtgg agaaggccca gccaatgaag atgaagacat aggagatgat tcaatgaaag
 241 tgaaagatga atacagtgaa agagatgaga atgtttttaaa gtcagaaccc atgggaaatg
 301 cagaagagcc tgaaatccct tacagctatt caagagaata taatgaatat gaaaacatta
 361 agttggagag acatgttgtc tcattcgata gtagcaggcc aaccagtgga agatgaact
 421 gcgatgtgtg tggattatcc tgcatcagct tcaatgtctt aatggttcat aagcgaagcc
 481 atactggtga acgcccattc cagtgtaatc agtgtgggc atcttttact cagaaaggta
 541 acctcctccg ccacattaaa ctgcacacag ggaaaaacc tttttaagtgt cacctctgca
 601 actatgcatg ccaaagaaga gatgcgctca cggggcatct taggacacat tctgtggaga
 661 aaccctacaa atgtgagttt tgtggaagga gttacaagca gagaagttcc cttgaggagc
 721 acaaggagcg ctgccgtaca tttcttcaga gcactgaccc aggggacact gcaagtgcgg
 781 aggcaagaca catcaaagca gagatgggaa gtgaaagagc tctcgtactg gacagattag
 841 caagcaatgt ggcaaaacga aaaagctcaa tgcctcagaa attcattggt gagaagcgcc
 901 actgctttga tgtcaactat aattcaagtt acatgtatga gaaagagagt gagctcatac
 961 agacccgcat gatggaccaa gccatcaata cgccatcag ctatcttggc gccgaagccc
1021 tgcgcccctt ggtccagaca ccgcctgctc ccacctcgga gatggttcca gttatcagca
1081 gcatgtatcc catagccctc acccgggctg agatgtcaaa cggtgcccct caagagctgg
1141 aaaagaaaag catccaccct tccagagaaga gcgtgccttc tgagagaggc ctctctccca
1201 acaatagtgg ccacgactcc acggacactg acagcaacca tgaagaacgc cagaatcaca
1261 tctatcagca aaatcacatg gtcctgtctc gggcccgcaa tgggatgcca cttctgaagg
1321 aggttccccg ctcttacgaa ctcctcaagc ccccgcccat ctgcccaaga gactccgtca
1381 aagtgatcaa caaggaaggg gaggtgatgg atgtgtatcg gtgtgaccac tgccgcgtcc
1441 tcttcctgga ctatgtgatg ttcacgattc acatgggctg ccacggcttc cgtgacccctt
1501 tcgagtgtaa catgtgtgga tatcgaagcc atgatcggta tgagttctcg tctcacatag
1561 ccagaggaga acacagagcc ctgctgaagt gaatatctgg tctcagggat tgctcctatg
1621 tattcagcat cgtttctaaa aaccaatgac ctcgcctaac agattgctct caaaacatac
1681 tcagttccaa acttcttttc ataccatttt tagctgtgtt cacaggggta gccagggaaa
1741 cactgtcttc cttcagaaat tattcgcagg tctagcatat tattactttt gtgaaaccctt
1801 tgttttccca tcagggactt gaattttatg gaatttaaaa gccaaaaagg tatttggtca
1861 ttatcttcta cagcagtgga atgagtggtc ccggagatgt gctatatgaa acattctttc
1921 tgagatatat caaccacacg tggaaaagcc tttcagtcat acatgcaaat ccacaaagag
1981 gaagagctga ccagctgacc ttgctgggaa gcctcaccct tctgcccttc acaggctgaa
2041 gggttaagat ctaatctccc taatctaaat gacagtctaa gagtaagtaa aagaacagcc
2101 ataaaataag tatctgttac gagtaactga agacccatt ctccaagcat cagatccatt
2161 tcctatcaca acatttttaa aaaatgtcat ctgatggcac ttctgcttct gtcctttacc
```

-continued

```
2221 ttcccatctc cagtgaaaag ctgagctgct tgggctaaa ccagttgtct atagaagaaa
2281 atctatgcca gaagaactca tggttttaaa tatagaccat catcgaaact ccagaaattt
2341 atccactgtg gatgatgaca tcgctttcct ttggtcaagg ttggcagagc aagggtataa
2401 aggggggaaat tgtttggcag caccaacaga aaacaaacaa acaaaaaaca gctacctaaa
2461 acttcttgaa agagttcatg gagaattggt gatacagacc caaagcaaat ttgccaatga
2521 tattttccac aaaaaaagtc caaaaagtat ggctcagcct cccccctccccc acaggagagg
2581 aattggagat agatggcatg tgtgtttaga tcggagttga gctccggaat ggggtgagga
2641 gggacacctc tattgagagg ttctccttga tcaggcaggc ttcggccctt ttttcccat
2701 ttaaatggaa ctgctgtatt ccatgaaaat tcctgaaagt ctgatcacgg ttctgcagat
2761 gtataagtca tccttgtcac tcataatatg tacatactat caggaggagt gctgttatca
2821 tggtaaaatt agcactggaa taggaggtca caaaatgctg gctaattagc tatgtgactt
2881 tgagaaatcg tttaactttt tttttttttt tttttttgag acaggatctc actctgttgc
2941 ccaggctgga gtgcagtggt gcaatcatgg ctcagtgcag cctcgacctc ccaggctca
3001 ggtgatcctc ccacctcagc ctcttgagta ctgggacaac aagtgcacac caccatgtct
3061 ggctacattt tgttcttttt gtagagatag gggtctcact atgttcccca tgctggtctt
3121 gaactcctgg gctcaagcaa tcagcccgcc tcagcctcct aaagtgctgg gattacaggt
3181 gtgagccacc acacccagcc ttatttaact cttaaaactc agtttccggc caggctcggt
3241 ggctcacacc tgtaatccca acactttggg aagccgaggc aggcgcatca tttgaggtca
3301 ggagttcgag accagcctga cccacatggt gaaaccctgt ctctactaaa aatacaaaaa
3361 ttagctgggc agtagtggca catgcctgta atcccagcta ctccggaggc tgaggcagaa
3421 aaatcgctta agcctgggag gttgaggttg cggtgagtgg agatcacact actgcactcc
3481 agtctgggcg acagagtgag accctgtctc aaacaaaaca aacaaaaac aaacaaacaa
3541 aaacaaaaaa aactcagttt cctcatccat aaaataggaa ttagatttca atgttctctt
3601 aggtcccttc tagctttaat tcatatgtga ttatgcagta accacaaggt atttttaaa
3661 cctcctaatg tatggatatt aagcagaaga gtatttatat gaatacatgt ttcacattcc
3721 tttggtatga aaatggtgtg ttaagttttt cctttaacca ctgagttgtg aatgtgaaga
3781 aggtggtgga gaggaacaaa aaacagaaag gtattttgat cttgccacaa agcatacaca
3841 caaattggca catgcagctg tttgccaaag ccttctttt tttttactt tttaagaaat
3901 tatgttaggg aaaataaatt ctgcttccag ggacaacttc atggagccta tttacaaatt
3961 aagagtcagc ttaatttgta acatttctac cagagccaag aatcccaaat tcctggtaga
4021 ttagtgtttt atttctaagg ggcttatgca ttcggctcca actcaactcg tctatgtgct
4081 gccagtaatt aaaatgttcc acctcagact gcacaaatgg cttatccttc tttgtggcat
4141 ggcgtctgtc tcaggaaaaa aggttttatg aaattccatg gcaacagtcc caacatgttt
4201 gagacttcag ctaaaggaat ggatgtattt tggtgtgtag tcttcagtat atcactgtat
4261 ttccgtaata ctagactcca agctatgcca gattgcttat tcccttttgtg aaagaggagt
4321 tgctcattac gttcttgaaa tatcgcacat cctgttggtt cttcaaggga caagagaaag
4381 agaatttgga agcagggatt agtagaagag aaaacgaggg aaggaagcc tttccaccag
4441 attagtgttc aagtctttgc agaggagacc aactttttt gttttctttt gttttgagac
4501 agtctctcgc tctgttgccc aggctggagt gcagtggcgc gatctcggct cacggcaacc
4561 tccgcctccc gggttcaagc aattctcctg cctcagcctc ccaagtagct gggattacag
4621 gtgctcacca ccaagcccgg ctaattttg tattttagt agagacaagg tttcaccatg
```

-continued

```
4681 ttggccaggc cagtctcaaa ctcctgacct caggtgatct gcccgccttg gcctcccaca
4741 gtgctgggat tacaggcatg agctaccgca cccagcctga gaccaccttt tgcatctcaa
4801 gattgtgaaa ccaaggccca ttccaccagc ctggggactc ttttttataga tatgatcctc
4861 cttttcctg tgactaatga atttgctgca tgatttctat tcttctgagg ttagttttct
4921 gagtaaggtg accactcaca aaggcacttt ctttgtggca ttctgagcct agattggggc
4981 ccatcaattc cagaaaaaat ttatgtgtgg aaactctgca tccttaagtc ttgaagttga
5041 accagatatg cagtggttac catcacacag ataaacgctg ccttctgtac atacccctta
5101 tgctgtacta attaacaaac cccttgccag ggctggggag gtgagggtga aggagaatct
5161 tagcagaagg gcagagtcag gacttgcatc tgccactgct gggcactgaa gccctggagc
5221 agcttcagat agtacctgta ctttctcatg cagactccct ctgaacaaga gccttgtagg
5281 cccctctcct tcatttccca ccagcctctt atcaggcggg ctttccacca tacacccagg
5341 aggccacggt ctgaggaaca accaaaccca tgcaaagggc cgggcgcgat agctcacgcc
5401 tgtaatgcca gcactttggg aggctggggc aggcagatca cctgaggttg ggagttcgag
5461 acctgcctga ccaacatgga gaaccccca tctctactaa aaatacaaaa ttagccgggc
5521 gtgatggcac atgcctgtaa tcccagctac tcaggaggct gaggcaggag aatcgcttga
5581 acccgggagg cggaggttgc ggtgagccga gatggcacca ctgcactcca gcctcggcaa
5641 caagagcgaa actctgtcta aacaaaaac aaacaaacaa acaaaaaac ccaggcaaag
5701 tttccttgca gccaaggtga cagaactggg ctgagggtgg aaaagaaaca gaaccagtgc
5761 tccaggtgtt ttttaatttt ttaatttatt tttatttttt ttgtatatgt atatatatgt
5821 atgtatattt tagaggacca gggtctcact atgttgccta ggccagactc aaactcctgt
5881 gctcaagcaa tcctgcctca gcctcccaag tagctgggat tacaggcatg cacaaacaat
5941 gcccagctct ccaaatgttt tctgtcacta cctgaagtgt tgcatcggta cttcctacgg
6001 aaagaaaact aaatagaagt gtctctcccg tgagccccca ccactaccac cagaaaaaaa
6061 aaagagagaa aatgaactca tcagtctta gtttcctcaa gttattctcc caaaagaca
6121 ttcgccttgg cacagataag ccagctaatc ttatgctttta tgacccactg tgagctgttc
6181 ctgacacagc ttctgacttt gtcagtgaca aaatttctca ccttttaaat gcagtgctta
6241 acattttgtt aggcccatac tcaaaatcgg ccagatataa aatgacctca gattttgatc
6301 tcctaggctc aaacaatcct cctacctcag cctcccaagt agctgggact ataggcacac
6361 caccatgcac agctaatttt ttttgtattt ttctgcagag atggcgtttc gccatactgc
6421 ccaggctagt ctcaaaatcc tgggctcaag caatctgccc acctcagcct cccaaagtgc
6481 tggaactaca ggcaagagcc actgcgccca gccacaacct cagatttctt tggcaaacag
6541 aaatgtttaa aaacacaaaa ttttgctcag gtgaaacact gtgttactat caaatctcac
6601 atccacataa agttttttctt ttcggctttg tttcgtgagg aacagacaga acaaagtttt
6661 tccaggtagc atctgtatca ctattattct cctatttcct gtaccacccc cacctcccca
6721 agccctactg aatgtgaggt ttagaatgtt ttaaggaggg tcaggtgcgg tggctcacgc
6781 ctgtaatccc agcactttgg gaggccaagg cgggcggatc acctgagttt gggagttcga
6841 gaccagcctg accaacatgg agaaccctg tctctactaa aaatacaaaa ttagccaggc
6901 gtggtggcac atgcctgtaa tcccagctac ttaggaggct gaggcaggag aatcgcttga
6961 acccaggagg aggaggttgt ggtgagccga gatcgtgcca ttgcactcca gcctgggtga
7021 cagagtgaga ctccatctcg aaaaaaaaaa tacaaaaatt agctgggtgt ggtggtgcac
```

```
7081  acctgtaatc ccagctactc gggaggctga cgcaggagaa ttgcttgaac ctgggaggtg
7141  gaggttgcag tgagccgaga tcgcgccatt gcaatccagc ctggacaaca gagtgagact
7201  ccatctcaaa aaaaaaaaaa aaagaatgt tttaaggaaa aaaatagtac tgttacatat
7261  aatcccaggt gataagacca caatggaaat gtttaagtcc tcactttaaa gagtacccca
7321  ctgagaagag gtatgttgga ctctagcaga gatttggaaa ctctgggaca ctcaagatgt
7381  gaaagagcct ggctatctga ggactcaaag agtcagcatc gggacttgtg agctcaagaa
7441  gagaaagggg agtggtgaaa ctttgtccta aaagttagca ccaggaacag aagaaaaaaa
7501  cccgatatat agtgatacct catcttttag agaatgggaa gctattttg tgttcacaca
7561  gaaagtatag ttcaaaaaac ctctatatcc agagttcaga caaggagaat gatttgagat
7621  ataagtgccg atgaaggagg tcaattttga tctgaaacca gcagctggac ctgggccacc
7681  tcaggaaaag gactctgttc tccaaggcag cacgactgaa tggttctgag aataagccag
7741  ggttcaggac tcctgaccct ttaggaccat ggactcagaa gagcctgaag gacaattgtg
7801  ggctttaaac ttctgagagc ttgtaaagta acacaagact gtgcctctcc cttgccccag
7861  ctgtagatag tctttgcccc accattgtta tgaagataca cagggttttg cagtttgaat
7921  aaattggata caagtttcct ctttttttt tctttttga gacaaagtct cgctctgttt
7981  ccccaggctg agtgcagtgg cacaatcaag gcttacttgc cgcctcaacc tcctgggctc
8041  aagcaacgag ccatcctccc gtcttagcct cccaactagc tgagactaca ggcgtgggtc
8101  accacaccca gctaattttt gtacttttg tagagacagg gtctcaccat gttgcccagg
8161  ctggtcctga actcctgggc tcaagtaatc tgcccacctc agcctcccaa agtgttgggg
8221  ttacaggcgt gaggcaccgc ggctggcctg agtttcttct taatactgta tcacaattgt
8281  gggctgtctt atgtgttgat atcgattgag ctatttgaaa taggaatgtt aatgggtgta
8341  ttaaattttt gtaaggatat aacaatatct accttccaag gatgttgtga ggttttccat
8401  gattttgtat atgagctaat gttacctttg aggggtggtg tgcattatgt tggatgattg
8461  taaattttca gtggaaaatg taccgtgtcc taaatttaaa gacatgaaaa atatcccaag
8521  atcatactag atcataatag caattccttt acaaatgaat tatggaggta actgatctct
8581  aacagtttcc ttcatgttgt tttaatgcac aagggcagag gatctgctga cccttggaac
8641  cagcgtgagc taaccacgtg ctatagacac ttcatggtgt cgcacccagg gaagtcaaag
8701  cgctttgctc cctcactgtc tgtgagtcct cagccattag taccccaccc ccgctgctc
8761  caaaacttga gttatttcaa atgtttctca ctgttcatct ctccactgac cccactccag
8821  aaagcctgga gagagtccca agatgccacc caccttcccc aatccctcgc cacagatctg
8881  tgtctatctc acactctgta agtgccgctt tgcttcttcc tctcttgaaa agactgagaa
8941  cacacatttt aacatgttag gaaaatgggg cagcctaaaa aatgactgat cccaccgcca
9001  gtgactcatg tatactccag gctagcagac aaggcccttt ttggtgggcc tgcttctgtg
9061  ggttcacaga aaccaaatta ctgtgggttg caaagaatta gcaggtcatt tacaaagcag
9121  acatcccttc acccagactg tggttttgca tgctcaggtt ctcagtctat gagctttggt
9181  gcaggatcat tttggctact ggaaaaacca tagcttattt taaatttctg gttgccaaag
9241  ccaccacacg tgtggtctgt ggatgaccat tgtctgcaga atgacgagga aggaacagaa
9301  tgtggtttgg ggctcagggt ggccttccca ctggagggaa aggcgggagg gagcccttgc
9361  cctgggtttt gacacagcct gtgctcacag cctctcctct catctgcatt tctcagaaat
9421  gccctccctg cccagtggtg actttccctc gtcactccta tggagttcta cctggagccc
9481  agccatgtgt ggaactgtga agtttactcc tctgtaaaga tggtttaaag aaagtcagct
```

```
9541 tctgaaatgt aacaatgcta acccttgctg gaaccctgta agaaatagcc ctgctgatag 9601 ttttctaggt ttatcatgtt tgatttttac actgaaaaat aaaaaaatcc tggtatgttt 9661 gaaattaaaa aaaaaaaaaa aaaaaa
```

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "sensitivity to a modulator of CRBN" is meant that at least one symptom of a disease or condition is ameliorated by treatment with a modulator of CRBN.

By "resistant to a modulator of CRBN" is meant that a cell having a disease has acquired an alteration that allows it to escape an anti-disease effect of at least one modulator of CRBN. For example, a resistant cell may be a neoplastic cell that has acquired an alteration that allows it to escape an anti-neoplastic effect of the modulator of CRBN. Exemplary anti-neoplastic effects include, but are not limited to, any effect that reduces proliferation, reduces survival, and/or increases cell death (e.g., increases apoptosis).

By "lenalidomide sensitivity" is meant that at least one symptom of a disease or condition is ameliorated by treatment with lenalidomide. Likewise, by "lenalidomide analog sensitivity" is meant at least one symptom of a disease or condition is ameliorated by treatment with a lenalidomide analog.

By "lenalidomide resistant" is meant that a cell having a disease has acquired an alteration that allows it to escape an anti-disease effect of lenalidomide. Likewise, by "lenalidomide analog resistant" is meant that a cell having a disease has acquired an alteration that allows it to escape an anti-disease effect of a lenalidomide analog. For example, a lenalidomide resistant cell may be a neoplastic cell that has acquired an alteration that allows it to escape an anti-neoplastic effect of lenalidomide. Exemplary anti-neoplastic effects include, but are not limited to, any effect that reduces proliferation, reduces survival, and/or increases cell death (e.g., increases apoptosis).

By "modulator of CRBN" or "modulator of Cereblon" is meant any agent which binds Cereblon (CRBN) and alters an activity of CRBN. In some embodiments, an activity of CRBN includes binding with and/or mediating degradation of Ikaros (IKZF1), Aiolos (IKZF3), or Casein kinase 1 Alpha (CSNK1a1). Thus, a modulator of CRBN includes agents that alter binding of CRBN with IKZF1, IKZF3, or CSNK1a1 and agents that alter CRBN's mediation of IKZF1, IKZF3, or CSNK1a1 degradation. In particular embodiments, a modulator of CRBN is lenalidomide or an analog thereof (e.g., pomalidomide or thalidomide).

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduces" is meant a negative alteration of at least 10%, 25%, 50%, 75%, or 100%.

By "reference" is meant a standard or controlled condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "RNF166 polypeptide" is meant a polypeptide or fragment thereof having at least 85% amino acid sequence identity to NCBI Accession Nos. NP_849163, NP_001165286, or NP_001165287 (various isoforms) and having a C2H2 zinc finger targeted by lenalidomide or a lenalidomide analog. An exemplary RNF166 polypeptide sequence provided at NCBI Accession No. NP_849163 is provided below (SEQ ID NO: 15):

```
  1 mamfrslvas aqqrqppagp aggdsgleaq ytcpiclevy hrpvaigscg htfcgeclqp
 61 clqvpsplcp lcrlpfdpkk vdkathvekq lssykapcrg cnkkvtlakm rvhissclkv
121 qeqmancpkf vpvvptsqpi psnipnrstf acpycgarnl dqqelvkhcv eshrsdpnrv
181 vcpicsampw gdpsyksanf lqhllhrhkf sydtfvdysi deeaafqaal alslsen
```

By "RNF166 polynucleotide" is meant a nucleic acid sequence encoding an RNF166 polypeptide. An exemplary polynucleotide sequence is provided at NCBI Accession No. NM_178841, which is reproduced below (SEQ ID NO: 16):

```
   1 ctacgatgac gtcagcgcgg cgcagtagcg gctgtgacta gcgggccggc ccgggccagg
  61 acagcgggcg gcgggcggcg cgggcctggc cccgggatgg ctatgttccg cagcctggtg
 121 gcctcggctc agcagcggca gccgccgccc gggccgcgg cggcgacag cggcctggag
 181 gcgcagtaca cctgccccat ctgcctggag gtctatcacc ggcccgtggc catcggcagc
 241 tgcggccaca cgttctgcgg ggagtgtctc cagccctgcc tgcaggtgcc atccccgctg
 301 tgcccactct gccgcctgcc cttcgacccc aagaaggtgg acaaggccac ccacgtggag
 361 aagcagctct catcctacaa agcgccctgt cgaggctgca caaaaaggt gaccctggca
 421 aagatgagag tgcacatttc gtcctgcctg aaggtccagg agcagatggc caactgcccc
 481 aagttcgtcc ccgtggtgcc cacatcacag cctatcccca gcaacatccc caacaggtcc
 541 accttcgcct gcccgtactg tggtgcccgc aacctggacc agcaggagct ggtgaagcac
 601 tgtgtggaaa gccaccgcag cgaccccaac cgcgtggtgt gccccatctg ctcggcaatg
 661 ccctgggggg accccagcta caagagcgcc aacttcctgc agcacctgct tcaccgacac
 721 aagttctcct acgacacctt tgtggactac agtattgacg aggaggccgc cttccaggct
 781 gctctggccc tgtctctctc tgagaactga agggaagcgc agccaccgc ctgcgtctgg
 841 ggtcagggat gtccccgctc ctgtgtcgca cctggcacct gctcgggagc gcacctcacc
 901 ggactgagct cacaggagga gcctgcaccc gcgcagaagg ggagccgggg ccgagcctcc
 961 gggcctgaat acgggccagc cgccgaggcc gccagagcag ggccgcctgg tcccaccggc
1021 gtcgctgggt tcttcggtgc ttctggccga gcaggcggcc tacttgggca gggctggacg
1081 ctgggacctg gagctgccgc cgtctcttca aagccatgat accccctcgt gggaagaagg
1141 gaccgacgcg cgagtcgcgc tccgcagtcg agccgggagg aacccaggct gctgccctgc
1201 ccagcccgac cctgccccgg ccccgcttcc accttgcgca tttggtactg gcttttgtga
1261 tacttaggaa ccctggcatc ttttctatat tatccagtgt gataatcttt tcacgtttta
1321 tagagcaaag acagagcagt tactcttcat attgcaatat ctgtgtttga ctaggaataa
1381 tagtattttt atggaacatt tacaaaatta tattttttaa gaaaacaatc aaaacaagca
1441 ttgggggatt ggggcaagga tggaaggagc agtgggggcag ctgccagagc tcaggcgagc
1501 catgggtct gctgtggggt ctgccctggc cacccactgt gtgtctgggt ccttgaggtt
1561 tgtacgtttc tctttgatga ccaggaagaa atcccagcac cccagccaca ggctgtggct
1621 gctcccagca gaggcgggc cggcagaaa ggggcctcct ccacccagag tcctggcctt
1681 ggcccgctgt caccttcaaa gctgactgtg ccccgctgcg ggaggggacg gcaccccagt
```

```
-continued
1741 ggtggcagag cttgggggcc tgggcagggg cccgcttggc gggccgggca acacgtcaac 1801 attcttttct gttcttggca ttaattattg ctgtcttttt tttaaaaaaa aaagtttaaa 1861 taaaatgtct cagagcatct ctaaaaaa
```

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those of ordinary skill in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those of ordinary skill in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those of ordinary skill in the art. Hybridization techniques are well known to those of ordinary skill in the art. and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence. By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "ZFP91 polypeptide" is meant a polypeptide or fragment thereof having at least 85% amino acid sequence identity to NCBI Accession No. NP_444251 or NP_001183980 (various isoforms) and having a C2H2 zinc finger targeted by lenalidomide or a lenalidomide analog. An exemplary ZFP91 polypeptide sequence provided at NCBI Accession No. NP_444251 is reproduced below (SEQ ID NO: 17):

```
  1 MPGETEEPRP PEQQDQEGGE AAKAAPEEPQ QRPPEAVAAA PAGTTSSRVL RGGRDRGRAA
 61 AAAAAAAVSR RRKAEYPRRR RSSPSARPPD VPGQQPQAAK SPSPVQGKKS PRLLCIEKVT
121 TDKDPKEEKE EEDDSALPQE VSIAASRPSR GWRSSRTSVS RHRDTENTRS SRSKTGSLQL
181 ICKSEPNTDQ LDYDVGEEHQ SPGGISSEEE EEEEEEMLIS EEEIPFKDDP RDETYKPHLE
241 RETPKPRRKS GKVKEEKEKK EIKVEVEVEV KEEENEIRED EEPPRKRGRR RKDDKSPRLP
301 KRRKKPPIQY VRCEMEGCGT VLAHPRYLQH HIKYQHLLKK KYVCPHPSCG RLFRLQKQLL
361 RHAKHHTDQR DYICEYCARA FKSSHNLAVH RMIHTGEKPL QCEICGFTCR QKASLNWHMK
421 KHDADSFYQF SCNICGKKFE KKDSVVAHKA KSHPEVLIAE ALAANAGALI TSTDILGTNP
481 ESLTQPSDGQ GLPLLPEPLG NSTSGECLLL EAEGMSKSYC SGTERVSLMA DGKIFVGSGS
541 SGGTEGLVMN SDILGATTEV LIEDSDSAGP
```

By "ZFP91 polynucleotide" is meant a nucleic acid sequence encoding an ZFP91 polypeptide. An exemplary polynucleotide sequence is provided at NCBI Accession No. NM_053023, which is reproduced below (SEQ ID NO: 18):

```
   1 gtgggggggg cgccctcgga gccgggcgga ggggaggggg gaaagaggag cgcagggtga
  61 gagtgagccg caggcttcgg gaggcgaggg ggcggggggga gcagcgccga ggccgccgcc
 121 tccgcctccg ccgcctagga ctaggggtg ggggacggac aagccccgat gccgggggag
 181 acgaagagc cgagaccccc ggagcagcag gaccaggaag ggggagaggc ggccaaggcg
 241 gctccggagg agcccccaaca acggccccct gaggcggtcg cggcggcgcc tgcagggacc
 301 actagcagcc gcgtgctgag gggaggtcgg gaccgaggcc gggccgctgc ggccgccgcc
 361 gccgcagctg tgtcccgccg gaggaaggcc gagtatcccc gccggcggag gagcagcccc
 421 agcgccaggc ctcccgacgt ccccgggcag cagccccagg ccgcgaagtc cccgtctcca
 481 gttcagggca agaagagtcc gcgactccta tgcatagaaa aagtaacaac tgataaagat
 541 cccaaggaag aaaaagagga agaagacgat tctgccctcc ctcaggaagt ttccattgct
 601 gcatctagac ctagccgggg ctggcgtagt agtaggacat ctgtttctcg ccatcgtgat
 661 acagagaaca cccgaagctc tcggtccaag accggttcat tgcagctcat ttgcaagtca
 721 gaaccaaata cagaccaact tgattatgat gttggagaag agcatcagtc tccaggtggc
 781 attagtagtg aagaggaaga ggaggaggaa gaagagatgt taatcagtga agaggagata
 841 ccattcaaag atgatccaag agatgagacc tacaaacccc acttagaaag ggaaacccca
 901 aagccacgga gaaaatcagg gaaggtaaaa gaagagaagg agaagaagga aattaaagtg
 961 gaagtagagg tggaggtgaa agaagaggag aatgaaatta gagaggatga ggaacctcca
1021 aggaagagag gaagaagacg aaaagatgac aaaagtccac gtttacccaa aggagaaaa
1081 aagcctccaa tccagtatgt ccgttgtgag atggaaggat gtggaactgt ccttgcccat
1141 cctcgctatt tgcagcacca cattaaatac cagcatttgc tgaagaagaa atatgtatgt
1201 ccccatccct cctgtggacg actcttcagg cttcagaagc aacttctgcg acatgccaaa
```

```
1261 catcatacag atcaaaggga ttatatctgt gaatattgtg ctcgggcctt caagagttcc 1321 cacaatctgg cagtgcaccg gatgattcac actggcgaga agccattaca atgtgagatc 1381 tgtggattta cttgtcgaca aaaggcatct cttaattggc acatgaagaa acatgatgca 1441 gactccttct accagttttc ttgcaatatc tgtggcaaaa aatttgagaa gaaggacagc 1501 gtagtggcac acaaggcaaa aagccaccct gaggtgctga ttgcagaagc tctggctgcc 1561 aatgcaggcg ccctcatcac cagcacagat atcttgggca ctaacccaga gtccctgacg 1621 cagccttcag atggtcaggg tcttcctctt cttcctgagc ccttgggaaa ctcaacctct 1681 ggagagtgcc tactgttaga agctgaaggg atgtcaaagt catactgcag tgggacggaa 1741 cgggtgagcc tgatggctga tgggaagatc tttgtgggaa gcggcagcag tggaggcact 1801 gaagggctgg ttatgaactc agatatactc ggtgctacca cagaggttct gattgaagat 1861 tcagactctg ccggacctta gtggacagga agacttgggg catgggacag ctcagacttt 1921 gtatttaaaa gttaaaaagg acaaaaaaaa aatctaaagc atttaaaatc tagtgaaata 1981 actgaagggc ctgctctttc cattgtggat cacagcacac acatacatac accctccacc 2041 tccccatccc ctgttctccc tctgttgctc cccttataaa attgatgttg tctttaccag 2101 aaaggtagac aaaaaagaag cagcagcagc tcttaaagtg agggttattc tcatactcgg 2161 ttccagccat cagcagactt cctgctcatc ggcagatccc cctttccaac ctgtaactct 2221 gatgtgctct ggatcagctt ttaacttta atcatatatt actgtcttct aaatcccttc 2281 tcctcctcta ctgctgccct atggttctgg ctcctacccc ctgcggcaca cttatcttca 2341 aataccatag aattctaatc tctggaggct ggcagcttga cttggcactt tagggcccct 2401 tagcagggtg agctgttaaa acagcacaca tctctcatcc cctcttcctt tattcccccc 2461 tgggtttcag aaaggaagga tatatgggga ccacctcccc cttctttgat cccagcatct 2521 cagtcccct cccaaccctc catatggctc tcaatggtgc tcacttgctt ggaagcaggc 2581 tcccaatagg gagggggctg ccctctacag tctctttgac tgtaagacag ggctctgtat 2641 cagtgagacg atgagaaaag tcccaggcta atggcagaaa tttgcacttt gaacatgtgt 2701 gttttttgtgt tgtggaacct gagattcctt atttattaac aggaagtctg attttttttt 2761 tttggagtct ttgttgctat attttgtggg gctgggagag agagattaga ttattttgac 2821 atgggatccc ttccataaca ggtactttga aggcaagaca tagggttgaa gaagcacagc 2881 cagcctctga aatcatagct ctccagtggc tttttaaagaa agctggtcct cagcactaac 2941 aaaatcacta caatagccta gtgcttttt ggaagccttt ttagggaaga atgttaggtt 3001 catggtaact agtatgctct ttgagatttt tacagtgttg aaacttaaga attttgagag 3061 ggtgaggagg gttgttcaga atctaaatta cagatagatg attgtttctt gtgaatttgt 3121 ttcttttcct ttttttttgt ccctaccatt tccttacatt tcccttgggg cccatctctg 3181 gctccttgct ttttgtttct tgctttgctt tatcagttca ttccagctcc ctgttagtga 3241 aggacactgc tgttagtgaa ggaacaaagt ctatgagtcc taaaattta agtcaaagaa 3301 aactgctctg tttccccttt agtaacactt ctgaagagga aaaacttcaa tagccaaagt 3361 taataatcct atataataat tgctttggct ttcacctaaa attctgggca tcacaatttc 3421 cttgggatag aggttgtgtt ggggaataga ttgcttattg ctgttcactg gagagaaaag 3481 gtagtgtttt tgtacaaggt cataccgcca gaagccccaa atcctatttt ggctcatctt
```

```
3541 caggtaaaga gtaattccta tcctgtgtgc ctcagaagct agaatcgaag gcttacccta 3601 ttcattgttt attgtcagaa atgcatgatg gctcttggaa agaatgacgt tttgctggaa 3661 aaaaaaaaaa gaacagtttg tgtttcacaa acatggctta tcaattttt caaagaattc 3721 ttttttccca aaagaggag taacaaaatg tcatttctga agaggctta ctttatacca 3781 actagtgtca gcatttggga tgccagggaa cagagagtga gacacctaca atcaccagtc 3841 tcaaatgcgc tattgtttct tttcagagtg ttgcagattt gccatttctc cataatatgg 3901 ggatagaaaa tggaataaag atagaaggga tgtagaatat gctttcctgc caacatggtt 3961 tggagtcgac tttggtatat tgactagatt tgaaaataca agattgatta gatgaatcta 4021 caaaaaagtt gtcctcctct caggtccctt ttacactttt tgactaacta gcatctatat 4081 tccacactta gcttttttgt cacacttatc ctttgtctcc gtaaatttca tttgcagtgg 4141 ttagtcatca gatatttag ccacctacac aaaagcaaac tgcatttta aaaatctttc 4201 tgagatggga gaaaatgtat tctcctttcc tataccgctc tcccaacaaa aaacaacta 4261 gttagttcta ctaattagaa acttgctgta cttttctt tcttttaggg gtcaaggacc 4321 ctctttatag ctaccatttg cctacaataa attattgcag cagtttgcaa tactaaaata 4381 ttttttatag actttatatt tttccttttg ataaagggat gctgcatagt agagttggtg 4441 taattaaact atctcagccg tttccctgct ttcccttctg ctccatatgc ctcattgtcc 4501 ttccagggag ctcttttaat cttaaagttc tacatttcat gctcttagtc aaattctgtt 4561 acctttttaa taactcttcc cactgcatat ttccatcttg aattggtggt tctaaattct 4621 gaaactgtag ttgagataca gctatttaat atttctggga gatgtgcatc cctcttcttt 4681 gtggttgccc aaggttgttt tgcgtaactg agactccttg atatgcttca gagaatttag 4741 gcaaacactg gccatggccg tgggagtact gggagtaaaa taaaatatc gaggtataga 4801 ctagcatcca catagagcac ttgaacctcc tttgtacctg tttggggaaa aagtataatg 4861 agtgtactac caatctaact aagattatta tagtctggtt gtttgaaata ccatttttt 4921 ctccttttgt gtttttccca ctttccaatg tactcaagaa aattgaacaa atgtaatgga 4981 tcaatttaaa atattttatt tcttaaaagc cttttttgcc tgttgtaatg tgcaggaccc 5041 ttctcctttc atgggagaga caggtagtta cctgaatata ggttgaaaag gttatgtaaa 5101 aagaaattat aataaaaggg atactttgct tttcaaatct ttgttttctc ttattctagg 5161 taaggcatat taaaaataaa tatgtaaaga agaaaaataa aagttgtctt catggaagca 5221 acttgtcttc cttggttgta ctgagttaca gttatcctag gggtgaaaca tgtgatgctg 5281 ctaagcaaac caaatgccct cagaacaggt gttatgtggg gcatactatt gtttgctttt 5341 gttgagaatc aggtggttaa ttttgactg ttcttgattt ctaatgctga aatgacatga 5401 ttctgttatt cagcaaactt ggaaatcttg atgttttgac aactgcctcc taggaaaact 5461 ggccatatgt taattaacct agtagatgga aaattaagga ttatgtgagg ttaattttac 5521 cctgataatg acaaaacctt gatagcattt aatattaata cttcttctca aaattgaatg 5581 tttatatcaa gtactgattt ttattttaaa aagaaaaaa ctataatcct tctgccttcc 5641 aaaagccatg ctgtgatagc tgcccaggct gctctgttac atctcccatt tattgtttac 5701 ttttataaat ttgcttctaa gatggaaaaa aaaaa
```

By "ZNF692 polypeptide" is meant a polypeptide or fragment thereof having at least 85% amino acid sequence identity to NCBI Accession No. NP_001129508, NP_060335, or NP_001180257 (various isoforms) and having a C2H2 zinc finger targeted by lenalidomide or a lenalidomide analog. An exemplary ZNF692 polypeptide sequence provided at NCBI Accession No. NP_001129508 is reproduced below (SEQ ID NO: 19):

```
  1 mplvhmassp avdvscrrre krrqldarrs kcrirlgghm eqwcllkerl gfslhsqlak
 61 flldrytssg cvlcagpepl ppkglqylvl lshahsrecs lvpglrgpgg qdgglvwecs
121 aghtfswgps lsptpseapk paslphttrr swcseatsgq eladlesehd ertqearlpr
181 rvgpppetfp ppgeeegeee edndedeeem lsdaslwtys sspddsepda prllpspvtc
241 tpkegetppa paalssplav palsasslss rapppaevrv qpqlsrtpqa aqqtealast
301 gsqaqsaptp awdedtaqig pkrirkaakr elmpcdfpgc grifsnrqyl nhhkkyqhih
361 qksfscpepa cgksfnfkkh lkehmklhsd trdyicefca rsfrtssnlv ihrrihtgek
421 plqceicgft crqkaslnwh qrkhaetvaa lrfpcefcgk rfekpdsvaa hrskshpall
481 lapqespsgp lepcpsisap gplgssegsr psaspqaptl lpqq
```

By "ZNF692 polynucleotide" is meant a nucleic acid sequence encoding an ZNF692 polypeptide. An exemplary polynucleotide sequence is provided at NCBI Accession No. NM_001136036, which is reproduced below (SEQ ID NO: 20):

```
   1 ggcgcacagg taaggccggg gtggggtgg  tcgcgacgg gggctctggg cagcctggga
  61 actgccattg ggattagtcc gctccactca ctgtcagcat taagtggggg tgcccaagac
 121 ggggtggatg gggggcgccc tccagacctc tgaccacggc ctcaccgcca ctcgacccaa
 181 ctatgaagag cgcccccagc tgcacgccag gacacgacct ttccttcccc tagaaaccag
 241 taaaggccgc tgccctattc aagatgaaat gtgtggaccg cccccagccc agttgaaatt
 301 tcccgtgaaa gtctctcgcc ccttccccac agctccactt cagtggactg gagggcgcag
 361 gcctttgttc tgactgcttc tgtctgcctg cctccaccc  gacgacactc acatgcctct
 421 ggtgcacatg gcttcctccc cggcggtgga cgtgtcctgc aggcggcggg agaagcggcg
 481 gcagctggac gcgcgccgca gcaagtgccg catccgcctg ggcggccaca tggagcagtg
 541 gtgcctcctc aaggagcggc tgggcttctc cctgcactcg cagctcgcca agttcctgtt
 601 ggaccggtac acttcttcag gctgtgtcct ctgtgcaggt cctgagcctt tgcctccaaa
 661 aggtctgcag tatctggtgc tcttgtctca tgcccacagc cgagagtgca gcctggtgcc
 721 cgggcttcgg gggcctggcg gccaagatgg ggggcttgtg tgggagtgct cagcaggca
 781 taccttctcc tggggaccct ctttgagccc tacaccttca gaggcaccca agccagcctc
 841 ccttccacat actactcgga gaagttggtg ttccgaggcc acgagtgggc aggagcttgc
 901 agatttggaa tctgagcatg atgagaggac tcaagaggcc aggttgccca ggagggtggg
 961 accccacca  gagaccttcc cacctccagg agaggaagag ggtgaggaag aagaggacaa
1021 tgatgaggat gaagaggaga tgctcagtga tgccagctta tggacctaca gctcctcccc
1081 agatgatagt gagcctgatg cccccagact actgccttcc cctgtcacct gcacacctaa
1141 agaggggag  acaccaccag ccctgcagc  actctccagt cctcttgctg tgccggcctt
1201 gtcagcatcc tcattgagtt ccagagctcc tccacctgca gaagtcaggg tgcagccaca
1261 gctcagcagg acccctcaag cggcccagca gactgaggcc ctggccagca ctgggagtca
1321 ggcccagtct gctccaaccc cggcctggga tgaggacact gcacaaattg gccccaagag
1381 aattaggaaa gctgccaaaa gagagctgat gccttgtgac ttccctggct gtggaaggat
```

```
                                    -continued
1441 cttctccaac cggcagtatt tgaatcacca caaaaagtac cagcacatcc accagaagtc 1501 tttctcctgc ccagagccag cctgtgggaa gtctttcaac tttaagaaac acctgaagga 1561 gcacatgaag ctgcacagtg acacccggga ctacatctgt gagttctgcg cccggtcttt 1621 ccgcactagc agcaaccttg tcatccacag acgtatccac actggagaaa aaccccctgca 1681 gtgtgagata tgcgggttta cctgccgcca gaaggcttcc ctgaactggc accagcgcaa 1741 gcatgcagag acggtggctg ccttgcgctt cccctgtgaa ttctgcggca agcgctttga 1801 gaagccagac agtgttgcag cccaccgtag caaaagtcac ccagccctgc ttctagcccc 1861 tcaagagtca cccagtggtc ccctagagcc ctgtcccagc atctctgccc ctgggcctct 1921 gggatccagc gaggggtcca ggccctctgc atctcctcag gctccaaccc tgcttcctca 1981 gcaatgagct ctcctccagc tttggctttg ggaagccaga ctccagggac tgaaaaggag 2041 caacaaggag agggtctgct tgagaaatgc cagatgcttg gtccccagga actaaggcga 2101 cagagtgcag ggtggggggca agactgggct gtagggagc tggactactt tagtcttcct 2161 aaaggacaaa ataaacagta ttttatgcag gcaaaaaaaa aaaaaaaa
```

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 5A-5B are gray scale versions of color figures. A copy of the original color heat map(s) are available upon request. The wild-type amino acid sequence of Aiolos is indicated on the x-axis (SEQ ID NO: 22), while each of the possible amino acid substitutions is indicated on the y-axis. Darker boxes indicate amino acids that depleted in the GFP negative fraction. Amino acids in the 146-168 region (SEQ ID NO: 1) were generally depleted in the GFP negative fraction, particularly amino acids at positions 147, 148, 151, 152, 153, 155, 161, 164, and 168 (indicated by arrows). The screen clearly highlights in the case of all three compounds a series of residues that define the second zinc finger motif in Aiolos. The cysteines (C) at residues 148 and 151 and the histidines (H) at residues 164 and 168 are indicative of a C2H2 zinc finger motif, and their necessity here is likely driven by their role in maintaining the structure of the zinc finger via chelation of the zinc ion. The phenylalanine (F) at 155 and leucine (L) at 161 are also common within C2H2 zinc fingers and their hydrophobic properties mediate proper folding of the tertiary structure. Most intriguing are the additional amino acids highlighted by the screen as being necessary for drug-induced targeting, including the glutamine (Q) at position 147, glycine (G) at position 152, and alanine (A) at position 153. The cysteines which are highlighted to the right of the zinc finger (i.e., the cysteines at positions 176 and 179) belong to the third zinc finger motif in Aiolos. The necessity of cysteines at positions 176 and 179 for targeting by lenalidomide or lenalidomide analogs is an artifact, as is the depletion of methionines (M) c-terminal to the second zinc finger highlighted by the screen.

FIG. 5B provides a set of schematics and a heat map showing results of a pooled saturation mutagenesis screen that established the second C2H2 zinc finger in Aiolos as the structural feature that is recognized by thalidomide, lenalidomide, and pomalidomide. At the top of FIG. 5B is a heat map depicting the lenalidomide/DMSO ratio of sequencing reads containing a given amino acid mutation (y-axis) at each position along the 60 amino acids included in the screen (SEQ ID NO: 22) (x-axis). At the middle of FIG. 5B, an amino sequence of the second C2H2 zinc finger in Aiolos is provided (SEQ ID NO: 1). Single letter amino acid symbols depicted in medium gray (asterisk) and dark gray (black bar) indicate positions that were conserved in the saturation mutagenesis screen. Medium gray (asterisk) amino acids designate positions which are components of the C2H2 zinc finger motif and are found across the C2H2 family of zinc fingers. Dark gray (black bar amino acids are polymorphic sites in C2H2 zinc fingers. At the bottom of FIG. 5B, a PDB structure of a homologous zinc finger in Eos is provided (IZKF4, Q147H).

FIG. 6A provides a schematic depiction of a pooled saturation mutagenesis screen. At the top of FIG. 6A, a stick diagram of Aiolos (IKZF3) depicting the location of six C2H2 zinc finger domains as well as the region interrogated in the screen is shown.

FIG. 6B provides a schematic depiction of the linearized protein structure of Aiolos, which contains six C2H2 zinc fingers. The second zinc finger ("ZF2") comprising amino acids 146-168 was identified in the mutagenesis screen as the structural feature required for degradation by thalidomide, lenalidomide, and pomalidomide.

FIG. 6C provides a set of flow cytometry plots demonstrating that in Aiolos-GFP fusion constructs, zinc finger 2, specifically maintenance of its tertiary structure, is required for degradation.

FIG. 6D provides a flow cytometry plot depicting lenalidomide-induced degradation of GFP which has been tagged with Aiolos zinc finger two (amino acids 146-168) via flexible linker.

FIG. 6E provides a plot showing normalized EGFP:mCherry ratios for Aiolos in the protein reporter vector (FIG. 6A, bottom) expressed via lentiviral transduction in HEK293T cells exposed to (A) DMSO control, (B) 1 μM thalidomide, (C) lenalidomide, and (D) pomalidomide.

FIG. 6F provides a flow cytometry histogram plot for Aiolos C2H2 zinc finger 2 (AA146-168) in the protein reporter vector (FIG. 6A, bottom) expressed via lentiviral transduction in HEK293T.

FIG. 7A provides a replicate-by-replicate depiction of the log 2 fold-changes in proteome abundance upon treatment with 1 uM lenalidomide in comparison to a DMSO-treated control. Arrows mark the zinc-finger containing proteins RNF166, ZFP91, and ZNF692.

FIG. 7B provides flow cytometry plots demonstrating that fusions of the zinc-finger-containing regions of RNF166, ZFP91, and ZNF692 to GFP are degraded with varying efficiencies by thalidomide, lenalidomide, and pomalidomide.

FIG. 8 (top) provides plots showing normalized EGFP:mCherry ratios for RNF166, ZNF692, and ZFP91 in the protein reporter vector (FIG. 6A, bottom) which is over-expressed via lentiviral transduction in HEK293T cells exposed to (A) DMSO control, (B) 1 μM thalidomide, (C) lenalidomide, and (D) pomalidomide. Bars corresponding to treatment groups A-D are consistent amongst all genetic background groups. Bar height is the average of three replicates, error bars represent 95% confidence intervals. At the bottom of FIG. 8, an alignment of the zinc finger degron sequences in Aiolos, Ikaros, RNF166, ZNF692, and ZFP91 is shown (SEQ ID NOS 1 and 1-4, respectively, in order of appearance). Light gray (asterisk) and medium gray (black bar) bars indicate positions that were conserved in the saturation mutagenesis screen. Light gray (asterisk) amino acids designate positions which are components of the C2H2 zinc finger motif and are found across the C2H2 family of zinc fingers. Medium gray (black bar) amino acids are polymorphic sites in C2H2 zinc fingers.

FIG. 9A provides a flow-chart of the screening method (top). "Len" refers to lenalidomide. The bottom of FIG. 9A provides a plot showing cell number throughout the duration of the 20 day assay (DMSO; 1 replicate, 1 uM Len; the average of three replicates).

FIG. 9B provides a plot showing the gRNA library ranked according to the Len/DMSO fold-change of the log 2-transformed gRNA read count (average of 3 replicates). Light gray lines indicate 3 standard deviations above and below the mean.

FIG. 9C provides a diagram showing STARS algorithm output for the top 30 genes according to day 20 gRNA ranking.

FIG. 10A provides a schematic of the reporter vector (top); features of the secondary library (middle); and a flow chart of the reporter screen (bottom).

FIG. 10B provides a diagram showing genes from the reporter screen ranked according to the average fold-change in the log-2 transformed gRNA sequencing read counts (Len-treated EGFP+/DMSO). "Len" refers to lenalidomide. Fold-change values are normalized to the average fold-change of 12 control gRNAs. Each point represents an individual gRNA, and each point is the average of three infection replicates. Light gray lines represent 2 standard deviations above and below the mean of the control gRNAs.

DETAILED DESCRIPTION OF THE INVENTION

The invention features methods that are useful for identifying proteins degraded in a CRL4-CRBN-dependent fashion by thalidomide, lenalidomide, and pomalidomide on the basis of their amino acid sequence.

The invention is based, at least in part, on the discovery of a degron sequence; an amino acid sequence within Aiolos (IKZF3) that mediates its association with thalidomide, lenalidomide, and pomalidomide in complex with cereblon, the substrate receptor for the CRL4-CRBN E3 ubiquitin ligase. The discovery of the degron sequence in Aiolos (IKZF3) was achieved by means of a functional, comprehensive saturating mutagenesis screen of amino acids 130-189 in Aiolos (IKZF3). The amino acids identified fall within a zinc finger motif in Aiolos, suggesting that these compounds may target other transcription factors containing zinc finger motifs. Indeed, at least three other zinc-finger-containing proteins (RNF166, ZFP91, and ZNF692) have been preliminarily confirmed via multiple methods to be targets of these compounds. These findings indicate that the structural motif identified in the primary screen can be used to identify additional, potentially therapeutically relevant targets of these compounds.

It has recently been understood that this family of compounds derive their therapeutic properties from their unique ability to enforce degradation of several protein targets by the CRL4-CRBN E3 ubiquitin ligase. Specifically, these drugs are known to cause CRL4-CRBN-dependent ubiquitination and proteasomal degradation of the transcription factors Ikaros (IKZF1) and Aiolos (IKZF3), as well as Casein Kinase 1 Alpha (CSNK1a1). While the degradation of these targets explains the drugs' therapeutic efficacy in multiple myeloma and 5q-MDS, there are a number of cellular and clinical phenotypes elicited by thalidomide, lenalidomide, and pomalidomide which cannot yet be explained by the depletion of these proteins. Examples would include their sedative properties, teratogenicity, and anti-inflammatory effects.

Improved understanding of the mechanism through which these drugs function has provided knowledge necessary to design molecular technologies capable of identifying additional, potentially therapeutically relevant proteins which are degraded by thalidomide, lenalidomide, and pomalidomide. The identification of novel protein targets of these compounds could provide a molecular basis for the numerous cellular and clinical phenotypes which these drugs elicit, broaden the spectrum of disorders which may benefit from their use, and facilitate medicinal chemistry efforts to design more specific and potent compounds. The newly appreciated mechanism of action of thalidomide, lenalidomide, and pomalidomide has also provided a context allowing understanding and detection of resistance to these drugs in patients, particularly at an early stage of a disease, thereby facilitating expedient and rational choice of alternate therapies.

Figure 1:
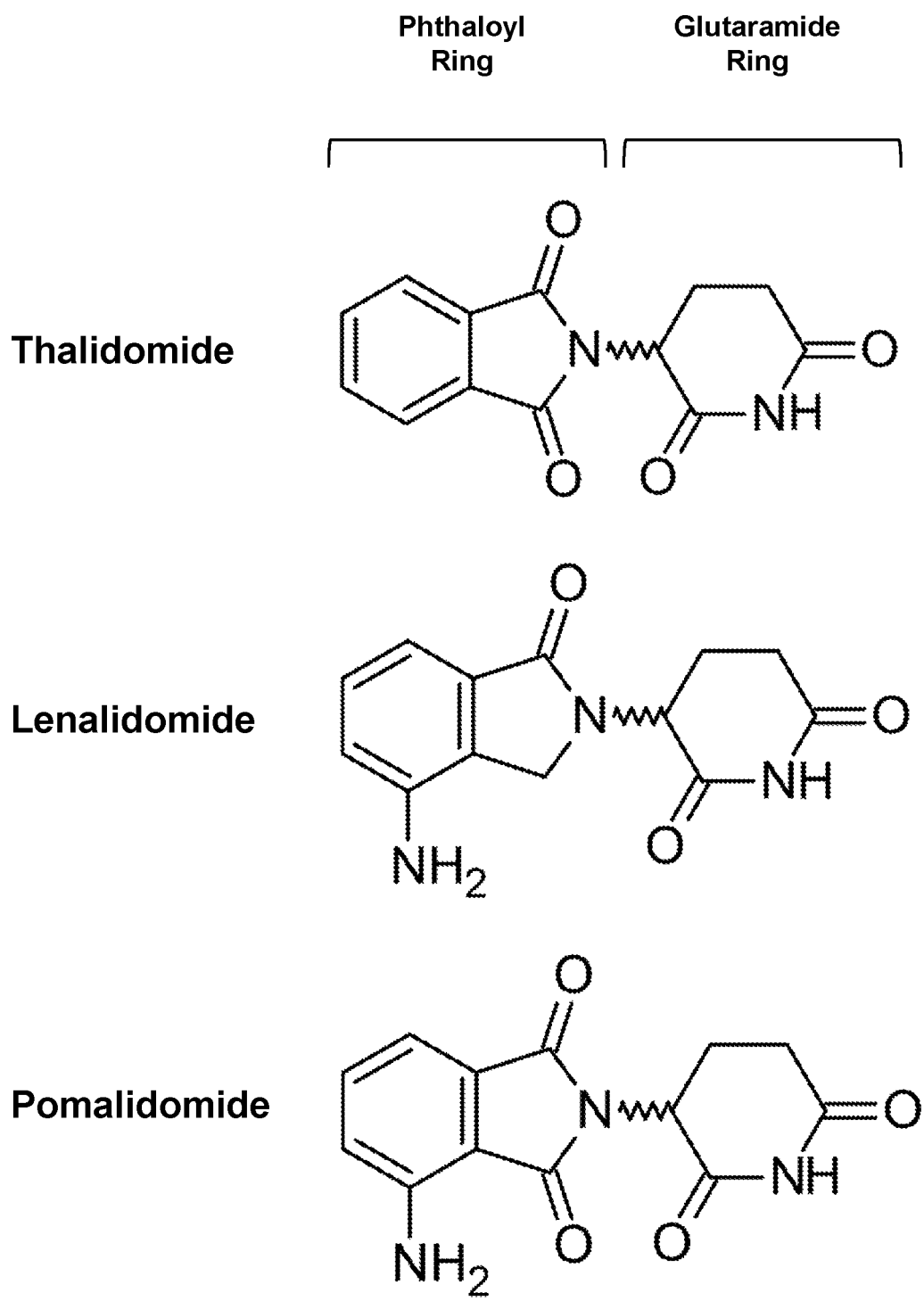
FIG. 1 depicts a schematic representation of the molecular structure of thalidomide and its derivatives.

Lenalidomide- and Lenalidomide Analog-Dependent Mediation of Proteasomal Degradation The drug thalidomide became infamous in the early 1960s when its use during the first trimester of pregnancy was linked to profound birth defects, most commonly a malformation of the upper limbs known as phocomelia. The discovery of thalidomide's teratogenic property was a major setback for the compound, however thalidomide was later repurposed and today is an FDA-approved therapy for a number of disorders, including erythema nodosum leparum, 5q-myelodysplastic syndrome (MDS), and the plasma cell malignancy multiple myeloma. Thalidomide's success as a treatment for these disorders motivated the synthesis of lenalidomide and pomalidomide, more potent derivatives which have largely replaced thalidomide in the treatment of 5q-MDS and multiple myeloma (FIG. 1).

Figure 2:
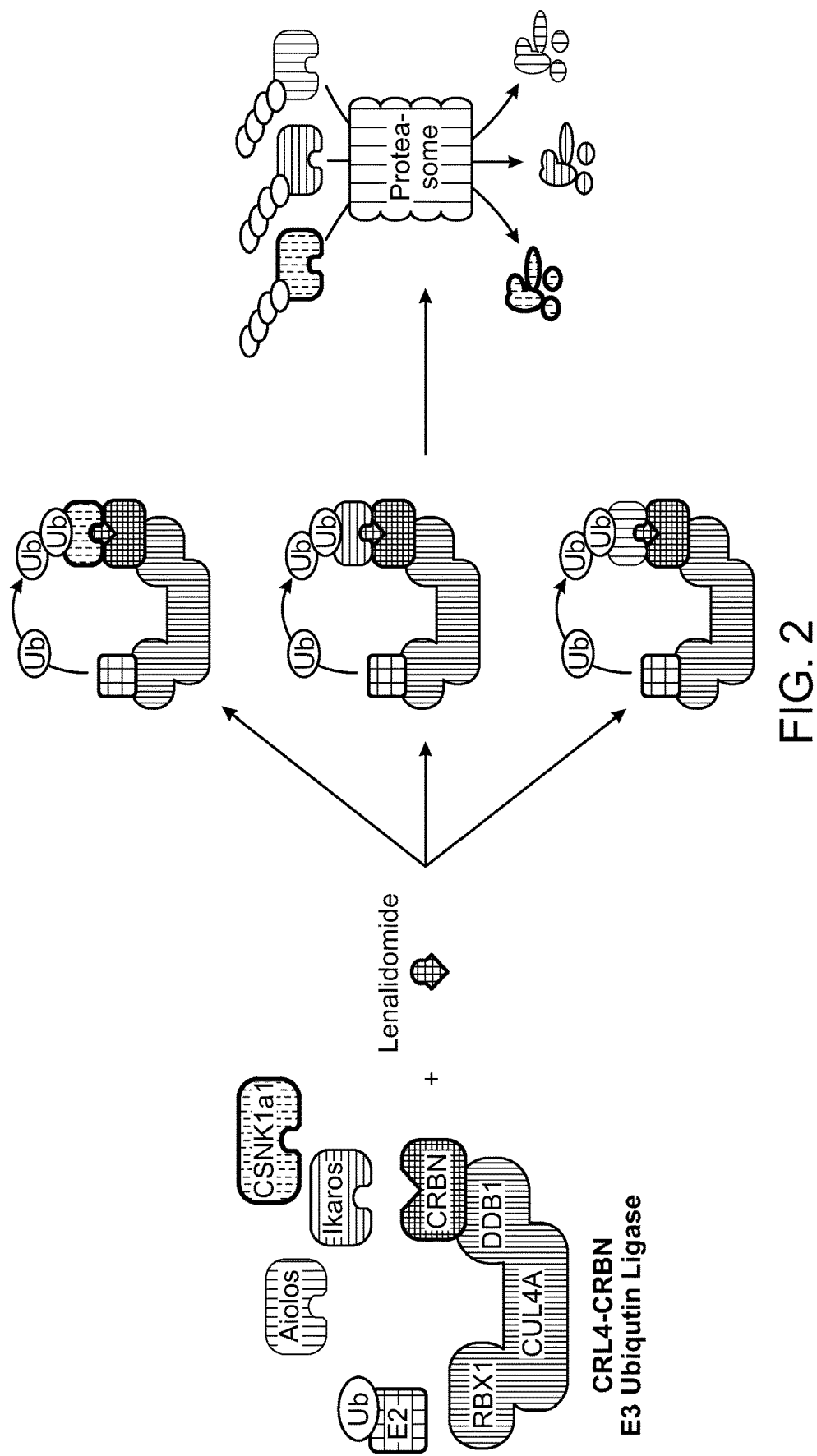
FIG. 2 depicts a schematic representation of the molecular mechanism of lenalidomide-mediated degradation. Lenalidomide binds to cereblon at its putative substrate recognition surface and in doing so, increases the affinity of cereblon for several key substrates; the lymphocyte lineage transcription factors Ikaros (IKZF1) and Aiolos (IKZF3), and Casein Kinase 1 alpha (CSNK1a1). This increase in affinity subsequently results in the efficient CRL4-CRBN-dependent polyubiquitination of these target substrates, causing them to be rapidly degraded by the 26S proteasome. Degradation of Ikaros and Aiolos has been demonstrated to mediate the cell-autonomous effects in multiple myeloma as well as the increase in IL-2 secretion from T cells. Degradation of casein kinase 1 alpha appears to drive the therapeutic benefit observed in myelodysplastic syndrome.

Despite their clinical success, the mechanism behind the therapeutic benefit of thalidomide and its derivatives remained a mystery for over a decade. It is now understood that these drugs function by mediating efficient proteasomal degradation of several protein targets by the CRL4-CRBN E3 ubiquitin ligase. These targets include the lymphocyte lineage transcription factors Ikaros (IKZF1) and Aiolos (IKZF3), as well as the Wnt pathway regulator Casein Kinase 1 alpha (CSNK1a1). The CRL4-CRBN ubiquitin ligase belongs to the family of cullin-ring ligases and is a multi-subunit complex comprised of Ring Box Protein 1 (RBX1), DNA Damage Binding Protein 1 (DDB1), Cullin 4A (CUL4A), and Cereblon (CRBN). Thalidomide, lenalidomide, and pomalidomide bind specifically to cereblon, the substrate receptor for CRL4-CRBN. In doing so, these drugs increase Cereblon's affinity for Ikaros (IKZF1), Aiolos (IKZF3), and Casein Kinase 1 alpha (CSNK1a1). As a consequence of their increased association with the CRL4-CRBN ubiquitin ligase complex, these factors are efficiently ubiquitinated and degraded by the 26S proteasome (FIG. 2). Without wishing to be bound by theory, the degradation of Ikaros and Aiolos explains not only the tumoricidal effect on myeloma cells, but the increase in IL-2 secretion by T cells (Lu et al., 2014, Science 343, 305-309; Kronke et al., 2014, Science 343, 301-305; Ghandi et al., 2013, British Journal of Haematology, doi:10.1111/bjh. 12708). Similarly, the degradation of Casein Kinase 1 alpha mediates remission of the malignant stem cell clone in 5q-in myelodysplastic syndrome.

The present invention features methods that are useful for identifying proteins degraded in a CRL4-CRBN-dependent fashion by thalidomide, lenalidomide, and pomalidomide on the basis of their amino acid sequence. In other aspects, the present invention features a method of depleting a polypeptide in a cell, the method comprising (a) detecting or fusing an IKFZ3 sequence to the polypeptide; and (b) contacting the cell with lenalidomide or a lenalidomide analog, degrading the target polypeptide in the cell. The methods of the present invention are based, at least in part, on the discovery of an amino acid sequence within Aiolos (IKZF3) that mediates its association with thalidomide, lenalidomide, and pomalidomide in complex with cereblon, the substrate receptor for the CRL4 CRBN E3 ubiquitin ligase. Thus, in some aspects, the present invention features methods capable of identifying or detecting a sequence substantially identical to this amino acid sequence in a polypeptide, wherein presence of the sequence indicates increased degradation of the polypeptide in a cell when the cell is contacted with lenalidomide or a lenalidomide analog.

Identification of Drug-Induced Targets of Thalidomide, Lenalidomide, and Pomalidomide The present invention features methods for identifying drug-modulated (in particular, lenalidomide- or lenalidomide analog-modulated) substrates of CRBN. The present invention also features methods for identifying polypeptide targets of thalidomide, lenalidomide, or pomalidomide. Proteomic methods, specifically mass spectrometry, have served as an effective approach to identify the drug-induced targets of thalidomide, lenalidomide, and pomalidomide.

A caveat to this strategy, however, is that mass spectrometry can only detect changes in the levels of proteins which are expressed by the cell type being examined. Indeed, it is almost certain that all substrates whose protein levels are perturbed by this family of drugs have yet to be identified; the current list of targets fail to explain a number of these compounds' effects, most notably the sedative and antiemetic properties for which thalidomide was originally marketed and the teratogenic effects which nearly eradicated these drugs from the armamentarium. An alternative strategy which has been used to discover ubiquitin ligase substrates in a cell-type independent manner is to take a structural approach and define the amino acid sequences responsible for targeting proteins to their cognate ubiquitin ligase (Nash et al., 2001, Nature 29,414(6863):514-21). In the study described herein, the consensus "degron" sequence which mediates binding of Aiolos (IKZF3) to the drug-cereblon complex was defined. It is planned that this consensus sequence will be used to examine the proteome for other possible drug-induced targets of the CRL4-CRBN ubiquitin ligase.

Described herein is a functional, comprehensive saturating mutagenesis screen which has revealed the amino acid sequence within Aiolos (IKZF3) that mediates its association with thalidomide, lenalidomide, and pomalidomide in complex with cereblon, the substrate receptor for the CRL4 CRBN E3 ubiquitin ligase. The amino acids identified fall within a zinc finger motif in Aiolos, suggesting the possibility that these compounds may target other transcription factors containing zinc finger motifs. Ikaros (IKZF1) contains a zinc finger motif identical to the motif identified in Aiolos (IKZF3). The implication of this work is therefore the potential to use the structural motif identified in the primary screen to identify additional, potentially therapeutically relevant targets of these compounds.

Lenalidomide and Lenalidomide Analog Therapies

Lenalidomide and lenalidomide analogs are effective therapies for a number of diseases or disorders, including 5q-myelodysplastic syndrome (MDS), erythema nodosum leparum, and several mature B-cell malignancies, most notably, the plasma cell malignancy multiple myeloma. Lenalidomide analogs approved for clinical use by the Food and Drug Administration (FDA) include thalidomide and pomalidomide. Lenalidomide is approved by the FDA for treatment of 5q-myelodysplastic syndrome (MDS), erythema nodosum leparum, and multiple myeloma. In some embodiments, lenalidomide and lenalidomide analogs are administered to a subject having 5q-myelodysplastic syndrome (MDS) or plasma cell malignancy multiple myeloma.

In some aspects, methods of the invention (which include prophylactic treatment) comprise administration of a therapeutically effective amount of lenalidomide or a lenalidomide analog, such as thalidomide or pomalidomide, to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, family history, and the like).

Lenalidomide or lenalidomide analogs may be also used in the treatment of any other disorders in which Ikaros (IKZF1), Aiolos (IKZF3), Casein Kinase 1 alpha (CSNK1a1), or other targets of lenalidomide may be implicated.

Characterizing and Monitoring Effectiveness of Lenalidomide and Lenalidomide Analog Therapies Although thalidomide, lenalidomide, and pomalidomide are effective therapies for a number of disorders, most notably 5q-myelodysplastic syndrome and the plasma cell malignancy multiple myeloma, their effectiveness is hampered by development of resistance to these drugs. For example, lenalidomide is currently used in combination with dexamethasone as a front-line therapy for standard-risk multiple myeloma. While this combination offers distinct benefits with regard to disease-free and overall survival, the combination of dexamethasone and lenalidomide is not curative; on average disease progression develops 11 months after initiating treatment (Dimopoulos et al., 2007, N. Engl. J. Med., 357, 2123-2132; Weber et al., 2007, N. Engl. J. Med., 357, 2133-2142).

Without intending to be bound by theory, lenalidomide- or lenalidomide analog-induced association with cereblon (CRBN) and CRBN-mediated degradation of Ikaros (IKZF1) and Aiolos (IKZF3) are believed to confer the therapeutic effects of lenalidomide or lenalidomide analogs in disorders such as multiple myeloma. Thus, the identification of the amino acid sequence within Aiolos (IKZF3) that mediates its association with thalidomide, lenalidomide, and pomalidomide in complex with cereblon has potential clinical ramifications, as the mutation status of this region may serve as a biomarker capable of stratifying multiple myeloma patients with regard to their potential to respond to lenalidomide, and with regard to the choice of secondary therapies following relapse. Mutations in this region of Aiolos (IKZF3) may also be relevant biomarkers in the context of other malignancies treated with lenalidomide or lenalidomide analogs. In addition, the amino acid sequence identified in Aiolos (IKZF3) is within a zinc finger motif. Ikaros (IKZF1) contains a zinc finger motif identical to the motif identified in Aiolos (IKZF3). Without being bound by theory, it is believed that the amino acids in Ikaros' (IKZF1) zinc finger which correspond to those amino acids identified in Aiolos (IKZF3) are also responsible for mediating Ikaros' (IKZF1) association with cereblon (CRBN) and Cereblon-mediated degradation of Ikaros (IKZF1). Thus, mutations in the corresponding amino acids in IKZF1 may also serve as biomarkers of lenalidomide or lenalidomide analog resistance.

Accordingly, the present invention features methods of characterizing and/or monitoring the lenalidomide sensitivity of a subject comprising detecting the sequence of a region in an IKZF3 or IKZF1 polynucleotide relative to an IKZF3 or IKZF1 reference sequence. The methods include the step of detecting a sequence of a polypeptide or polynucleotide of Aiolos (IKZF3) and/or Ikaros (IKZF1) in a biological sample from a subject suffering from or susceptible to a disorder or symptoms thereof associated with protein targets of lenalidomide, in which the subject has been administered a therapeutic amount of lenalidomide sufficient to treat the disease or symptoms thereof. The detection of a mutation in a polypeptide or polynucleotide of IKZF3 and/or IKZF1 is indicative of lenalidomide resistance and failure to detect a mutation is indicative of lenalidomide sensitivity.

The sequence of a polypeptide or polynucleotide of IKZF3 and/or IKZF1 detected in the method can be compared to a reference sequence. The reference sequence may be a known sequence of the gene in healthy normal controls.

In some embodiments, a sequence of a polypeptide or polynucleotide of IKZF3 and/or IKZF1 in the subject is determined at a time point later than the initial determination of the sequence, and the sequences are compared to monitor the efficacy of the therapy. In other embodiments, a pretreatment sequence of a polypeptide or polynucleotide of IKZF3 and/or IKZF1 in the subject is determined prior to beginning treatment according to this invention; this pretreatment sequence of a polypeptide or polynucleotide of IKZF3 and/or IKZF1 can then be compared to the sequence of the polypeptide or polynucleotide of IKZF3 and/or IKZF1 in the subject after the treatment commences, to determine the efficacy of the treatment.

In some embodiments, thalidomide, lenalidomide, and pomalidomide are administered to a subject having a B cell neoplasia, such as multiple myeloma. Over time, many patients treated with lenalidomide acquire resistance to the therapeutic effects of lenalidomide. For example, lenalidomide is currently used in combination with dexamethasone as a front-line therapy for standard-risk multiple myeloma. While this combination offers distinct benefits with regards to disease-free and overall survival, the combination of dexamethasone and lenalidomide is not curative; on average disease progression develops 11 months after initiating treatment (Dimopoulos et al., 2007, N. Engl. J. Med., 357, 2123-2132; Weber et al., 2007, N. Engl. J. Med., 357, 2133-2142).

The early identification of lenalidomide resistance in a B cell neoplasia patient is important to patient survival because it allows for the selection of alternate therapies. Without wishing to be bound by theory, the anti-proliferative effect of lenalidomide in B cell neoplasias (in particular, multiple myeloma) is mediated by the combined depletion of Aiolos (IKZF3) and Ikaros (IKZF1). Accordingly, the invention provides methods for identifying the presence of lenalidomide resistant cells by detecting IKZF3 and/or IKZF1 polypeptides that are resistant to lenalidomide-induced degradation. In one embodiment, a lenalidomide or lenalidomide analog resistant cell is identified by detection of a mutation in IKZF3 and/or IKZF1. Subjects identified as having a lenalidomide resistant B cell neoplasia are identified as in need of alternative treatment. Subjects identified as having a lenalidomide resistant myeloma, for example, are treated with Velcade, corticosteroids, or other anti-neoplastic therapy. For subjects identified as having lenalidomide resistant myelodysplastic syndrome are treated, for example, with azacitidine or decitabine.

In other embodiments, a lenalidomide or lenalidomide analog sensitivity in a subject is characterized by detecting a mutation in IKZF3 and/or IKZF1 polynucleotide or polypeptide sequence in a biological sample of the subject, such as a mutation in any one or more of amino acids 146-168. In particular embodiments, the invention provides for the detection of a mutation at amino acid 147, 148, 151, 152, 153, 155, 161, 164, or 168 in an IKZF3 polypeptide. These mutations are in a C2H2 zinc finger motif within Aiolos (IKZF3). Ikaros (IKZF1) contains an identical zinc finger. Thus, in other embodiments, the invention also provides for the detection of a mutation in Ikaros' (IKZF1) corresponding amino acids, which include amino acids at positions 146, 147, 150, 151, 152, 163, or 167. Methods for detecting a mutation of the invention include immunoassay, direct sequencing, and probe hybridization to a polynucleotide encoding the mutant polypeptide. Exemplary methods of detecting a mutation of the invention are described in, for example, U.S. Patent Application Publication No. US2014/0127690, which is incorporated by reference herein in its entirety.

Methods of monitoring the sensitivity to lenalidomide or lenalidomide analog of a subject having a disease (e.g., a B cell neoplasia) are useful in managing subject treatment. Provided herein are methods where alterations in a polynucleotide or polypeptide of IKZF3 and/or IKZF1 (e.g., sequence, level, post-transcriptional modification, biological activity) are analyzed, such as before and again after subject management or treatment. In these cases, the methods are used to monitor the status of lenalidomide sensitivity (e.g., response to lenalidomide treatment, resistance to lenalidomide, amelioration of the disease, or progression of the disease).

For example, polypeptides or polynucleotides of IKZF3 and/or IKZF1 can be used to monitor a subject's response to certain treatments of a disease (e.g., B cell neoplasia). The level, biological activity, sequence, post-transcriptional modification, or sensitivity to lenalidomide induced degradation of a polypeptide or polynucleotide of IKZF3 and/or IKZF1 may be assayed before treatment, during treatment, or following the conclusion of a treatment regimen. In some embodiments, multiple assays (e.g., 2, 3, 4, 5) are made at one or more of those times to assay resistance to lenalidomide.

Alterations in polynucleotides or polypeptides of IKZF3 and/or IKZF1 (e.g., sequence, level, post-transcriptional modification, biological activity) are detected in a biological sample obtained from a patient that has or has a propensity to develop a disease, such as B cell neoplasia. Such biological samples include, but are not limited to, peripheral blood, bone marrow, or lymphoid tissue obtained from the subject relative to the level of such biomarkers in a reference.

Combination Therapies

In some aspects, the present invention provides methods for detecting alterations in a polypeptide or polynucleotide of IKZF3 and/or IKZF1 in a biological sample (e.g., peripheral blood, bone marrow) derived from a subject having a B cell neoplasia to determine whether the B cell neoplasia is sensitive to treatment with lenalidomide or whether it has acquired lenalidomide resistance. Alterations in IKZF3 and/or IKZF1 are useful individually, or in combination with other markers typically used in characterizing a B cell neoplasia.

B-cell neoplasms typically recapitulate the normal stages of B-cell differentiation, and can be classified according to their putative cell of origin. Accordingly, alterations in IKZF1 and/or IKZF3 may be assayed alone or in combination with the neoplasm's cytogenetic profile, genotype, and immunophenotype. B cell markers useful in the methods of the invention include, but are not limited to, characterization of CD5, CD10, CD19, CD20, CD22, CD23, FMC7, CD79a, CD40, CD38, and CD138.

Kits

In one aspect, the invention provides kits for monitoring lenalidomide- or lenalidomide analog sensitivity, including the development of lenalidomide- or lenalidomide analog resistance. For example, the kits can be used to detect an alteration in a polypeptide or polynucleotide of IKZF3 and/or IKZF1 (e.g., sequence level, post-transcriptional modification, biological activity).

If desired a kit includes any one or more of the following: capture molecules that bind a polynucleotide or polypeptide of IKZF3 and/or IKZF1. The capture molecules may be sequencing primers or hybridization probes for detecting the sequence of a polynucleotide of IKZF3 and/or IKZF1. The kits have many applications. For example, the kits can be used to determine if a subject has a lenalidomide sensitive disorder (e.g., a lenalidomide sensitive multiple myeloma) or if the subject has developed resistance to lenalidomide.

The kits may include instructions for the assay, reagents, testing equipment (test tubes, reaction vessels, needles, syringes, etc.), standards for calibrating the assay, and/or equipment provided or used to conduct the assay. The instructions provided in a kit according to the invention may be directed to suitable operational parameters in the form of a label or a separate insert.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology;" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Identification of Amino Acid Sequence in Aiolos (IKZF3) that Mediates Targeting by Thalidomide, Lenalidomide, and Pomalidomide Described herein is a study defining an amino acid sequence in Aiolos (IKZF3) which mediates binding of Aiolos (IKZF3) to the drug-cereblon complex. This sequence may be used to examine the proteome for other possible drug-induced targets of the CRL4-CRBN ubiquitin ligase.

Figure 3:
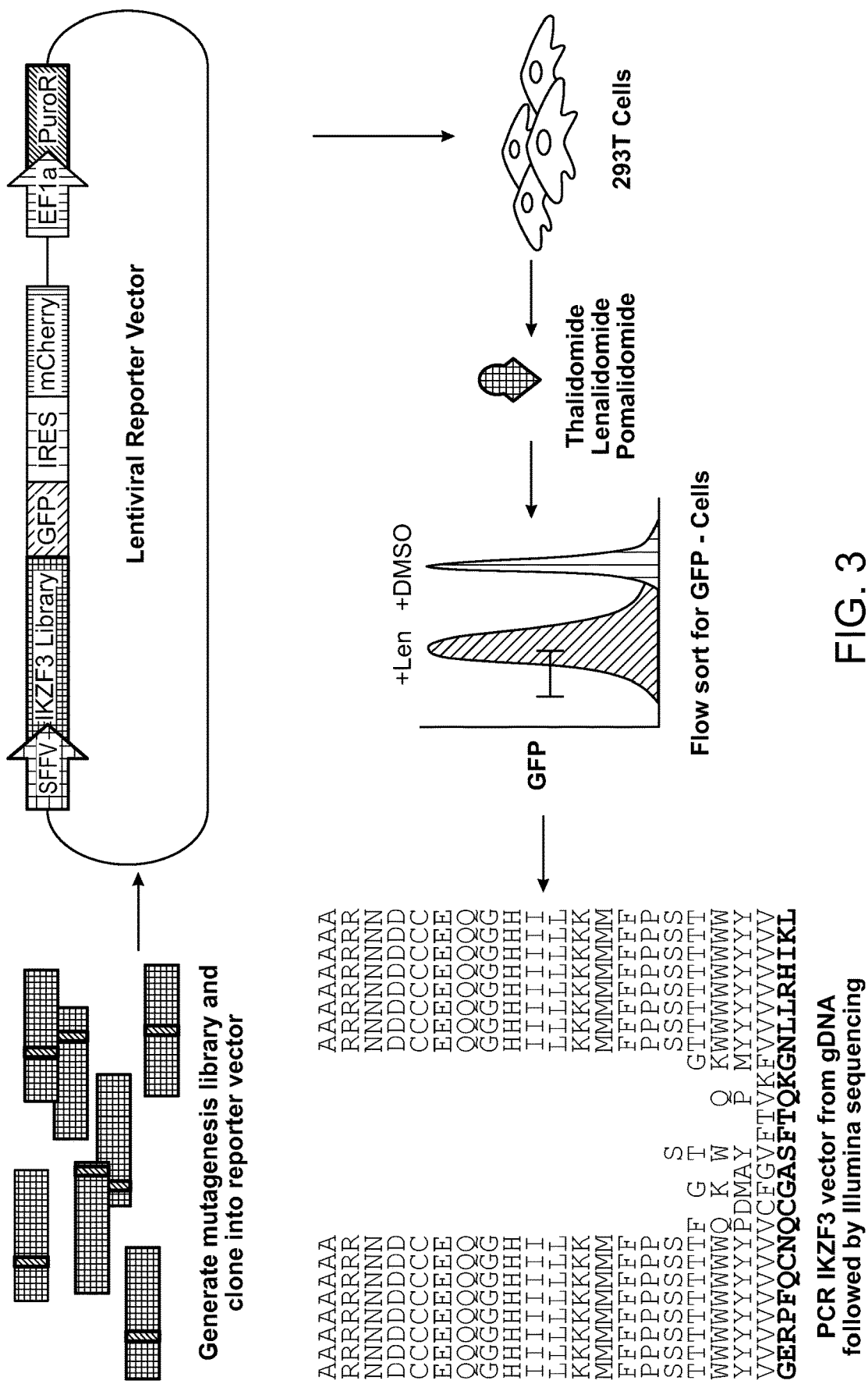
FIG. 3 depicts a schematic diagram of the workflow described herein for identification of the degron sequence (SEQ ID NO: 21) in Aiolos via screening of a comprehensive scanning mutagenesis library in a fluorescent reporter system.

In this study, a region within Aiolos (IKZF3) which mediates lenalidomide- or lenalidomide analog mediated binding of Aiolos to the CRL4-CRBN ubiquitin ligase was identified. The degron region within Aiolos had previously been narrowed down to amino acids 130-189, a stretch of 60 amino acids that is necessary and sufficient to confer lenalidomide-induced degradation by the CRL4-CRBN ubiquitin ligase (Kronke et al., 2014, Science, 343: 301-305). Traditional cloning methods, however, had failed to reduce this region further and specifically delineate which amino acids are functionally relevant for drug-induced binding to cereblon. As an alternative approach, an array-based synthesis of DNA oligos to generate a comprehensive scanning mutagenesis library of amino acids 130-189 in Aiolos was utilized (FIG. 3). In this mutagenesis library each construct contained approximately one amino acid mutation, and within the total library, each amino acid was mutated such that each of the other 19 amino acids were represented at that location (Melnikov et al., 2014, J. Vis. Exp., doi: 10.3791/51719). The library, which contained approximately 1,200 constructs, was cloned in-frame with GFP in a lentiviral plasmid. This plasmid additionally contained an IRES.mCherry sequence as an internal control to distinguish fluctuations in GFP that were occurring at the transcriptional or post-translational level, as well as a puromycin resistance cassette to serve as a pharmacologic selection marker. Previous optimization had demonstrated that this fluorescence-based degron reporter system was capable of discriminating single amino acid alterations that disrupted the functionality of the degron, specifically a Q147H mutation.

Figure 4:
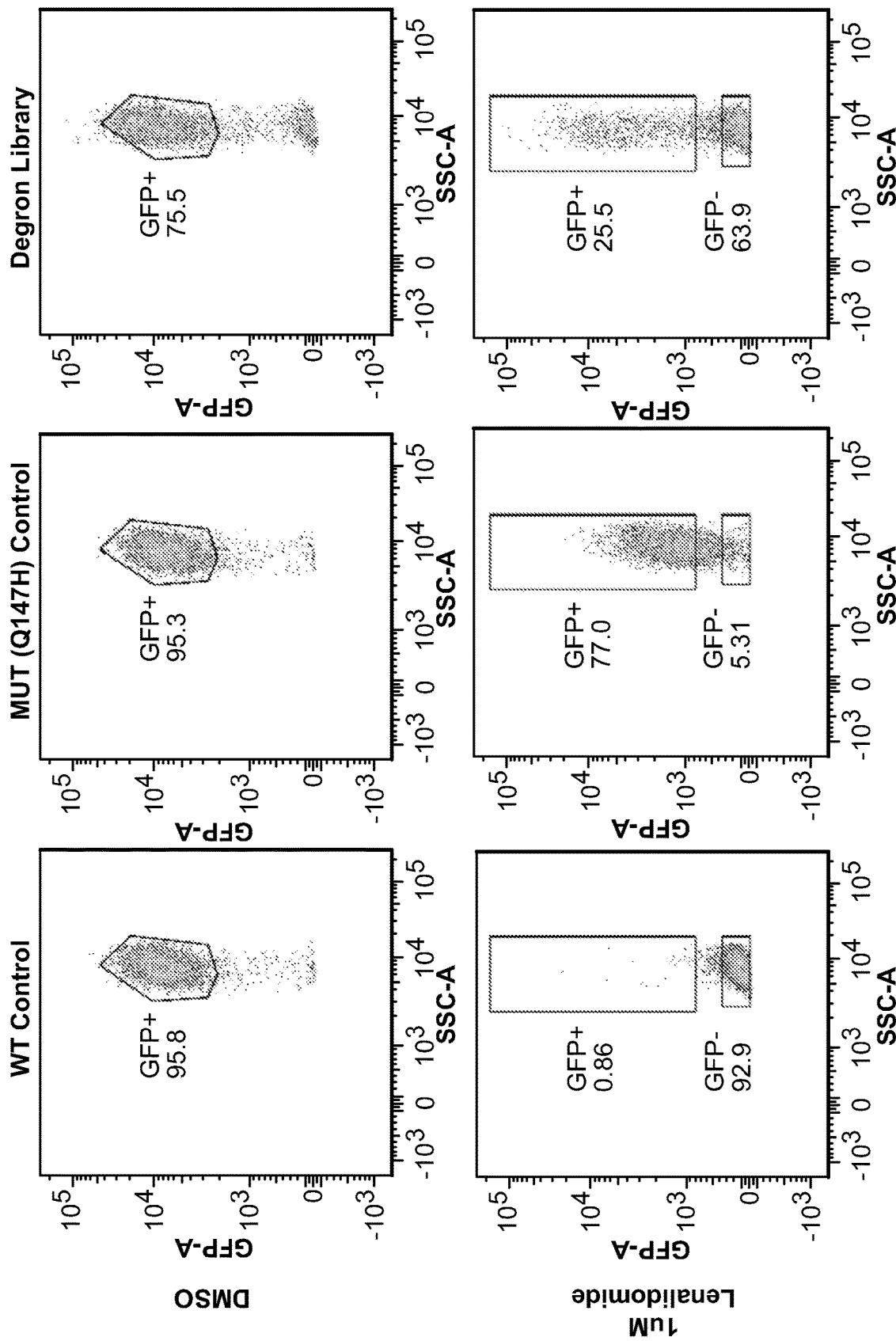
FIG. 4 provides a set of plots depicting a representative analysis of flow cytometry data from the screen described herein. Upon 20 hours of lenalidomide treatment there is a clear reduction the level of GFP fluorescence in the wild-type (WT) control sample, however a single amino acid mutation (Q147H) in the mutant (MUT) control sample exhibits an attenuated response by comparison; this result highlights the ability of this fluorescence-based reporter system to distinguish functional, single amino acid changes that alter degradation. Of note, an increase in the GFP+ population upon treatment with lenalidomide is observed when comparing the degron library sample to the WT Control sample, likely indicating that constructs are present in the library in which the amino acid alterations have disrupted lenalidomide-mediated targeting by the CRL4-CRBN ubiquitin ligase.
Figure 5A:
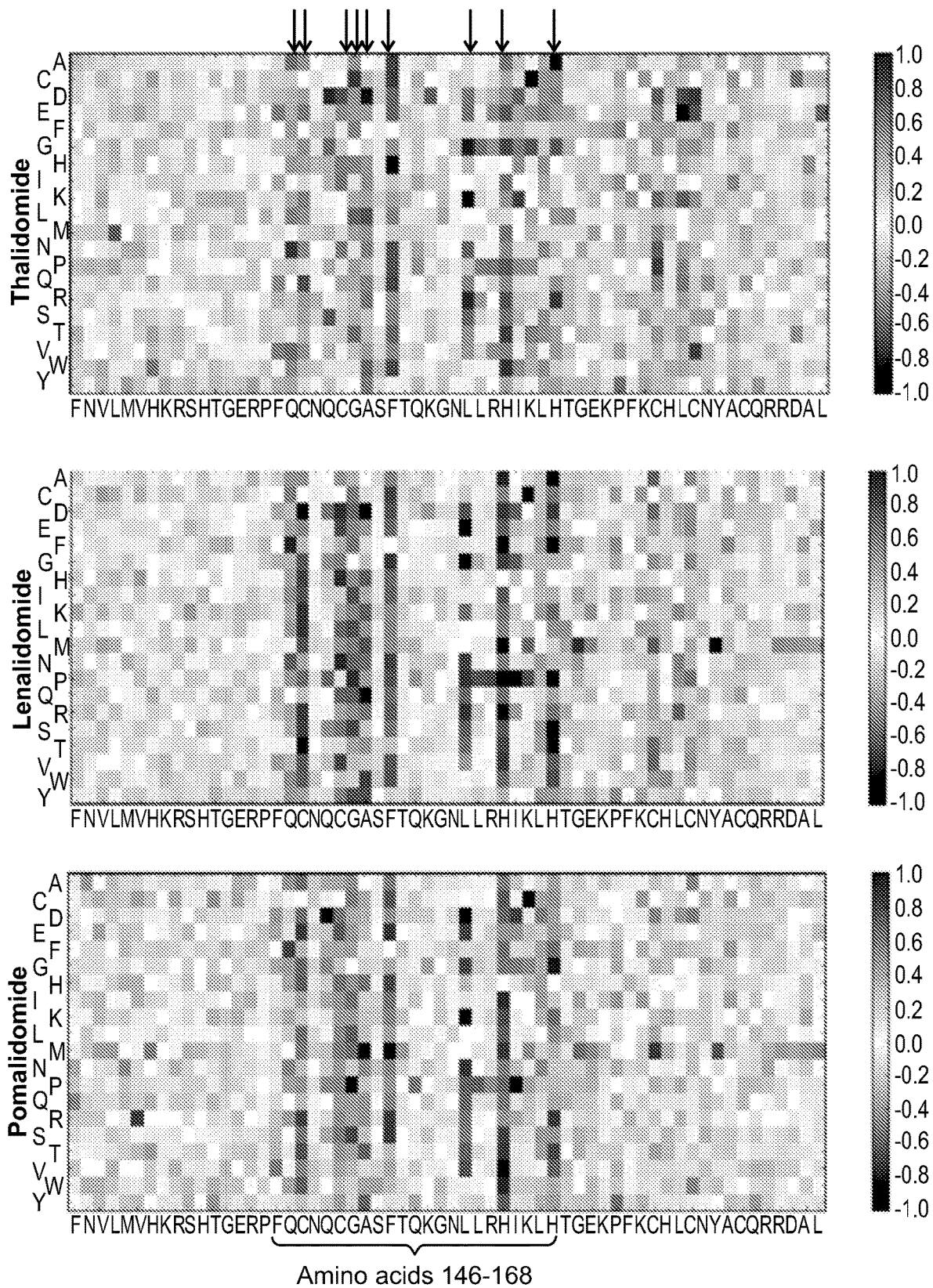
FIGS. 5A-5B provide heat maps showing the results of the comprehensive scanning mutagenesis of Aiolos amino acids 130-189.
Figure 5B:
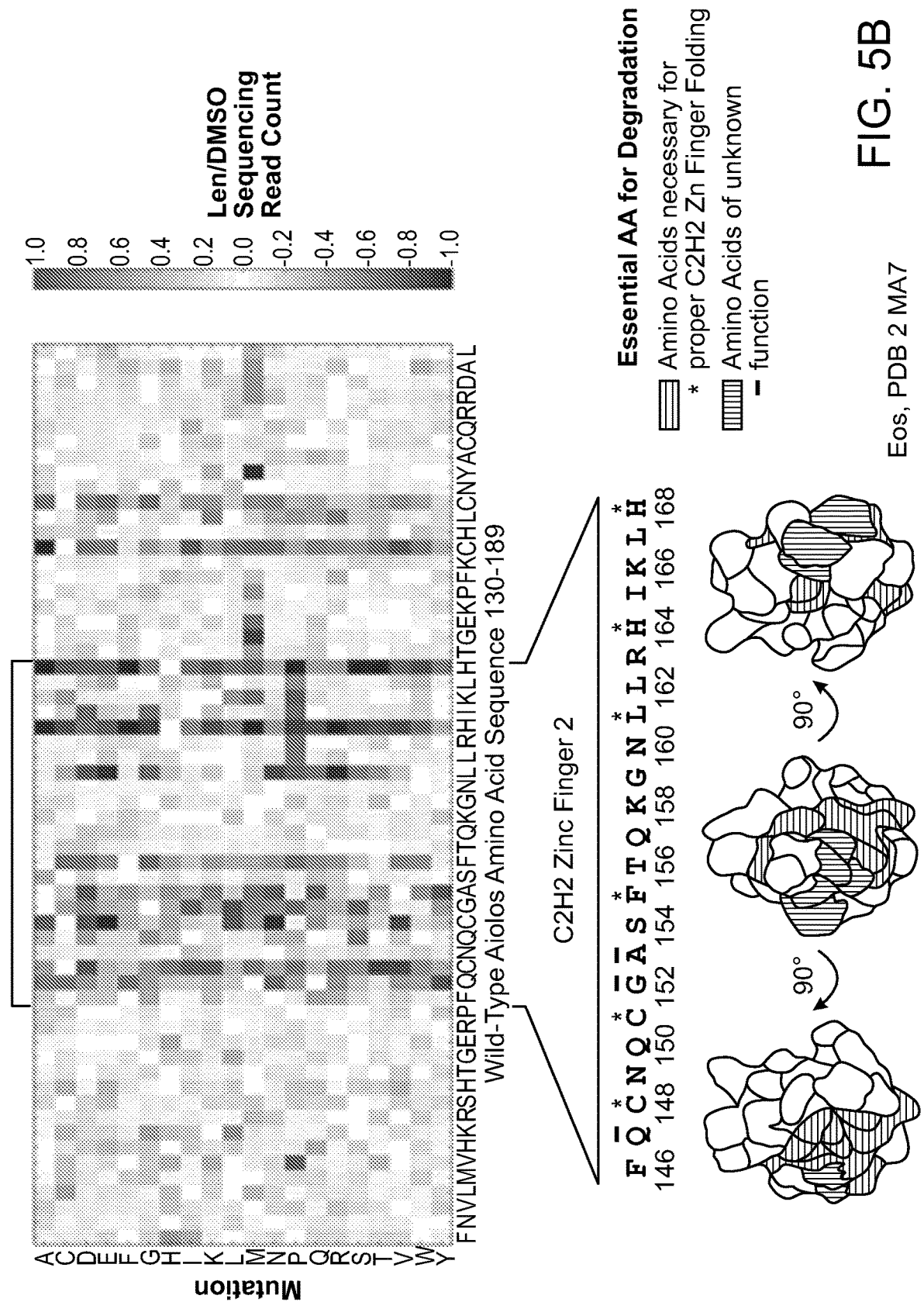

When examining the flow cytometry data from the screen, it was apparent that approximately 25% of the constructs in the library contained amino acid substitutions that impaired degradation by each of the three compounds. Representative data and the gating strategies for sorting are shown in FIG. 4. A cancer expressing one of these degradation resistant forms of Aiolos would be resistant to treatment with thalidomide, pomalidomide or lenalidomide. Analysis of the sequencing data from all three compounds clearly highlighted a number of amino acid residues necessary for degradation in the second C2H2 zinc finger motif of Aiolos (FIGS. 5A-5B). Without intending to be bound by theory, strong conservation of the cysteines (C) at residues 148 and 151, and the histidines (H) at residues 164 and 168 likely reflects their role in maintaining the structure of the zinc finger fold via chelation of a zinc ion. The phenylalanine (F) at 155 and leucine (L) at 161 are also common within C2H2 zinc fingers and likely were conserved due to their hydrophobic properties, which are also required for proper folding of the tertiary structure. Perhaps most intriguing then were the glutamine (Q) at position 147, as well as the glycine (G) and alanine (A) at positions 152 and 153, respectively; these residues are variable amongst C2H2 zinc fingers, and are candidates for being the amino acids which articulate with the drug-ubiquitin ligase complex. The cysteines at positions 176 and 179 belong to the adjacent C2H2 zinc finger motif which was truncated in the fragment which was screened, indicating that conservation of these residues is an artifact due to the fact that they cannot have formed a proper tertiary structure. Indeed, the cysteines at positions 176 and 179 were confirmed to be artifacts. The depletion of methionine C-terminal to the second C2H2 zinc finger motif is also suspected to represent an artifact, likely due to the fact that methionine may serve as an alternate start codon, facilitating "skipping" of the relevant sequence needed for degradation.

Following the screen described herein, several relevant avenues of questioning were pursued. First, the identification of the degron sequence within Aiolos (IKZF3) was validated by experimentally demonstrating that the second C2H2 zinc finger in Aiolos (IKZF3) (amino acids 146-169) was both necessary and sufficient to induce targeting by thalidomide, lenalidomide, and pomalidomide, as described further herein. Second, an active search of existing proteomic data for potential alternative protein targets of thalidomide, lenalidomide, and pomalidomide was performed. This examination preliminarily identified RNF166, ZNF692, and ZFP91 as candidates, as described further herein. If indeed these proteins are degraded in the presence of thalidomide, lenalidomide, or pomalidomide, the same comprehensive saturating mutagenesis screen will be performed to gain orthogonal information on what residues within the zinc fingers are relevant for drug induced targeting by the CRL4-CRBN ubiquitin ligase An implication of this work is to use a greater understanding of the consensus degron sequence or structural motif targeted by thalidomide, lenalidomide, and pomalidomide to either computationally or functionally search the proteome for novel targets of these compounds. Without intending to be bound by theory, novel targets may explain side effects of these compounds, the neurologic phenotype elicited by thalidomide, the teratogenicity of the drugs, or perhaps most desirably, the discovery of novel targets may warrant the clinical use of thalidomide, lenalidomide, and/or pomalidomide in other disorders.

Example 2: Identification of Amino Acid Sequence in Aiolos (IKZF3) that is Necessary and Sufficient to Mediate Degradation by Lenalidomide As described herein, a structural motif within the transcription factor Aiolos (IKZF3) that mediates its targeting by the CRL4-CRBN E3 ubiquitin ligase in complex with thalidomide, lenalidomide, and pomalidomide was identified in a screen. Specifically, the screen revealed that the drug-ubiquitin ligase complex recognizes the second, C2H2 zinc finger within Aiolos (IKZF3), with critical amino acids being those which mediate the tertiary structure of the zinc finger, as well as residues 146, 151, and 152, which are polymorphic between individual zinc fingers.

Figure 6A:
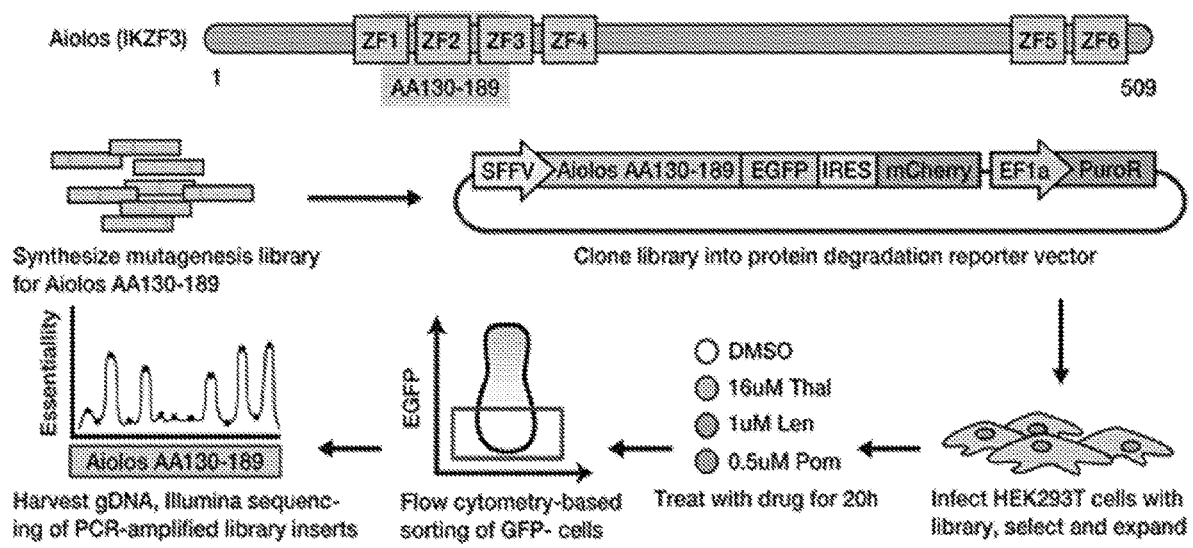
FIGS. 6A-6F provide a set of graphs and plots depicting that the second zinc finger within Aiolos is both necessary and sufficient for degradation by lenalidomide.
Figure 6B:
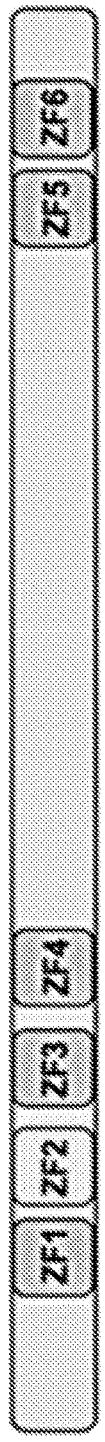
Figure 6C:
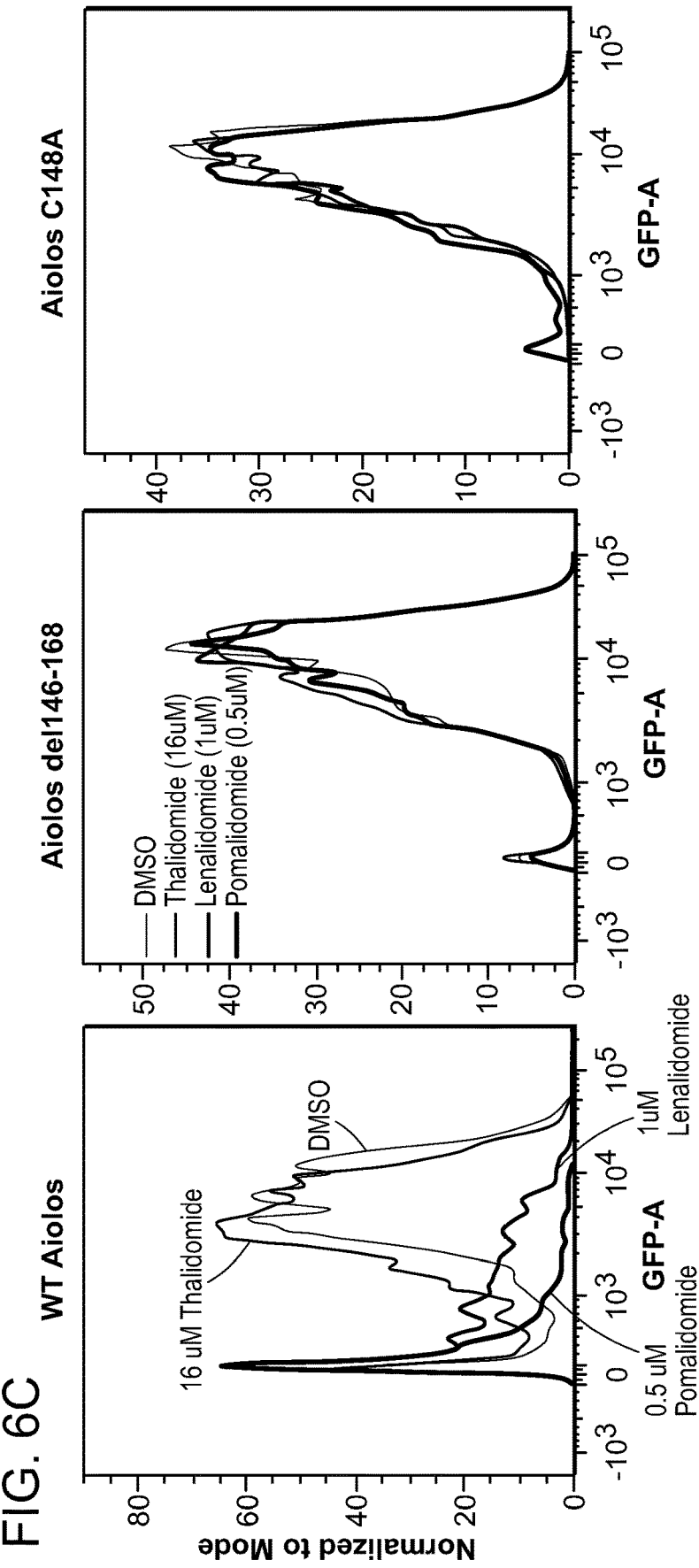
Figure 6D:
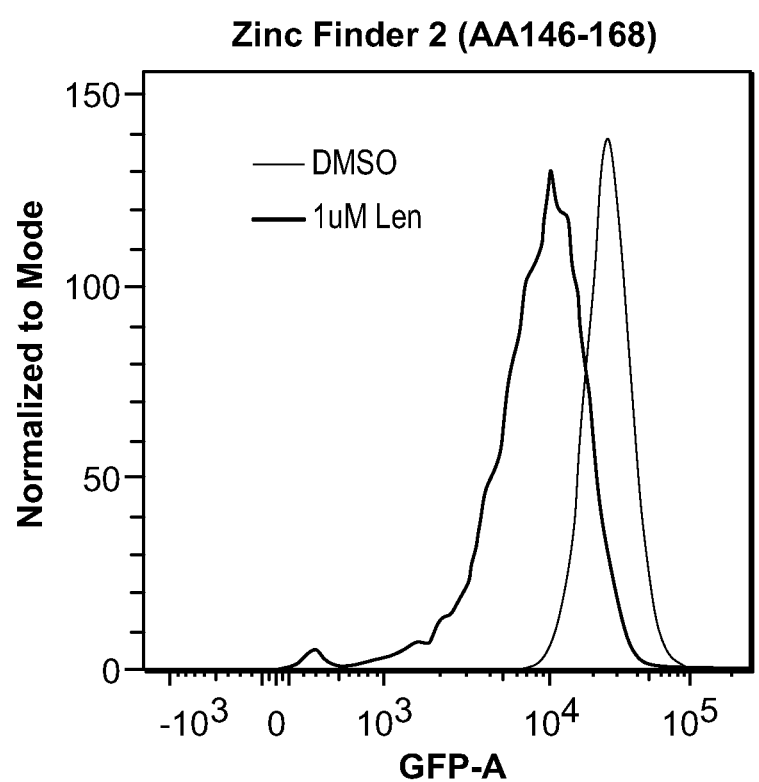
Figure 6E:
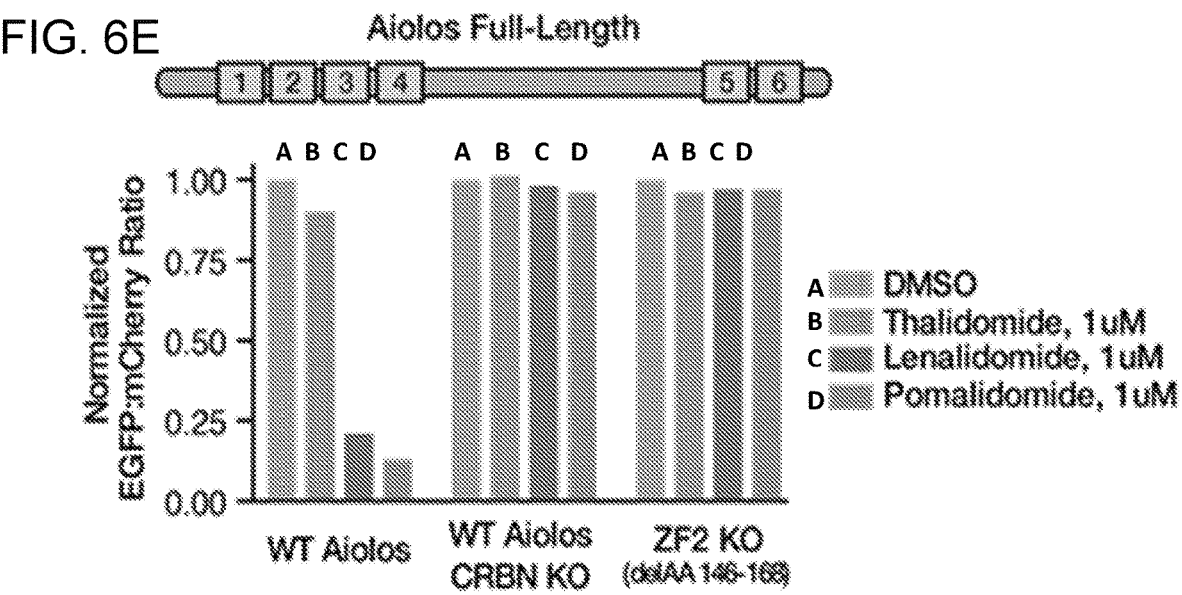
Figure 6F:
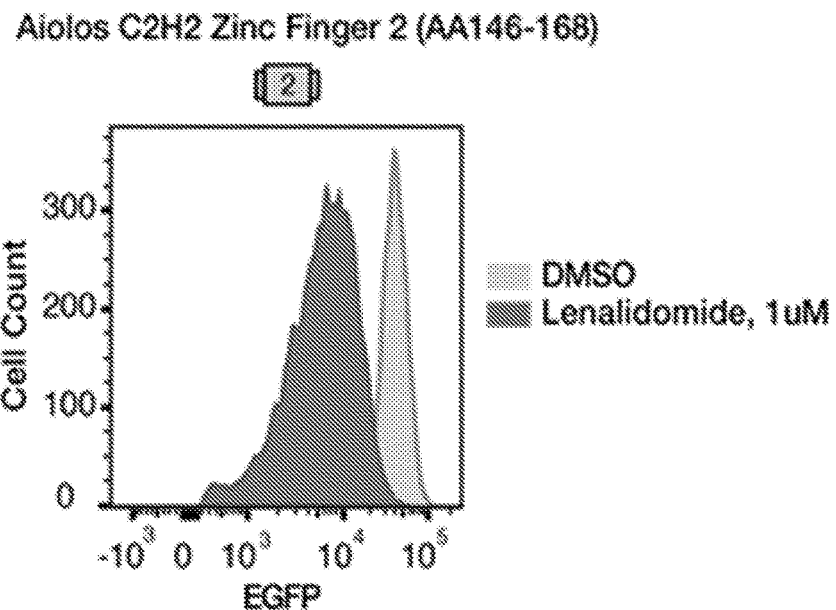

The results from the screen were confirmed by demonstrating that the second zinc finger within Aiolos is both necessary and sufficient for degradation by lenalidomide or lenalidomide analogs (FIGS. 6A-6F). Indeed, both deletion of the second zinc finger region or ablation of its zinc finger fold by mutating a key cysteine residue abrogated targeting of a GFP-tagged Aiolos by all three compounds (necessity) (FIG. 6B). Additionally, attaching zinc finger 2 (amino acids 146-168) to GFP via a flexible linker conferred lenalidomide-induced degradation of GFP (sufficiency) (FIG. 6C).

Figure 7A:
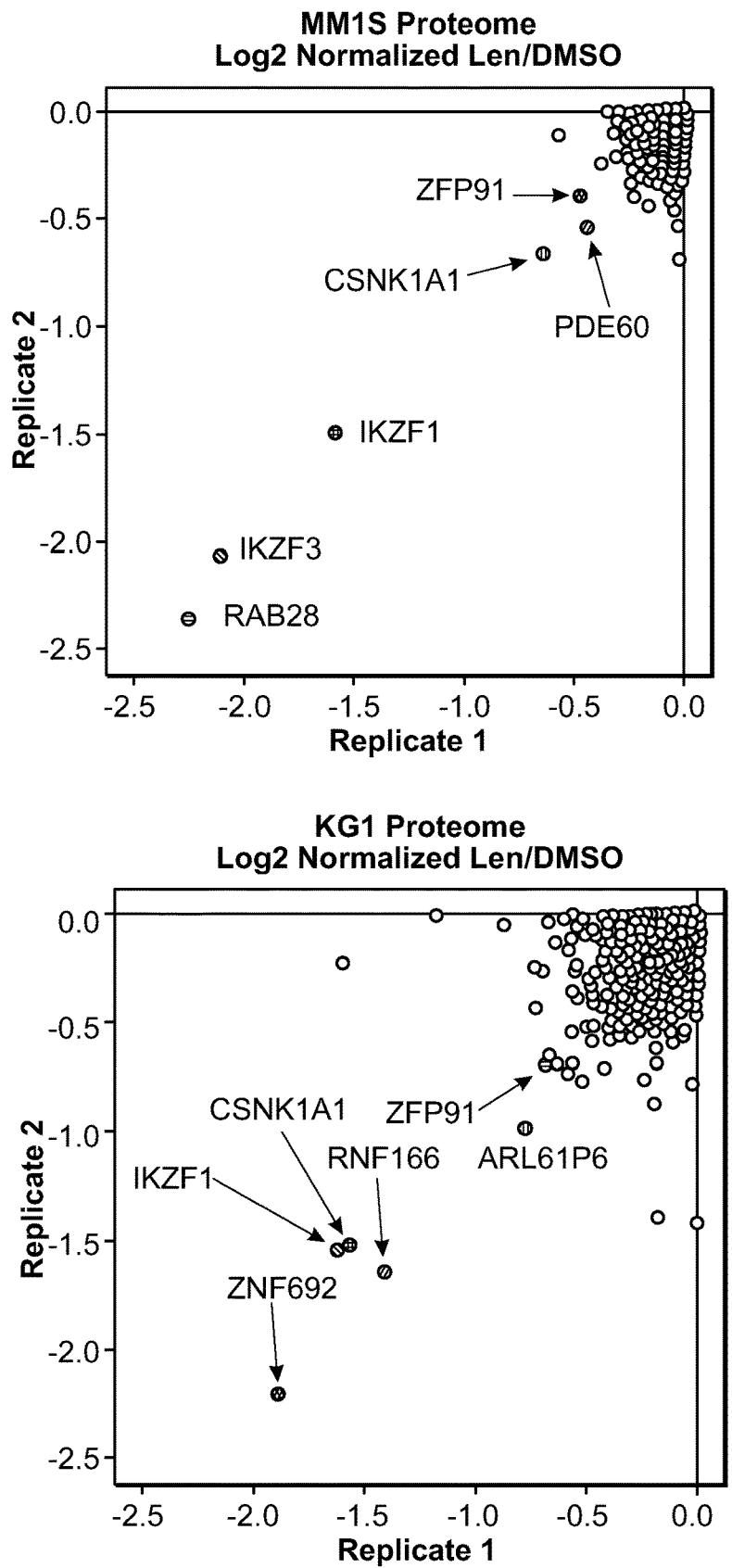
FIGS. 7A-7B provide a set of plots showing that three zinc finger proteins (RNF166, ZFP91, and ZNF692) exhibited significant decrease in abundance in the presence of lenalidomide or lenalidomide analogs, and that the zinc-finger containing regions of these proteins are targeted by lenalidomide and lenalidomide analogs.
Figure 7B:
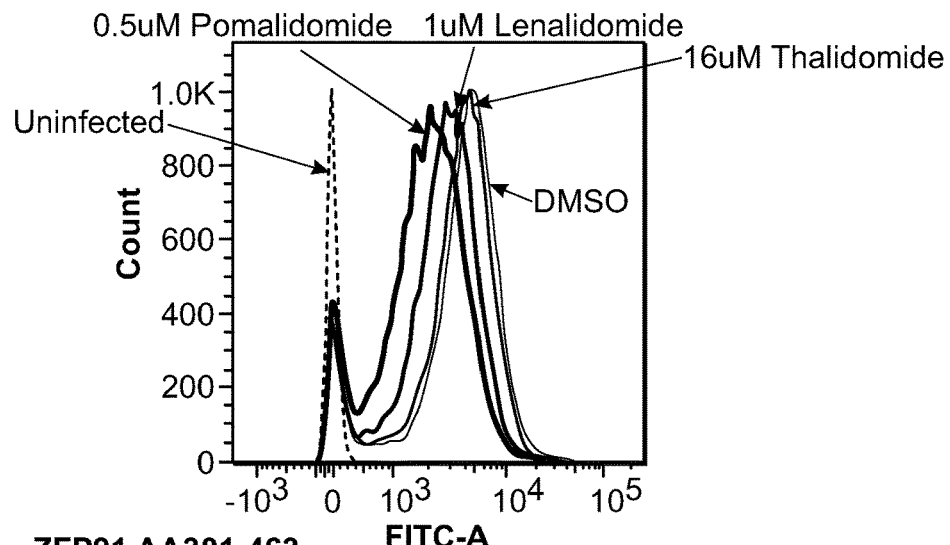
Figure 7B:
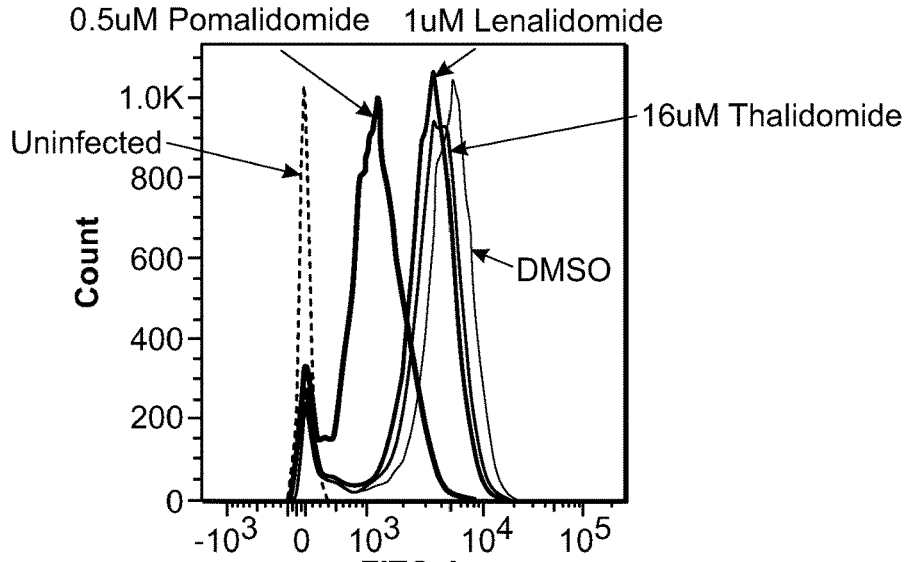
Figure 7B:
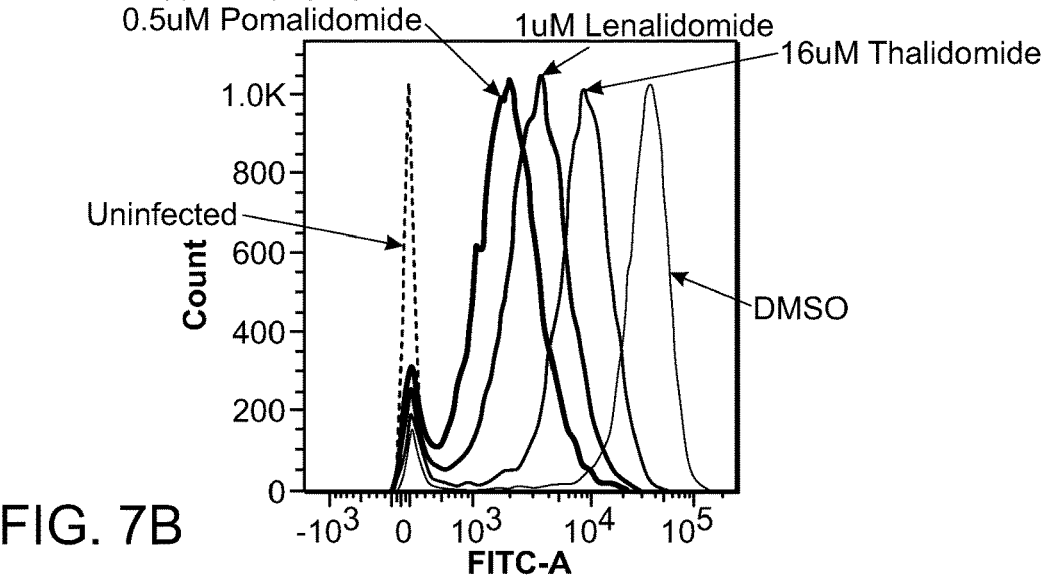
Figure 8:
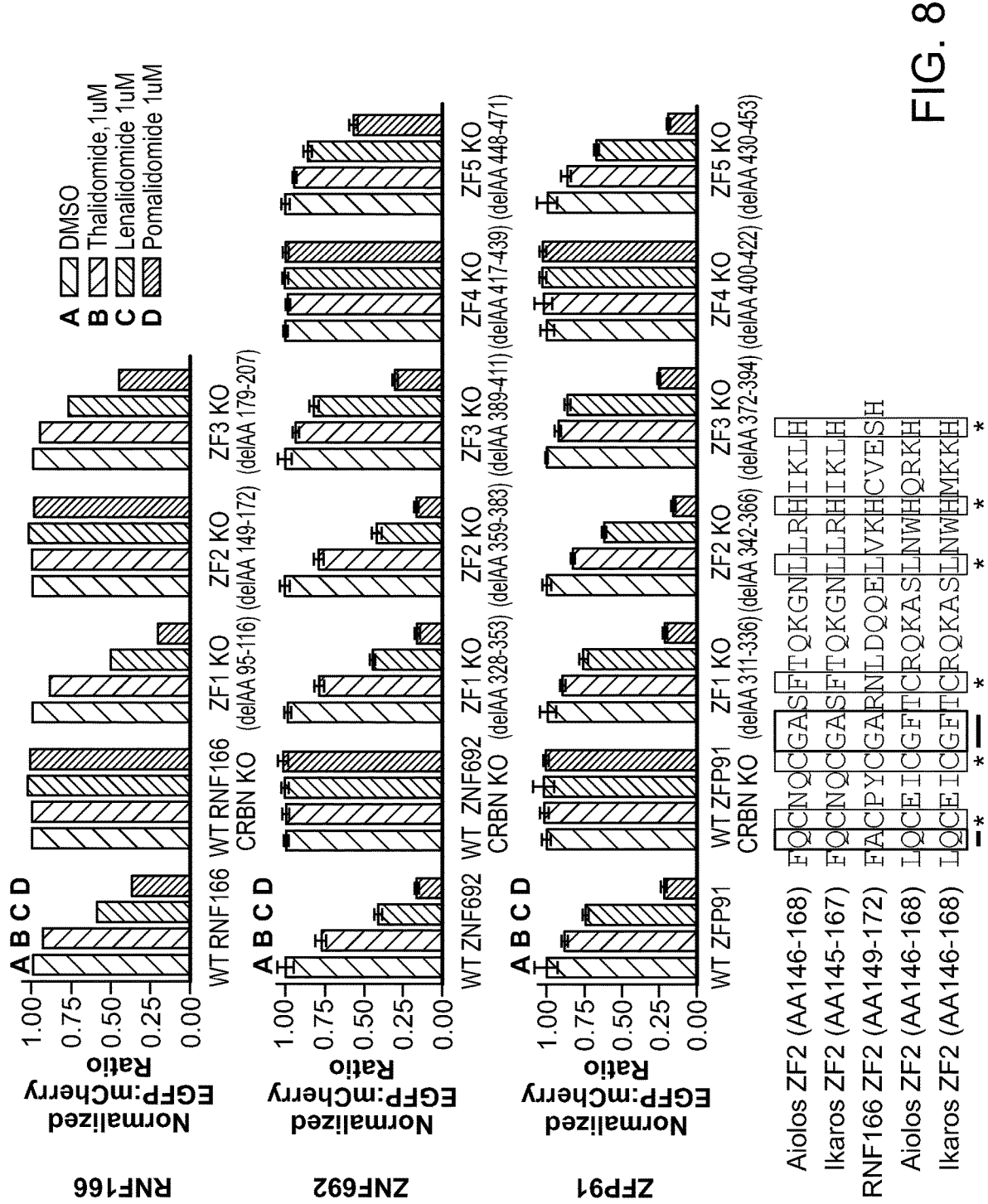
FIG. 8 provides a set of plots and diagrams showing that RNF166, ZNF692, and ZFP91 are C2H2 zinc finger-containing proteins which are degraded by thalidomide, lenalidomide, and pomalidomide in a cereblon and zinc finger-dependent fashion.

Example 3: Alternative Targets of Lenalidomide or Lenalidomide Analogs for CRL4-CRBN Mediated Ubiquitination and Degradation With the knowledge that these compounds are capable of directing CRL4-CRBN mediated ubiquitination and degradation of proteins containing zinc finger motifs, two proteomic datasets derived from treatment of the cell lines MM1S (multiple myeloma) and KG1 (Acute Myeloid Leukemia) with thalidomide and lenalidomide were more closely examined (Kronke et al., Science 343, 301-305 (2014); Kronke et al., Nature 523, 183-188 (2015)). Indeed, there were three zinc finger proteins which exhibited a significant decrease in abundance in the presence of drug: RNF166, ZFP91, and ZNF692 (FIG. 7A). Preliminary data shown herein confirmed that the zinc-finger containing regions of these proteins are targeted by thalidomide, lenalidomide, and pomalidomide for degradation at the protein level (FIG. 7B; FIG. 8).

Signaling through the NFKB pathway has been noted to be impaired in the presence of thalidomide, lenalidomide, and pomalidomide. However, this effect has yet to be explained by a molecular target. ZFP91 is therefore of interest because it is a critical member of the non-canonical NFKB signaling pathway, with existing evidence that a reduction of its protein levels is capable of impairing non-canonical NFKB signaling (Jin et al., Journal of Biological Chemistry 285, 30539-30547 (2010); Jin et al., Biochem. Biophys. Res. Commun. 400, 581-586 (2010)). The hypothesis that degradation of ZFP91 by these compounds explains the ability of these drugs to inhibit NFKB signaling will be pursued. Without intending to be bound by theory, this property may also mechanistically illuminate additional, unexplained cellular and clinical phenotypes such as the inhibition of TNFa secretion by monocytes, anti-angiogenesis, anti-inflammatory properties, and tumoricidal effects of these drugs in multiple myeloma and acute myeloid leukemia.

Example 4: Results of Screen for Genes that Mediate Resistance to Lenalidomide in Multiple Myeloma In an effort to discover genes whose loss confers resistance to lenalidomide, a pooled, genome-wide CRISPR-Cas9 screen in the lenalidomide-sensitive myeloma cell line, MM1S, was performed. Loss of cereblon has been noted to promote resistance to lenalidomide in cell line models (Zhu et al., 2011, Blood 118, 4771-4779; Lopez-Girona et al., 2012, Leukemia 26, 2326-2335). Therefore, parameters for the screen, including dose and endpoints, were optimized using cereblon gRNAs as a positive control.

In this study, a set of genes whose loss conferred resistance to lenalidomide was identified from a genome-wide screen performed in a lenalidomide-sensitive myeloma cell line. The screen was carried out as follows: on day 8, Cas9-expressing MM1S cells were infected at an efficiency of 46% with the second-generation "GEKO" gRNA library designed by the Zhang lab and Genetic Perturbations Platform at the Broad Institute; this library contains approximately 120,000 gRNAs targeting 18,000 genes (~6 gRNA/gene) (Sanjana et al., 2014, Nature Methods 11, 783-784). On day 0, a baseline control sample of 120 million cells was taken and the remaining infected cells began treatment with either DMSO (1x 60 million cells) or 1 µM lenalidomide (2 sets of 3×120 million cells). The number of cells per replicate in the DMSO and 1 µM lenalidomide treatment groups ensured an estimated representation of each gRNA in 500 and 1000 cells, respectively. Endpoint samples were collected on days 12 (D12) and 20 (D20) (FIG. 9A). Genomic DNA was isolated from each of the collected samples and relative gRNA abundance was determined via barcoded PCR amplification of the genomic gRNA insert and pooled sequencing of the resultant amplicons across four lanes of the Illumina HiSeq. Read counts were normalized and log 2 transformed, and the D12 and D20 replicates were averaged. The fold-change in gRNA abundance upon selection with lenalidomide was calculated by comparing the relative abundance of a given gRNA in the lenalidomide-treated experimental condition to its relative abundance in the corresponding DMSO control (FIGS. 9A-9B). A plot showing the gRNA library ranked according to the Len/DMSO fold-change of the log 2-transformed gRNA read count (average of 3 replicates) is shown in FIG. 9B.

Figure 9C:
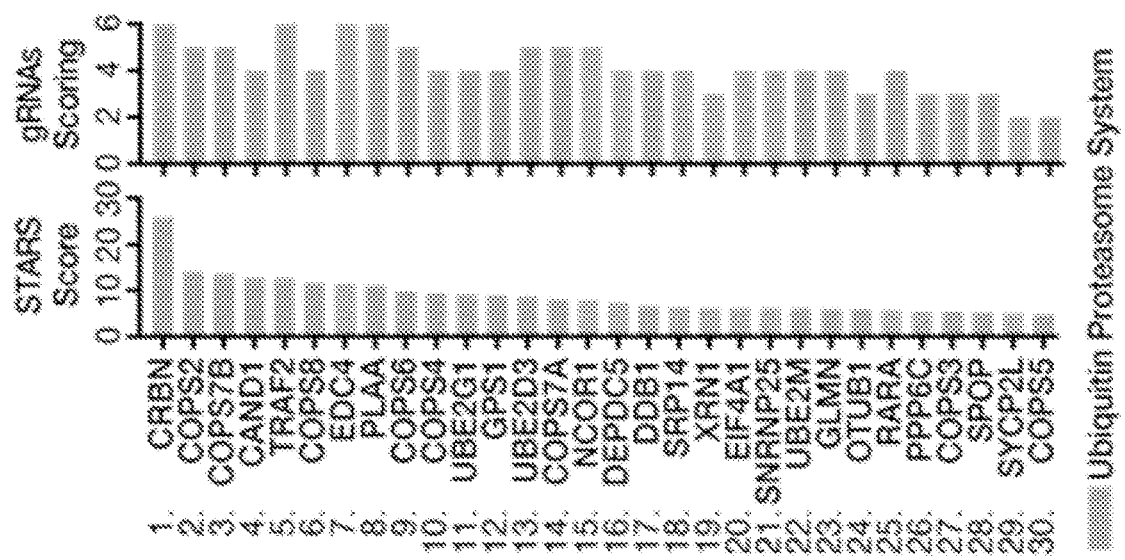
FIGS. 9A-9C provide plots and diagrams showing that a genome-scale CRISPR-Cas9 screen in lenalidomide-treated MM1S cells revealed genes whose loss conferred resistance to lenalidomide.
Figure 9B:
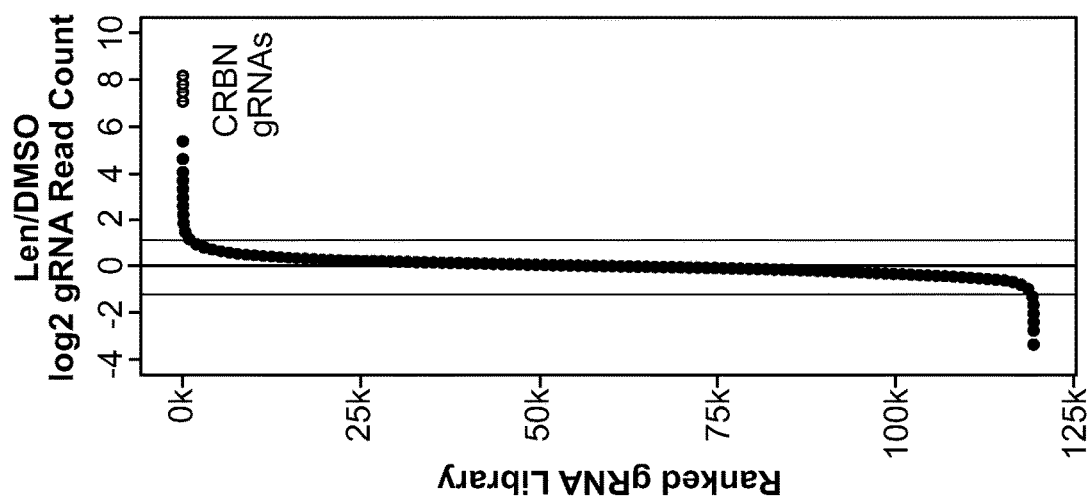
Figure 9A:
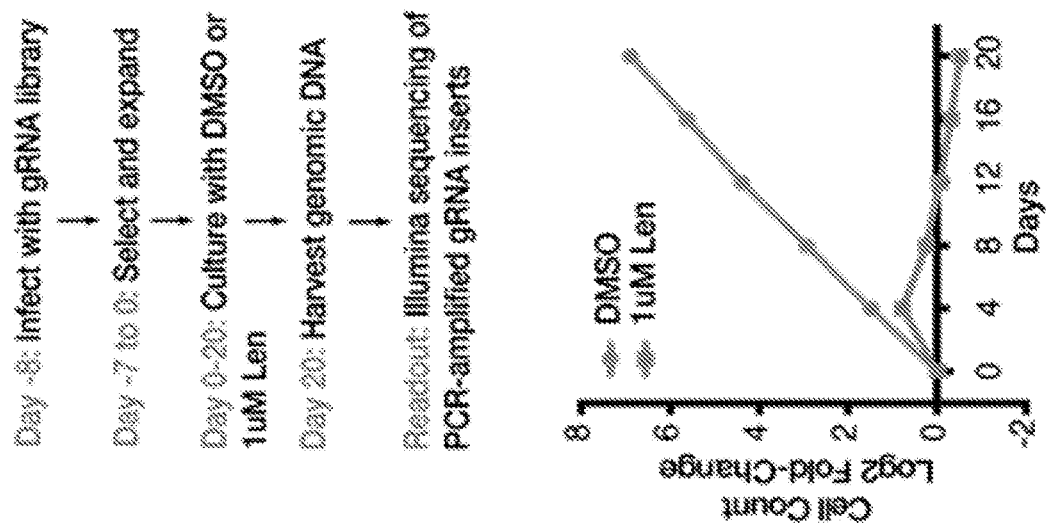

An examination of the gRNA rankings at D20 revealed that all six of the gRNAs targeting cereblon (CRBN) to be amongst the top 7 and top 6 gRNAs, respectively, confirming the screen optimization procedures (FIG. 9C; Table 1). To discover additional genes whose loss confers resistance to lenalidomide, the STARS algorithm (Genetic Perturbations Platform) was used to collapse gRNA rankings by gene and assign p, FDR (false discovery rate), and q values, as well as a composite STARS score. In comparison to D12, the D20 data yielded hits with much higher confidence, with the top 30 genes possessing FDR values below 0.05. In keeping with the mechanism of lenalidomide, cereblon was ranked first, and of the top 30 genes, 18 are regulators of cullin-ring ligases and/or participants in the ubiquitin-proteasome pathway. Most notably, all 9 members of the COPS signalosome complex in scored with FDRs less than 0.05 (GPS1 [12], COPS2 [2], COPS3 [27], COPS4 [10], COPS5 [30], COPS6 [9], COPS7A [14], COPS7B [3], COPS8 [6]). Additional genetic modules that emerged as themes in the D20 STARS ranking of genes are CRL4-CRBN complex members (CRBN [1], DDB1 [17], CUL4B [52]), NFKB pathway (TRAF2 [5], NFKBIA [32]), members of the 5' mRNA decapping complex (EDC4 [7], XRN1 [19], DCP2 [36]), nuclear hormone receptor signaling (NCOR1 [15], RARA [25]), and tumor suppressors which have recently been noted to be relevant in melanoma (PPP6C [26], SPOP [28]). Novel components of the CRL4-CRBN E3 ubiquitin ligase pathway identified in the screen included two E2 enzymes, UBE2G1 and UBE2D3.

TABLE 1

Genes whose loss conferred resistance to lenalidomide

CRBN
COPS2
COPS7B
CAND1
TRAF2
COPS8
EDC4
PLAA
COPS6
UBE2G1
GPS1
UBE2D3
COPS7A
NCOR1
DEPDC5
DDB1
SRP14
XRN1
EIF4A1
SNRNP25
UBE2M
GLMN
OTUB1
RARA
PPP6C
COPS3
SPOP
SYCP2L
COPS5
RBX1

TABLE 1-continued

Genes whose loss conferred resistance to lenalidomide

CUL4A
CUL4B

Figures 10A, 10B:
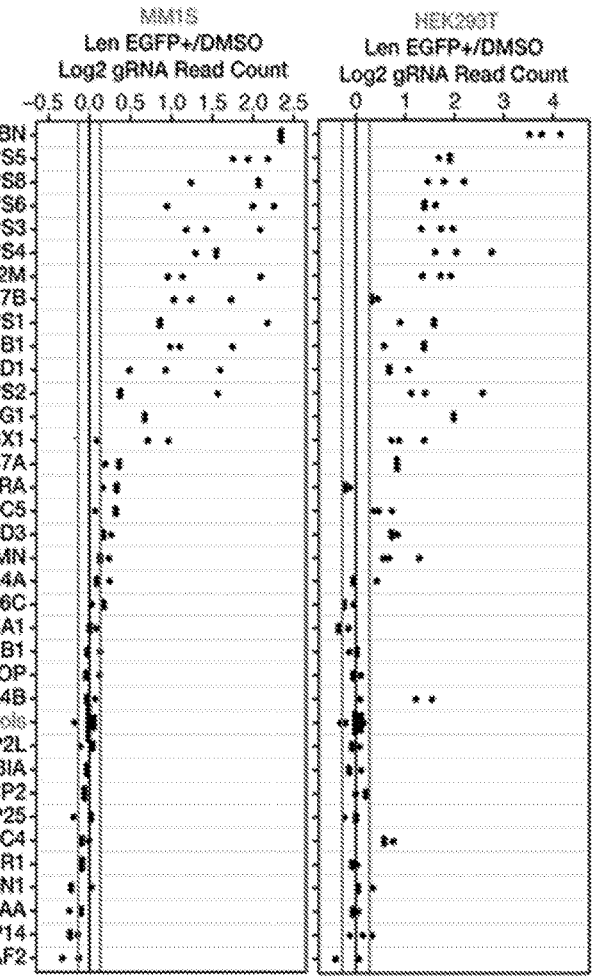
FIGS. 10A-10B provide plots and diagrams showing that a Aiolos degradation reporter screen identified genes which are required for lenalidomide-induced degradation of Aiolos.

A focused, pooled viral gRNA library was made containing an orthogonal set of gRNAs targeting the top 30 hits from the screen as well as NFKBIA [32], DCP2 [36], CUL4B [52], and the CRL4-CRBN complex members which did not score in the screen, CUL4A and RBX1. The focused library was designed using an on-target prediction algorithm and specifically contains three gRNAs per gene, each targeting a different exon in the first 50% of the protein (Doench et al., 2014, Nat. Biotechnol. doi:10.1038/nbt.3026). In the same manner as the original screen, this library was used to validate the hits in Cas9-expressing MM1S cells as well as three other lenalidomide-sensitive myeloma cell lines: OPM2, U266, and NCIH929. To determine which of the hits prevent degradation of the Aiolos transcription factor the same focused viral library was screened in an MM1S, NCIH929, and HEK293 T reporter cell lines expressing Aiolos tagged to GFP; flow cytometry-based sorting of GFP high and low cells following a 20 hour incubation with lenalidomide was used to isolate cells carrying gRNAs that did or did not impair Aiolos degradation. Subsequently, gDNA isolation, PCR amplification of the gRNA insert, and Illumina-based sequencing were used as a readout. Results of the screen of this library are shown in FIGS. 10A-10B.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of identifying increased polypeptide degradation in a cell, the method comprising:

contacting a cell with a modulator of cereblon (CRBN); and detecting in a first polypeptide in the cell the presence of a sequence substantially identical to an amino acid sequence FQCNQCGASFTQKGNLLRHIKLH (SEQ ID NO: 1), in an amino terminus ($NH_2$) to carboxy terminus (COOH) orientation, and detecting in a second polypeptide in the cell the presence of at least one amino acid sequence substantially identical to a sequence, in an $NH_2$ to COOH orientation, selected from:

FACPYCGARNLDQQELVKHCVESH; (SEQ ID NO: 2)

LQCEICGFTCRQKASLNWHQRKH; (SEQ ID NO: 3)

or

LQCEICGFTCRQKASLNWHMKKH; (SEQ ID NO: 4)

wherein detecting the sequences in the first and second polypeptides in the cell indicates increased polypeptide degradation in the cell contacted with the modulator of CRBN.

2. The method of claim 1, wherein the first or the second polypeptide in the cell is IKZF3, IKZF1, RNF166, ZNF692, or ZFP91.

3. The method of claim 1, wherein the modulator of CRBN is lenalidomide, thalidomide, or pomalidomide.

4. The method of claim 1, wherein detecting the presence of the sequence in the first polypeptide and the sequence in the second polypeptide indicates that the first and second polypeptides in the cell are drug-modulated polypeptide substrates of CRBN.

5. The method of claim 1, wherein detecting the presence of the sequences in the first and second polypeptides in the cell indicates that the polypeptides are drug-modulated polypeptide substrates of CRBN; and wherein detecting the presence of the sequences in the first and second polypeptides in the cell indicates that the polypeptides are polypeptide targets of a modulator of CRBN.

6. The method of claim 1, wherein the first and the second polypeptides in the cell are degraded by CRBN-mediated degradation when the cell is contacted with the modulator of CRBN.

7. The method of claim 1, wherein contacting the cell with a modulator of CRBN depletes the polypeptides in the cell.

8. The method of claim 1, wherein one or both of the first and the second polypeptide sequences comprises a C2H2 zinc finger sequence.

9. The method of claim 8, wherein amino acid positions in the C2H2 zinc finger sequence corresponding to amino acids 2, 7, and 8 in an amino terminus to carboxy terminus orientation in SEQ ID NO: 1 comprise glutamine (Gln), glycine (Gly), or alanine (Ala).

* * * * *